(12) United States Patent
Kojima et al.

(10) Patent No.: US 9,284,534 B2
(45) Date of Patent: Mar. 15, 2016

(54) CHOLESTEROL OXIDASE MUTANTS, COMPOSITIONS, DEVICES, KITS AND USES THEREOF

(71) Applicants: Roche Diabetes Care, Inc., Indianapolis, IN (US); Ultizyme International, Ltd., Tokyo (JP)

(72) Inventors: Katsuhiro Kojima, Tokyo (JP); Kazushige Mori, Tokyo (JP); Sode Koji, Tokyo (JP)

(73) Assignees: Ultizymer International, Ltd., Tokyo (JP); Roche Diabetes Care, Inc., Indianapolis, IN (US)

(*) Notice: Subject to any disclaimer, the term of this patent is extended or adjusted under 35 U.S.C. 154(b) by 0 days.

(21) Appl. No.: 14/187,914

(22) Filed: Feb. 24, 2014

(65) Prior Publication Data

US 2014/0255959 A1    Sep. 11, 2014

Related U.S. Application Data

(63) Continuation of application No. PCT/EP2012/003574, filed on Aug. 24, 2012.

(30) Foreign Application Priority Data

Aug. 25, 2011  (EP) ..................... 11006940

(51) Int. Cl.

| | |
|---|---|
| C12Q 1/60 | (2006.01) |
| C12N 9/04 | (2006.01) |
| C12P 21/06 | (2006.01) |
| C12P 19/34 | (2006.01) |
| C12N 15/00 | (2006.01) |
| C12N 1/20 | (2006.01) |
| C12Q 1/00 | (2006.01) |
| C07H 21/04 | (2006.01) |
| C07K 1/00 | (2006.01) |
| C12Q 1/26 | (2006.01) |
| G01N 33/92 | (2006.01) |

(52) U.S. Cl.
CPC .............. *C12N 9/0006* (2013.01); *C12Q 1/005* (2013.01); *C12Q 1/26* (2013.01); *C12Q 1/60* (2013.01); *C12Y 101/03006* (2013.01); *G01N 33/92* (2013.01)

(58) Field of Classification Search
CPC ............ C12Q 1/005; C12Q 1/26; C12Q 1/60; C12N 9/0006; C12Y 101/03006; G01N 33/92
USPC ........... 435/11, 190, 69.1, 91.1, 320.1, 252.3; 204/403.14; 205/777.5; 536/23.1, 23.2; 530/350
See application file for complete search history.

(56) References Cited

U.S. PATENT DOCUMENTS 7,208,287 B2 * 4/2007 Kishi et al. ...................... 435/11

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
The Basics: In Vitro Translation, Life Technolgies, https://www.lifetechnologies.com/us/en/references; 5 pages downloaded on Jun. 20, 2015.*
Promega Technical Manual, http://www.promega.com, 32 pages downloaded on Jun. 20, 2015.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
International Search Report issued Mar. 7, 2013, in Application No. PCT/EP2012/003574, 7 pages.
Database Uniprot (Online), "SubName: Full=Cholesterol oxidase; EC=1.1.3.6; Flags: Precursor," May 2007, 1 page, retrieved from EBI Accession No. A4X855.
Database Uniprot (Online), "SubName: Full=Cholesterol oxidase (CHOD)," Oct. 2010, 1 page, retrieved from EBI Accession No. D9WHR8.
Database Uniprot (Online), "SubName: Full=Putative cholesterol oxidase," Nov. 2010, 1 page, retrieved from EBI Accession No. E0TBM8.
Database Uniprot (Online), "SubName: Full-Putative cholesterol oxidase," Nov. 2004, 1 page, retrieved from EBI Accession No. Q5Z338.
Doukyu, Noriyuki, "Characteristics and biotechnological applications of microbial cholesterol oxidases," Jul. 2009, Applied Microbiology and Biotechnology, pp. 825-837, vol. 83, No. 5.
Ishikawa, Jun et al., "The complete genomic sequence of *Nocardia farcinica* IFM 10152," Proceedings of the National Academy of Sciences, Oct. 2004, pp. 14925-14930, vol. 101, No. 41.
Parra, A. et al., "Bioanalytical device based on cholesterol oxidase-bonded SAM-modified electrodes," Analytical and Bioanalytical Chemistry, Mar. 2007, pp. 1059-1067, vol. 388, No. 5-6.
Pollegioni, Loredano et al., "Cholesterol oxidase: biotechnological applications," FEBS Journal, Dec. 2009, pp. 6857-6870, vol. 276, No. 23.
Sun, Yan et al., "Improvement of the thermostability and enzymatic activity of cholesterol oxidase by site-directed mutagenesis," Biotechnology Letters, Jun. 2011, pp. 3049-3055, vol. 33, No. 10.
Toyama, Mitsutoshi et al., "Alteration of substrate specificity of cholesterol oxidase from *Streptomyces* sp. by site-directed mutagenesis," Protein Engineering, Jun. 2002, pp. 477-483, vol. 15, No. 6.
Vrielink, Alicia and Ghisla, Sandro, "Cholesterol oxidase: biochemistry and structural features," FEBS Journal, Dec. 2009, pp. 6826-6843, vol. 276, No. 23.
Yue, Q. Kimberley et al., "Crystal Structure Determination of Cholesterol Oxidase from *Streptomyces* and Structural Characterization of Key Active Site Mutants," Biochemistry, Apr. 1999, pp. 4277-4286, vol. 38, No. 14.

* cited by examiner

*Primary Examiner* — Ganapathirama Raghu
(74) *Attorney, Agent, or Firm* — Roche Diabetes Care, Inc.

(57) ABSTRACT

Compositions, devices, kits and methods are disclosed for assaying cholesterol with a cholesterol oxidase mutant that has been modified at an amino acid residue involved in the active site. The cholesterol oxidase mutant has reduced oxidase activity while substantially maintaining its dehydrogenase activity.

15 Claims, No Drawings

CHOLESTEROL OXIDASE MUTANTS, COMPOSITIONS, DEVICES, KITS AND USES THEREOF

CROSS-REFERENCE TO RELATED APPLICATIONS

This patent application is a continuation of Int'l Patent Application No. PCT/EP2012/003574; filed 24 Aug. 2012, which claims the benefit of EP Patent Application No. 11006940.8; filed 25 Aug. 2011. Each patent application is incorporated herein by reference as if set forth in its entirety.

REFERENCE TO SEQUENCE LISTING SUBMITTED ELECTRONICALLY

An official copy of a Sequence Listing is submitted electronically via EFS-Web as an ASCII-formatted Sequence Listing with a file named "27498SequenceListing.txt," created on 14 Jan. 2014, and having a size of 254 KB. The Sequence Listing is filed concurrently with the Specification, is a part thereof and is incorporated herein by reference as if set forth in its entirety.

TECHNICAL FIELD

This disclosure relates generally to chemistry, medicine and molecular biology, and more particularly, it relates to a cholesterol oxidase mutant having a reduced oxidase activity that can be used in a biosensor test strip, enzyme electrode, sensor and/or kit for measuring cholesterol.

BACKGROUND

The concentration of lipoproteins in blood is important in clinical tests. Lipoproteins can be divided into two groups—high density lipoproteins (HDL) and low density lipoproteins (LDL), each of which having different biological functions. As a measure of the lipoprotein content in blood, cholesterol associated with the lipoproteins is measured. In biological samples like blood, cholesterol is present in the lipoproteins in the form of cholesterol esters.

To measure the lipoprotein-associated cholesterol levels, the cholesterol esters are split by enzymes such as cholesterol esterase. Once freed, cholesterol then is determined. The cholesterol concentration in blood may be measured using an enzyme having specificity to cholesterol such as, for example, cholesterol oxidase (ChOx).

ChOx has been isolated from various organisms, and it has been suggested that cholesterol may be analyzed using such enzymes. ChOx is a flavin adenine dinucleotide (FAD)-dependent enzyme that catalyzes a reaction where cholesterol is oxidized to generate cholest-4-en-3-one, thereby generating the reduced form of FAD, $FADH_2$. $FADH_2$, in turn, transmits electrons to an electron acceptor and is converted to its oxidized form. In the presence of oxygen, $FADH_2$ preferentially transmits electrons to oxygen molecules rather than to artificial electron acceptors (also referred to as mediators or electron mediators). Thus, when cholesterol is assayed by ChOx with mediators, the assay results will be greatly affected by the dissolved oxygen level in the reaction system. Such a disadvantage will be particularly noted in clinical tests of blood samples by a point-of-care testing device utilizing an artificial electron acceptor. Therefore, enzymes used for enzyme biosensor test strips employing artificial electron mediators desirably have low activity toward oxygen.

For the foregoing reason, there is a need for an enzyme, in particular, a ChOx having an activity that is less affected by the dissolved oxygen level.

BRIEF SUMMARY

An inventive concept described herein includes an enzyme, in particular, a ChOx having an activity that is less affected by a dissolved oxygen level. This concept is achieved by reducing the oxidase activity of an enzyme that in its wild-type form predominantly shows an oxidase activity and also by preferably at the same time increasing the enzyme's dehydrogenase activity. As will be described in more detail below, this has been achieved by modifying the wild-type enzyme.

The disclosure describes various ChOx mutants, and it was surprisingly found that a certain type of mutants exhibits reduced oxidase activity while substantially retaining dehydrogenase activity, in particular dye-mediated dehydrogenase activity.

In an aspect, a ChOx mutant is provided. In some instances, the ChOx mutant can be modified at one or more positions such as:

(a). a position corresponding to position 159 of the amino acid sequence set forth in SEQ ID NO: 1 by substituting the amino acid residue Met with an amino acid residue such as Phe, Leu, Val, Cys, Ile, Ala, Gln, Tyr, Lys or Ser or by substituting the amino acid residue Ile with an amino acid residue such as Phe, Leu, Val, Cys, Ala, Gln, Tyr, Lys or Ser;

(b). a position corresponding to position 228 of the amino acid sequence set forth in SEQ ID NO: 1 by substituting the amino acid residue Val, Met or Ile with an amino acid such as Ala, Thr, Lys, Cys, Ser, Gly, Glu, Tyr, Pro, Asn, Gln, Trp or His; and (c). a position corresponding to position 396 of the amino acid sequence set forth in SEQ ID NO: 1 by substituting the amino acid residue Phe with an amino acid residue such as Trp, Ser, Thr, Lys, Ala, Asn, His or Asp.

Regardless of the substitution, the ChOx mutant has a reduced oxidase activity when compared to a wild-type ChOx. Specifically, the ChOx mutant can have an oxidase activity of about 30% or less than that of the wild-type ChOx and optionally can have an increased dehydrogenase activity when compared to the wild-type ChOx. In some instances, the ChOx mutant has a dehydrogenase activity of about 50% or more when compared to the wild-type ChOx.

In another aspect, an isolated polynucleotide is provided that encodes a ChOx mutant as described herein.

In another aspect, a vector is provided that includes a polynucleotide encoding a ChOx mutant as described herein.

In another aspect, a host cell is provided that is transformed with a vector as described herein.

In another aspect, a device is provided for assaying cholesterol in a sample, where the device includes a modified ChOx as described herein and optionally an electron mediator. In some instances, an enzyme electrode is provided, where the enzyme electrode includes a modified ChOx as described herein that is immobilized on the electrode. In other instances, an enzyme sensor is provided for assaying cholesterol, where the enzyme sensor includes an enzyme electrode as described herein as a working electrode.

In another aspect, a kit is provided for assaying cholesterol in a sample, where the kit includes a modified ChOx as described herein and optionally an electron mediator.

In view of the foregoing, a method is provided for assaying cholesterol, including lipoprotein-associated cholesterol, in a sample. The method can include contacting the sample with a ChOx mutant as described herein and then measuring an amount of cholesterol oxidized by the modified ChOx. In some instances, the ChOx mutant is incorporated into a device such as a biosensor test strip, enzyme electrode or sensor as described herein.

These and other advantages, effects, features and objects of the inventive concept will become better understood from the description that follows. The description of exemplary embodiments is not intended to limit the inventive concept to the particular forms disclosed, but on the contrary, the intention is to cover all modifications, equivalents and alternatives falling within the spirit and scope of the inventive concept as defined by the embodiments above and the claims below. Reference should therefore be made to the embodiments above and claims below for interpreting the scope of the inventive concept.

DETAILED DESCRIPTION OF PREFERRED EMBODIMENTS

The compositions, devices, kits and methods now will be described more fully hereinafter, in which some, but not all embodiments of the inventive concept are shown. Indeed, the compositions, devices, kits and methods may be embodied in many different forms and should not be construed as limited to the embodiments set forth herein; rather, these embodiments are provided so that this disclosure will satisfy applicable legal requirements.

Likewise, many modifications and other embodiments of the compositions, devices, kits and methods described herein will come to mind to one of skill in the art to which the disclosure pertains having the benefit of the teachings presented in the foregoing description. Therefore, it is to be understood that the compositions, devices, kits and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the inventive concept pertains. Although any methods and materials similar to or equivalent to those described herein can be used in the practice or testing of the compositions, devices, kits and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Exemplary compositions, devices, kits and methods are provided for measuring cholesterol, including HDL- and LDL-associated cholesterol, and are based upon a ChOx mutant less affected by a dissolved oxygen level. This concept can be achieved at the very least by reducing the oxidase activity of the ChOx mutant when compared to a wild-type ChOx. In addition, the ChOx mutant can be modified to increase its dehydrogenase activity when compared to the wild-type ChOx. This concept is in contrast to current compositions, devices, kits and methods that largely rely on wild-type ChOx.

Such compositions, devices, kits and methods incorporating a ChOx mutant as described herein are useful in a variety of applications. For example, the ChOx mutant may be used for measuring cholesterol or lipoproteins associated with cholesterol, such as HDL or LDL, which is clinically useful in diagnosing and controlling certain health conditions.

The work described herein is the first to show that the disadvantages noted above can be solved with a ChOx mutant having at least a reduced oxidase activity and optionally an increased dehydrogenase activity. The present inventive concept therefore provides compositions, devices, kits and methods for measuring cholesterol.

Compositions

Cholesterol Oxidase Mutants: One composition encompassing the inventive concept includes an isolated, ChOx mutant that exhibits decreased oxidase (or Ox) activity when compared to a wild-type ChOx while substantially retaining dehydrogenase (or Dh) activity. In some instances, the ChOx mutant further exhibits an increased Dh activity when compared to the wild-type ChOx.

As used herein, "isolated," with respect to a polypeptide (and also a polynucleotide), means a molecule (e.g., polypeptide, protein or polynucleotide) isolated from its natural environment or prepared using synthetic methods such as those known to one of skill in the art. Complete purification is not required in either case. The molecules described herein can be isolated and purified from normally associated material in conventional ways, such that in the purified preparation the molecule is the predominant species in the preparation. At the very least, the degree of purification is such that extraneous material in the preparation does not interfere with use of the molecule in the manner disclosed herein. The molecule is at least about 85% pure; alternatively, at least about 90% pure, alternatively, at least about 95% pure; and alternatively, at least about 99% pure.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "mutant," when used in connection with a polypeptide or protein such as an enzyme, means a variant containing a substitution in one or more of the amino acid residues on the polypeptide or protein at the indicated position(s). Mutant also is used for a polynucleotide encoding such a mutant polypeptide or protein.

As used herein, "a position corresponding to" means the position of an amino acid residue in a query amino acid sequence that is aligned with the amino acid residue in a reference amino acid sequence using software such as AlignX of Vector NTI with default parameters (available from Invitrogen; see, Lu & Moriyama (2004) *Brief Bioinform.* 5:378-88). Thus, "amino acid (AA) residue at a position corresponding to the position Y of the amino acid sequence set forth in SEQ ID NO: X" means the AA residue in a query amino acid sequence that is aligned with AA Y of SEQ ID NO: X when the query amino acid sequence is aligned with SEQ ID NO: X using AlignX of Vector NTI with default parameters. It should be noted that the AA Y of SEQ ID NO: X itself is also encompassed by this term.

As used herein, "oxidase activity" or "Ox activity" means an enzymatic activity of the ChOx mutant to catalyze the oxidation of cholesterol to generate cholest-4-en-3-one by utilizing oxygen as an electron acceptor. The oxidase activity may be assayed by measuring the amount of generated hydrogen peroxide ($H_2O_2$) by any method known in the art such as, for example, by reagents for $H_2O_2$ detection such as 4AA/

TODB/POD (4-aminoantipyrine/N,N-bis(4-sulfobutyl)-3-methylaniline disodium salt/horseradish peroxidase) or by a platinum (Pt) electrode. In the context of the relative or quantitative activity, the oxidase activity is specifically defined to be the mole amount of the substrate (cholesterol) oxidized per unit time measured by the amount of generated $H_2O_2$ at about 25° C. in 10 mM PPB, pH 7.0, 1.5 mM TODB, 2 U/ml horseradish peroxidase (POD), and 1.5 mM 4-aminoantipyrine (4AA). The formation of quinoneimine dye may be measured spectrophotometrically at 546 nm.

As used herein, "dehydrogenase activity" or "Dh activity" means an enzymatic activity of the ChOx mutant to catalyze the oxidation of cholesterol to generate cholest-4-en-3-one by utilizing an electron mediator other than oxygen as an electron acceptor. The dehydrogenase activity may be assayed by measuring the amount of electron transferred to the mediator using, for example, mPMS/DCIP (1-methoxy-5-methylphenazinium methylsulfate/2,6-dichloroindophenol), cPES (trifluoro-acetate-1-(3-carboxy-propoxy)-5-ethyl-phenanzinium, NA BM31_1144 (N,N-bis-(hydroxyethyl)-3-methoxy-nitrosoaniline hydrochloride, NA BM31_1008 (N,N-bis-hydroxyethyl-4-nitrosoaniline) and N—N-4-dimethyl-nitrosoaniline. In the context of the relative or quantitative activity, the dehydrogenase activity is specifically defined to be the mole amount of the substrate (e.g., cholesterol) oxidized per unit time measured by the amount of electron transferred to the mediator at about 25° C. in 10 mM PPB (pH 7.0), 0.6 mM DCIP, and 6 mM methoxy PMS (mPMS).

The ChOx mutant therefore has a reduced oxidase activity when compared to a wild-type ChOx, while substantially retaining the dehydrogenase activity. The ChOx mutant can have an oxidase activity of about 50% or less when compared to the wild-type ChOx. Alternatively, the ChOx mutant has an oxidase activity of about 40% or less, about 30% or less, about 20% or less, or about 15% or less when compared to the wild-type ChOx.

In addition, the ChOx mutant can have a dehydrogenase activity of about 50% or more when compared to a wild-type ChOx. Alternatively, the ChOx mutant has a dehydrogenase activity of about 60% or more, about 70% or more, about 80% or more, about 90% or more, about 100% or more, or more than 100% or more when compared to the wild-type ChOx.

In the wild-type ChOx, the oxidase activity is about 300 times higher than the dehydrogenase activity. When dissolved oxygen is present in an assay system, electrons generated by oxidizing the substrate can be transferred to oxygen. Thus, the enzyme activity measured in the presence of an electron mediator will be greatly affected by the dissolved oxygen concentration. In contrast, the ChOx mutant as described herein has a ratio of dehydrogenase/oxidase activity of about 2.0 or more, about 4.0 or more, about 6.0 or more, about 8.0 or more, or about 10 or more. Since the dehydrogenase activity exceeds the oxidase activity, the enzyme activity of the ChOx mutant will be less affected by the dissolved oxygen concentration, which is advantageous in utilizing the ChOx mutant in a clinical diagnosis with a blood sample.

It should be understood that the numbering of the amino acid sequence for ChOx herein begins at an initial Met and that the claimed ChOx mutant may or may not have the signal peptide. Examples of amino acid sequences for the ChOx mutant include, but are not limited to, SEQ ID NOS. 1-48 modified at least at one of a position corresponding to position 159, 228 or 396 of SEQ ID NO: 1.

Cholesterol Oxidase Mutant-Encoding Polynucleotides: Another composition encompassing the inventive concept includes an isolated polynucleotide that encodes a ChOx mutant as described herein. An isolated polynucleotide has a structure that is not identical to that of any naturally occurring nucleic acid molecule or to that of any fragment of a naturally occurring genomic nucleic acid spanning more than one gene. An isolated polynucleotide also includes, without limitation, (a) a nucleic acid having a sequence of a naturally occurring genomic or extrachromosomal nucleic acid molecule, but which is not flanked by the coding sequences that flank the sequence in its natural position; (b) a nucleic acid incorporated into a vector or into a prokaryote or eukaryote host cell's genome such that the resulting polynucleotide is not identical to any naturally occurring vector or genomic DNA; (c) a separate molecule such as a cDNA, a genomic fragment, a fragment produced by polymerase chain reaction (PCR) or a restriction fragment; and (d) a recombinant nucleotide sequence that is part of a hybrid gene (i.e., a gene encoding a fusion protein). Specifically excluded from this definition are nucleic acids present in mixtures of clones, e.g., as these occur in a DNA library such as a cDNA or genomic DNA library. An isolated polynucleotide can be modified or unmodified DNA or RNA, whether fully or partially single-stranded or double-stranded or even triple-stranded. In addition, an isolated polynucleotide can be chemically or enzymatically modified and can include so-called non-standard bases such as inosine.

The nucleotide sequence of polynucleotides coding for ChOx may be readily obtained from public databases such as, for example, GenBank®, European Nucleotide Archive, DNA Databank of Japan, and Int'l Nucleotide Sequence Database Collaboration.

The polynucleotide encoding the wild-type ChOx may be cloned from the genome of respective organisms using PCR or other known techniques. Then, mutations may be introduced by techniques such as site-directed mutagenesis, PCR mutagenesis or any other known techniques. The amino acid residue to be mutated may be identified using any software for sequence alignment available in the art. Alternatively, polynucleotides coding for the ChOx mutant may be prepared by PCR using a series of chemically synthesized oligonucleotides, or fully synthesized. Examples of nucleotide sequences for the ChOx mutant can include, but are not limited to, those encoding an amino acid sequence as set forth in any one of SEQ ID NOS. 1-48 modified at least at one of a position corresponding to position 159, 228 or 396 of SEQ ID NO: 1.

Vectors and Host Cells: Other compositions encompassing the inventive concept include a vector having the ChOx mutant-encoding polynucleotide or a host cell expressing the vector. The ChOx mutant may be prepared by inserting a mutant polynucleotide into an appropriate expression vector and introducing the vector into an appropriate host cell, such as, for example, *Escherichia coli*. The transformant is cultured and the ChOx mutant expressed in the transformant may be collected from the cells or culture medium by any known technique.

The recombinant ChOx mutant thus obtained may be purified by any of the known purification techniques including, but not limited to, ion exchange column chromatography, affinity chromatography, liquid chromatography, filtration, ultrafiltration, salt precipitation, solvent precipitation, immunoprecipitation, gel electrophoresis, isoelectric electrophoresis and dialysis.

Thus, the inventive concept encompasses isolated or purified polypeptides, proteins and polynucleotides for a ChOx mutant, a vector comprising the polynucleotide encoding the ChOx mutant, a host cell transformed with such a vector, and a method for preparing the ChOx mutant by culturing the transformant, collecting and purifying the ChOx mutant from the culture.

Devices

In addition to the above compositions, the inventive concept encompasses various devices for assaying cholesterol, including HDL- or LDL-associated cholesterol, in a sample, where the device includes a ChOx mutant as described herein and optionally an electron mediator.

Biosensor Test Strips: One device encompassing the inventive concept includes biosensor test strips having at least the ChOx mutant as described herein as a reagent. The assay device may have a similar structure as any conventional, commercially available electrochemical (e.g., amperometric) biosensor test strip for monitoring the blood cholesterol level. One example of such a device has two electrodes (i.e., a working electrode and a reference or counter electrode) positioned on an insulating substrate, a reagent port and a sample receiver. The reagent port contains the ChOx mutant and the electron mediator.

When a sample, such as a blood sample, is added to the sample receiver, cholesterol contained in the sample will react with the ChOx mutant and the electron mediator to generate a current, which is indicative of the amount of cholesterol in the sample. Examples of electrochemical biosensors for determining enzyme substrate concentration are known in, for example, Int'l Patent Application Publication No. WO 2004/113900 and U.S. Pat. No. 5,997,817.

As an alternative to electrochemical biosensors, optical detection technologies might be used. Typically, such optical devices are based on color changes that occur in a reagent system comprising an enzyme, an electron mediator and an indicator. The color changes can be quantified using fluorescence, absorption or remission measurements. Examples of optical devices for determining enzyme substrate concentration are known in, for example, U.S. Pat. Nos. 7,008,799; 6,036,919 and 5,334,508.

Enzyme Electrodes: Another device encompassing the inventive concept includes an enzyme electrode having at least the ChOx mutant immobilized on the electrode.

Enzyme Sensors: Another device encompassing the inventive concept includes an enzyme sensor for assaying cholesterol having an enzyme electrode as described herein as a working electrode. The concentration of cholesterol in a sample may be determined by measuring the amount of electrons generated by the enzyme reaction. Various sensor systems are known in the art and include, but are not limited to, carbon (C) electrode, metal electrode and Pt electrode.

Here, the ChOx mutant can be immobilized on electrodes. Examples of means for immobilizing molecules such as the ChOx mutant include, but are not limited to, cross-linking, encapsulating into a macromolecular matrix, coating with a dialysis membrane, optical cross-linking polymer, electro-conductive polymer, oxidation-reduction polymer, and any combination thereof.

When the measurement is conducted in an amperometric system using a C electrode, gold (Au) electrode or Pt electrode provided with an immobilized enzyme is used as a working electrode, together with a counter electrode (such as a Pt electrode) and a reference electrode (such as a Ag/AgCl electrode). The electrodes can be inserted into a buffer containing a mediator and kept at predetermined temperature.

A predetermined voltage can be applied to the working electrode, and then a sample is added and an increased value in electric current is measured. Examples of the mediators for use in the assay include, but are not limited to, potassium ferricyanide, ferrocene, osmium derivative, ruthenium derivative, phenazine methosulfate, etc. It is generally also possible to use so-called two-electrode systems with one working electrode and one counter or pseudo-reference electrode.

Further, cholesterol may be assayed using an immobilized electron mediator in an amperometric system using a C electrode, Au electrode or Pt electrode. The enzyme, such as a ChOx mutant, can be immobilized on the electrode together with an electron mediator such as potassium ferricyanide, ferrocene, osmium derivative, or phenazine methosulfate in a macromolecular matrix by means of adsorption or covalent bond to prepare a working electrode.

The working electrode can be inserted into buffer together with a counter electrode (such as a Pt electrode) and a reference electrode (such as a Ag/AgCl electrode), and kept at a predetermined temperature. As indicated above, a predetermined voltage can be applied to the working electrode, and then the sample is added and increased value in electric current is measured.

It is to be understood that whenever this disclosure refers to cholesterol as an analyte other analytes that can be converted to cholesterol such as, for example, HDL-associated cholesterol or LDL-associated cholesterol, also shall be encompassed. One of skill in the art knows that a cholesterol esterase enzyme may be required to set free cholesterol from cholesterol esters that naturally occur in sample materials like blood or blood fractions.

Thus, the inventive concept encompasses biosensor test strips, electrodes and sensors including at least the ChOx mutant as described herein.

Kits

In addition to the above compositions and devices, the inventive concept encompasses kits for assaying cholesterol, as well as HDL- or LDL-associated cholesterol, in a sample, where the kits include at least a ChOx mutant as described herein and optionally an electron mediator.

Additionally, the kits can include a buffer necessary for the measurement, an appropriate electron mediator and, if necessary, further enzymes such as cholesterol esterase, a standard solution of cholesterol for preparing a calibration curve and an instruction for use. The ChOx mutant may be provided in various forms such as, for example, a freeze-dried reagent or a solution in an appropriate storage solution.

Any or all of the kit reagents can be provided within containers that protect them from the external environment, such as in sealed containers. Positive and/or negative controls can be included in the kits to validate the activity and correct usage of reagents employed in accordance with the inventive concept. Controls can include samples known to be either positive or negative for the presence of a predetermined concentration of cholesterol, HDL-associated cholesterol and/or LDL-associated cholesterol. The design and use of controls is standard and well within the routine capabilities of one of skill in the art.

Methods

In addition to the compositions, devices and kits, the inventive concept encompasses methods of assaying cholesterol, HDL-associated cholesterol and/or LDL-associated cholesterol in a sample.

The method can include at least a step of contacting the sample with the ChOx mutant and a step of measuring the amount of the cholesterol oxidized by the ChOx mutant as described above and further below.

EXAMPLES

The inventive concept will be more fully understood upon considering the following non-limiting examples, which are offered for purposes of illustration, not limitation.

Example 1

Plasmids Expressing ChOx of *Streptomyces* sp. Strain SA-COO pET28 ChOx_Nhis was used as a plasmid expressing ChOx of *Streptomyces* sp. strain SA-COO. This plasmid has a DNA fragment of the ChOx structural gene derived from *Streptomyces* sp. strain SA-COO, which is inserted in the NheI/HindIII cloning site of a vector pET28a. The ChOx gene in this plasmid is controlled by a T7 promoter. The pET28 ChOx_Nhis contains a kanamycin resistance gene.

Example 2

Mutagenesis of the ChOx Structural Gene Derived from *Streptomyces* sp. Strain SA-COO (1). Mutagenesis of Residues 159, 228 and 396.
The *Streptomyces* sp. strain SA-COO-derived ChOx structural gene contained in the pET28 ChOx_Nhis obtained in Example 1 was mutagenized so that Met at residue 159, Val at residue 228, and Phe at residue 396 in ChOx encoded by this gene were substituted by other amino acid residues.

Specifically, the codon (ATG) for Met at residue 159, the codon (GTT) for Val at residue 228, and the codon (TTT) for Phe at residue 396 in the ChOx structural gene contained in the plasmid pET28 ChOx_Nhis described in Example 1 were substituted by other amino acid codons using a commercially available site-directed mutagenesis kit (Stratagene Corp., QuikChange II Site-Directed Mutagenesis Kit).

The sequences of the forward and reverse primers used in the amino acid residue substitution are shown in the tables below. The number represents a position in the amino acid sequence containing the signal sequence of ChOx; the alphabet described before the number represents an amino acid residue before amino acid substitution; and the alphabet described after the number represents an amino acid residue after amino acid substitution. For example, M159A represents the substitution of Met at residue 159 to Ala.

In a PCR reaction, a reaction solution of the composition shown below was subjected to reaction at 95° C. for 30 seconds and then 15 repetitive cycles each involving 95° C. for 30 seconds, 55° C. for 1 minute and 68° C. for 8 minutes, followed by 68° C. for 30 minutes and then kept at 4° C.

Composition of Reaction Solution:

| | |
|---|---|
| Template DNA (5 ng/μL) | 2 μL |
| 10x reaction buffer | 5 μL |
| Forward primer (100 ng/μL) | 1.25 μL |
| Reverse primer (100 ng/μL) | 1.25 μL |
| dNTP | 1 μL |
| Distilled water | 38.5 μL |
| DNA polymerase | 1 μL |
| Total | 50 μL |

After the PCR reaction, 0.5 μL of DpnI was added to the reaction solution and incubated at 37° C. for 1 hour to degrade the template plasmid.

*E. coli* DH5α (supE44, ΔlacU169 (φ80lacZΔM15), hsdR17, recA1, endA1, gyrA96, thi-1, relA1) competent cells were transformed with the obtained reaction solution. From colonies grown on an LB agar medium (1% Bacto tryptone, 0.5% yeast extracts, 1% sodium chloride, 1.5% agar) containing kanamycin (50 μg/mL), plasmid DNA was prepared and sequenced to confirm that the mutation of interest was introduced in the ChOx structural gene.

The plasmid confirmed to have the introduced mutation was digested with restriction enzymes NheI and HindIII to excise the mutagenized ChOx structural gene, which was in turn inserted to a pET28a vector. DH5α was transformed with this plasmid, and a plasmid was extracted from the obtained colonies to obtain a ChOx mutant expression plasmid.

TABLE 1

Forward primer for M159.

| Amino acid substitution | Primer name | Sequence | SEQ ID NO |
|---|---|---|---|
| M159A | M159AFw | 5' GGTTAACGGTGGC<u>GCG</u>GCGGTGGAACCG 3' | 49 |
| M159C | M159CFw | 5' GGTTAACGGTGGC<u>TGC</u>GCGGTGGAACCG 3' | 50 |
| M159D | M159DFw | 5' GGTTAACGGTGGC<u>GAC</u>GCGGTGGAACCG 3' | 51 |
| M159E | M159EFw | 5' GGTTAACGGTGGC<u>GAA</u>GCGGTGGAACCG 3' | 52 |
| M159F | M159FFw | 5' GGTTAACGGTGGC<u>TTC</u>GCGGTGGAACCG 3' | 53 |
| M159G | M159GFw | 5' GGTTAACGGTGGC<u>GGT</u>GCGGTGGAACCG 3' | 54 |
| M159H | M159HFw | 5' GGTTAACGGTGGC<u>CAC</u>GCGGTGGAACCG 3' | 55 |
| M159I | M159IFw | 5' GGTTAACGGTGGC<u>ATC</u>GCGGTGGAACCG 3' | 56 |
| M159K | M159KFw | 5' GGTTAACGGTGGC<u>AAA</u>GCGGTGGAACCG 3' | 57 |
| M159L | M159LFw | 5' GGTTAACGGTGGC<u>CTG</u>GCGGTGGAACCG 3' | 58 |
| M159N | M159NFw | 5' GGTTAACGGTGGC<u>AAC</u>GCGGTGGAACCG 3' | 59 |

TABLE 1-continued

Forward primer for M159.

| Amino acid substitution | Primer name | Sequence | SEQ ID NO |
|---|---|---|---|
| M159P | M159PFw | 5' GGTTAACGGTGGCCCGGCGGTGGAACCG 3' | 60 |
| M159Q | M159QFw | 5' GGTTAACGGTGGCCAGGCGGTGGAACCG 3' | 61 |
| M159R | M159RFw | 5' GGTTAACGGTGGCTTCGCGGTGGAACCG 3' | 62 |
| M159S | M159SFw | 5' GGTTAACGGTGGCTCTGCGGTGGAACCG 3' | 63 |
| M159T | M159TFw | 5' GGTTAACGGTGGCACCGCGGTGGAACCG 3' | 64 |
| M159V | M159VFw | 5' GGTTAACGGTGGCGTTGCGGTGGAACCG 3' | 65 |
| M159W | M159WFw | 5' GGTTAACGGTGGCGGCGCGGTGGAACCG 3' | 66 |
| M159Y | M159YFw | 5' GGTTAACGGTGGCTACGCGGTGGAACCG 3' | 67 |

TABLE 2

Reverse primer for M159.

| Amino acid substitution | Primer name | Sequence | SEQ ID NO |
|---|---|---|---|
| M159A | M159ARv | 5' CGGTTCCACCGCCGCGCCACCGTTAACC 3' | 68 |
| M159C | M159CRv | 5' CGGTTCCACCGCGCAGCCACCGTTAACC 3' | 69 |
| M159D | M159DRv | 5' CGGTTCCACCGCGTCGCCACCGTTAACC 3' | 70 |
| M159E | M159ERv | 5' CGGTTCCACCGCTTCGCCACCGTTAACC 3' | 71 |
| M159F | M159FRv | 5' CGGTTCCACCGCGAAGCCACCGTTAACC 3' | 72 |
| M159G | M159GRv | 5' CGGTTCCACCGCACCGCCACCGTTAACC 3' | 73 |
| M159H | M159HRv | 5' CGGTTCCACCGCGTGGCCACCGTTAACC 3' | 74 |
| M159I | M159IRv | 5' CGGTTCCACCGCGATGCCACCGTTAACC 3' | 75 |
| M159K | M159KRv | 5' CGGTTCCACCGCTTTGCCACCGTTAACC 3' | 76 |
| M159L | M159LRv | 5' CGGTTCCACCGCCAGGCCACCGTTAACC 3' | 77 |
| M159N | M159NRv | 5' CGGTTCCACCGCGTTGCCACCGTTAACC 3' | 78 |
| M159P | M159PRv | 5' CGGTTCCACCGCCGGGCCACCGTTAACC 3' | 79 |
| M159Q | M159QRv | 5' CGGTTCCACCGCCTGGCCACCGTTAACC 3' | 80 |
| M159R | M159RRv | 5' CGGTTCCACCGCGAAGCCACCGTTAACC 3' | 81 |
| M159S | M159SRv | 5' CGGTTCCACCGCAGAGCCACCGTTAACC 3' | 82 |
| M159T | M159TRv | 5' CGGTTCCACCGCGGTGCCACCGTTAACC 3' | 83 |
| M159V | M159VRv | 5' CGGTTCCACCGCAACGCCACCGTTAACC 3' | 84 |
| M159W | M159WRv | 5' CGGTTCCACCGCGCCGCCACCGTTAACC 3' | 85 |
| M159Y | M159YRv | 5' GGTTCCACCGCGTAGCCACCGTTAACC 3' | 86 |

TABLE 3

Forward primer for V228.

| Amino acid substitution | Primer name | Sequence | SEQ ID NO |
|---|---|---|---|
| V228A | V228AFw | 5' GGGTACCGTGTTTGCGCCGAACGTGTATG 3' | 87 |
| V228C | V228CFw | 5' GGGTACCGTGTTTTGCCCGAACGTGTATG 3' | 88 |
| V228D | V228DFw | 5' GGGTACCGTGTTTGACCCGAACGTGTATG 3' | 89 |
| V228E | V228EFw | 5' GGGTACCGTGTTTGAACCGAACGTGTATG 3' | 90 |
| V228F | V228FFw | 5' GGGTACCGTGTTTTTCCCGAACGTGTATG 3' | 91 |
| V228G | V228GFw | 5' GGGTACCGTGTTTGGTCCGAACGTGTATG 3' | 92 |
| V228H | V228HFw | 5' GGGTACCGTGTTTCACCCGAACGTGTATG 3' | 93 |
| V228I | V228IFw | 5' GGGTACCGTGTTTATCCCGAACGTGTATG 3' | 94 |
| V228K | V228KFw | 5' GGGTACCGTGTTTAAACCGAACGTGTATG 3' | 95 |
| V228L | V228LFw | 5' GGGTACCGTGTTTCTGCCGAACGTGTATG 3' | 96 |
| V228M | V228MFw | 5' GGGTACCGTGTTTATGCCGAACGTGTATG 3' | 97 |
| V228N | V228NFw | 5' GGGTACCGTGTTTAACCCGAACGTGTATG 3' | 98 |
| V228P | V228PFw | 5' GGGTACCGTGTTTCCGCCGAACGTGTATG 3' | 99 |
| V228Q | V228QFw | 5' GGGTACCGTGTTTCAGCCGAACGTGTATG 3' | 100 |
| V228R | V228RFw | 5' GGGTACCGTGTTTTTCCCGAACGTGTATG 3' | 101 |
| V228S | V228SFw | 5' GGGTACCGTGTTTTCTCCGAACGTGTATG 3' | 102 |
| V228T | V228TFw | 5' GGGTACCGTGTTTACCCCGAACGTGTATG 3' | 103 |
| V228W | V228WFw | 5' GGGTACCGTGTTTGGCCCGAACGTGTATG 3' | 104 |
| V228Y | V228YFw | 5' GGGTACCGTGTTTTACCCGAACGTGTATG 3' | 105 |

TABLE 4

Reverse primer for V228.

| Amino acid substitution | Primer name | Sequence | SEQ ID NO |
|---|---|---|---|
| V228A | V228ARv | 5' CATACACGTTCGGCGCAAACACGGTACCC 3' | 106 |
| V228C | V228CRv | 5' CATACACGTTCGGGCAAAACACGGTACCC 3' | 107 |
| V228D | V228DRv | 5' CATACACGTTCGGGTCAAACACGGTACCC 3' | 108 |
| V228E | V228ERv | 5' CATACACGTTCGGTTCAAACACGGTACCC 3' | 109 |
| V228F | V228FRv | 5' CATACACGTTCGGACCAAACACGGTACCC 3' | 110 |
| V228G | V228GRv | 5' CATACACGTTCGGACCAAACACGGTACCC 3' | 111 |
| V228H | V228HRv | 5' CATACACGTTCGGGTGAAACACGGTACCC 3' | 112 |
| V228I | V228IRv | 5' CATACACGTTCGGGATAAACACGGTACCC 3' | 113 |
| V228K | V228KRv | 5' CATACACGTTCGGTTTAAACACGGTACCC 3' | 114 |
| V228L | V228LRv | 5' CATACACGTTCGGCAGAAACACGGTACCC 3' | 115 |
| V228M | V228MRv | 5' CATACACGTTCGGCATAAACACGGTACCC 3' | 116 |
| V228N | V228NRv | 5' CATACACGTTCGGGTTAAACACGGTACCC 3' | 117 |
| V228P | V228PRv | 5' CATACACGTTCGGCGGAAACACGGTACCC 3' | 118 |
| V228Q | V228QRv | 5' CATACACGTTCGGCTGAAACACGGTACCC 3' | 119 |

TABLE 4-continued

Reverse primer for V228.

| Amino acid substitution | Primer name | Sequence | SEQ ID NO |
|---|---|---|---|
| V228R | V228RRv | 5' CATACACGTTCGGGAAAAACACGGTACCC 3' | 120 |
| V228S | V228SRv | 5' CATACACGTTCGGAGAAAACACGGTACCC 3' | 121 |
| V228T | V228TRv | 5' CATACACGTTCGGGGTAAACACGGTACCC 3' | 122 |
| V228W | V228WRv | 5' CATACACGTTCGGGCCAAACACGGTACCC 3' | 123 |
| V228Y | V228YRv | 5' CATACACGTTCGGGTAAAACACGGTACCC 3' | 124 |

TABLE 5

Forward primer for F396.

| Amino acid substitution | Primer name | Sequence | SEQ ID NO |
|---|---|---|---|
| F396A | F396AFw | 5' GATAGCTCTGTTGCGGCCGAAATTGCACC 3' | 125 |
| F396C | F396CFw | 5' GATAGCTCTGTTTGCGCCGAAATTGCACC 3' | 126 |
| F396D | F396DFw | 5' GATAGCTCTGTTGACGCCGAAATTGCACC 3' | 127 |
| F396E | F396EFw | 5' GATAGCTCTGTTGAAGCCGAAATTGCACC 3' | 128 |
| F396G | F396GFw | 5' GATAGCTCTGTTGGTGCCGAAATTGCACC 3' | 129 |
| F396H | F396HFw | 5' GATAGCTCTGTTCACGCCGAAATTGCACC 3' | 130 |
| F396I | F396IFw | 5' GATAGCTCTGTTATCGCCGAAATTGCACC 3' | 131 |
| F396K | F396KFw | 5' GATAGCTCTGTTAAAGCCGAAATTGCACC 3' | 132 |
| F396L | F396LFw | 5' GATAGCTCTGTTCTGGCCGAAATTGCACC 3' | 133 |
| F396M | F396MFw | 5' GATAGCTCTGTTATGGCCGAAATTGCACC 3' | 134 |
| F396N | F396NFw | 5' GATAGCTCTGTTAACGCCGAAATTGCACC 3' | 135 |
| F396P | F396PFw | 5' GATAGCTCTGTTCCGGCCGAAATTGCACC 3' | 136 |
| F396Q | F396QFw | 5' GATAGCTCTGTTCAGGCCGAAATTGCACC 3' | 137 |
| F396R | F396RFw | 5' GATAGCTCTGTTTTCGCCGAAATTGCACC 3' | 138 |
| F396S | F396SFw | 5' GATAGCTCTGTTTCTGCCGAAATTGCACC 3' | 139 |
| F396T | F396TFw | 5' GATAGCTCTGTTACCGCCGAAATTGCACC 3' | 140 |
| F396V | F396VFw | 5' GATAGCTCTGTTGTTGCCGAAATTGCACC 3' | 141 |
| F396W | F396WFw | 5' GATAGCTCTGTTGGCGCCGAAATTGCACC 3' | 142 |
| F396Y | F396YFw | 5' GATAGCTCTGTTTACGCCGAAATTGCACC 3' | 143 |

TABLE 6

Reverse primer for F396.

| Amino acid substitution | Primer name | Sequence | SEQ ID NO |
|---|---|---|---|
| F396A | F396ARv | 5' GGTGCAATTTCGGCCGCAACAGAGCTATC 3' | 144 |
| F396C | F396CRv | 5' GGTGCAATTTCGGCGCAAACAGAGCTATC 3' | 145 |
| F396D | F396DRv | 5' GGTGCAATTTCGGCGTCAACAGAGCTATC 3' | 146 |
| F396E | F396ERv | 5' GGTGCAATTTCGGCTTCAACAGAGCTATC 3' | 147 |

TABLE 6-continued

Reverse primer for F396.

| Amino acid substitution | Primer name | Sequence | SEQ ID NO |
|---|---|---|---|
| F396G | F396GRv | 5' GGTGCAATTTCGGCACCAACAGAGCTATC 3' | 148 |
| F396H | F396HRv | 5' GGTGCAATTTCGGCGTGAACAGAGCTATC 3' | 149 |
| F396I | F396IRv | 5' GGTGCAATTTCGGCGATAACAGAGCTATC 3' | 150 |
| F396K | F396KRv | 5' GGTGCAATTTCGGCTTTAACAGAGCTATC 3' | 151 |
| F396L | F396LRv | 5' GGTGCAATTTCGGCCAGAACAGAGCTATC 3' | 152 |
| F396M | F396MRv | 5' GGTGCAATTTCGGCCATAACAGAGCTATC 3' | 153 |
| F396N | F396NRv | 5' GGTGCAATTTCGGCGTTAACAGAGCTATC 3' | 154 |
| F396P | F396PRv | 5' GGTGCAATTTCGGCCGGAACAGAGCTATC 3' | 155 |
| F396Q | F396QRv | 5' GGTGCAATTTCGGCCTGAACAGAGCTATC 3' | 156 |
| F396R | F396RRv | 5' GGTGCAATTTCGGCGAAAACAGAGCTATC 3' | 157 |
| F396S | F396SRv | 5' GGTGCAATTTCGGCAGAAACAGAGCTATC 3' | 158 |
| F396T | F396TRv | 5' GGTGCAATTTCGGCGGTAACAGAGCTATC 3' | 159 |
| F396V | F396VRv | 5' GGTGCAATTTCGGCAACAACAGAGCTATC 3' | 160 |
| F396W | F396WRv | 5' GGTGCAATTTCGGCGCCAACAGAGCTATC 3' | 161 |
| F396Y | F396YRv | 5' GGTGCAATTTCGGCGTAAACAGAGCTATC 3' | 162 |

Example 3

Analysis of Enzymatic Activity of ChOx Mutants

Methods:

Mutant ChOx was produced using the mutant ChOx expression plasmid obtained in Example 2, and studied for its enzymatic activity.

(1). Culture.

E. coli strain BL21 (DE3) was transformed with the wild-type ChOx expression plasmid prepared in Example 1 or the mutant ChOx expression plasmid prepared in Example 2. These transformants were separately shake-cultured at 37° C. for 12 hours in 3 mL of an LB medium (containing 50 µg/mL kanamycin) using an L-shaped tube. 1 mL each of these culture solutions was inoculated to a 500-mL Erlenmeyer flask with a baffle containing 100 mL of an LB medium (containing 50 µg/mL kanamycin) and gyratory-cultured at 37° C. At the point in time when $OD_{600}$ reached around 0.6, IPTG (isopropyl-β-D-thiogalactopyranoside) was added thereto at a final concentration of 1 mM, followed by culture at 20° C. for 24 hours.

(2). Preparation of Water-Soluble Fraction.

From the culture solution thus cultured, bacterial cells were collected and washed. Then, the obtained wet bacterial cells were suspended in a 10 mM potassium phosphate buffer (pH 7.0) and sonicated. Then, the homogenate was centrifuged at 17400×g at 4° C. for 20 minutes, and the supernatant was collected. This supernatant was further ultracentrifuged at 100400×g at 4° C. for 60 minutes, and the supernatant was collected. The obtained supernatant was dialyzed against a 10 mM potassium phosphate buffer (pH 7.0), and this was used as a water-soluble fraction. This water-soluble fraction was used as a ChOx sample to determine ChOx and cholesterol dehydrogenase (ChDH) activities for each of wild-type ChOx and mutant ChOx.

(3). Preparation of Substrate Solution.

Cholesterol powder was dissolved at a concentration of 100 mM in Triton X-100 and incubated at 80° C. to completely dissolve cholesterol. The 100 mM cholesterol solution was diluted 10-fold with pure water, cooled in running water, and brought to room temperature. Then, sodium cholate was added thereto at a final concentration of 3 mM to prepare a 10 mM cholesterol solution. For activity determination, the cholesterol solution was appropriately diluted with pure water to prepare various concentrations of substrate solutions.

(4). Determining ChOx Activity.

ChOx activity was determined by quantifying a change in absorbance at 546 nm over time derived from a dye generated using peroxidase, a Trinder reagent (TODB), and 4-aminoantipyrine from $H_2O_2$ generated through reaction with the substrate. The reaction was performed under conditions shown below.

The reaction was initiated by adding the substrate to a reaction solution (10 mM potassium phosphate buffer pH 7.0+1.5 mM 4-aminoantipyrine+1.5 mM TODB+2 U/ml peroxidase; all the concentrations are final concentrations) containing the enzyme solution, and change in absorbance at 546 nm was determined. Various concentrations of cholesterol were used as the substrate. The amount of an enzyme that forms 1 µmol $H_2O_2$ for 1 minute is defined as 1 U. 38 mM-1 cm$^{-1}$ was used as the molar absorption coefficient of TODB at pH 7.0. The formula for calculating an activity value from change in absorbance is shown below.

$$U/ml = \Delta ABS_{546}/min \times 2/38 \times 10$$

$$U/mg = U/ml/protein\ mg/ml$$

(5). Determining ChDh Activity.

ChDh activity was determined by quantifying a change in absorbance at 600 nm over time derived from the fading of DCIP reduced through reaction with the substrate. The reaction was performed under conditions shown below.

The reaction was initiated by adding the substrate to a reaction solution (10 mM potassium phosphate buffer pH 7.0+0.6 mM PMS+0.06 mM DCIP; all the concentrations are final concentrations) containing the enzyme solution, and change in absorbance at 600 nm was determined. Those used in the ChOx activity determination were used as the substrate. The amount of an enzyme that reduces 1 μmol DCIP is defined as 1 U. The activity value was calculated according to the formula shown below. 16.3 mM-1 cm$^{-1}$ was used as the molar absorption coefficient of DCIP at pH 7.0.

$$U/ml = \Delta ABS_{600}/min \times 1/16.3 \times 5$$

$$U/mg = U/ml/protein\ mg/ml$$

The results of activity determination of the wild-type ChOx and the mutant ChOx are shown in Tables 7-9.

Results:

The oxidase activities of all M159 mutant enzymes were largely reduced. Among them, M159F, M159L and M159V had dehydrogenase activity improved to 1.7 to 2.9 times the wild-type. Particularly, M159F had an oxidase activity value of $2.0 \times 10^{-2}$ U/mg and a dehydrogenase activity value of $2.2 \times 10^{-2}$ U/mg, which was 2.9 times the wild-type. The ratio of the dehydrogenase activity to the oxidase activity was 0.28% in the wild-type, whereas this ratio was 110% in M159F, which was improved to approximately 390 times the wild-type.

The oxidase activities of all the V228 mutant enzymes were lower than the wild-type (2.7 U/mg). The mutant that exhibited the lowest activity was V228D ($2.0 \times 10^{-4}$ U/mg). This value was approximately 1/10000 of the wild-type, showing significantly reduced reactivity to oxygen. In addition to V228D, V228N, V228Q, V228S and V228K exhibited an oxidase activity value as low as 1% or less of the wild-type (V228N, $7.0 \times 10^{-3}$ U/mg; V228E: $5.0 \times 10^{-3}$ U/mg; V228S: $9.0 \times 10^{-3}$ U/mg; and V228K: $8.8 \times 10^{-3}$ U/mg). On the other hand, the Val228 mutants having substitution to Ile, Leu or Phe, including V228A, had a relatively high oxidase activity value (ratio to wild-type: 10%-) and thus retained reactivity to oxygen (V228I: 2.2 U/mg; V228L: $9.4 \times 10^{-1}$ U/mg; V228F: $2.2 \times 10^{-1}$ U/mg).

Eight mutants were obtained that had a dehydrogenase activity improved when compared with the wild-type. Among them, V228T exhibited activity ($5.6 \times 10^{-2}$ U/mg) approximately five times the wild-type. In addition, the mutants having substitution to Lys, Ser or Cys exhibited high dehydrogenase activity (V228K: $3.4 \times 10^{-2}$ U/mg; V228C: $3.1 \times 10^{-2}$ U/mg; V228S: $2.0 \times 10^{-2}$ U/mg). On the other hand, the mutants having substitution to Leu or Ile had activity reduced to 1/10 of the wild-type (V228L: $1.0 \times 10^{-3}$ U/mg; V228I: $1.0 \times 10^{-3}$ U/mg). On the other hand, V228D and V228R had no detectable dehydrogenase activity.

The oxidase activities of the F396 mutant enzymes were reduced. The F396W mutant enzyme had an oxidase activity value of $1.2 \times 10^{-1}$ U/mg and a dehydrogenase activity value of $2.0 \times 10^{-2}$ U/mg. The oxidase activity was reduced compared with that of the wild-type ChOx, and the dehydrogenase activity was improved to twice or more the wild-type. The ratio of the dehydrogenase activity to the oxidase activity was 16%, which was 57 times the wild-type (0.28%). F396N and F396D had not only oxidase activity reduced to 1.9% and 0.032%, respectively, of the wild-type, but also dehydrogenase activity reduced to 23% and 14%, respectively, of the wild-type. Each of the mutant enzymes F396M, F396L, F396V, F396I and F396Y maintained oxidase activity (30% to 80% of the wild-type) when compared with the other mutant enzymes.

TABLE 7

| | Ox activity (U/mg) | Dh activity (U/mg) | Dh/Ox (%) |
|---|---|---|---|
| WT | 2.8 (100%) | $7.7 \times 10^{-3}$ (100%) | 0.28 |
| M159A | $3.6 \times 10^{-2}$ (1.3%) | $6.4 \times 10^{-3}$ (83%) | 18 |
| M159C | $2.1 \times 10^{-2}$ (0.75%) | $7.7 \times 10^{-3}$ (100%) | 37 |
| M159D | $7.4 \times 10^{-4}$ (0.026%) | $1.6 \times 10^{-3}$ (21%) | 220 |
| M159E | $4.4 \times 10^{-4}$ (0.016%) | $1.0 \times 10^{-3}$ (13%) | 230 |
| M159F | $2.0 \times 10^{-2}$ (0.71%) | $2.2 \times 10^{-2}$ (290%) | 110 |
| M159G | $1.4 \times 10^{-3}$ (0.05%) | $1.0 \times 10^{-3}$ (13%) | 71 |
| M159H | $6.2 \times 10^{-3}$ (0.22%) | $7.6 \times 10^{-4}$ (9.9%) | 12 |
| M159I | $3.1 \times 10^{-1}$ (11%) | $6.4 \times 10^{-3}$ (83%) | 2.1 |
| M159K | $6.0 \times 10^{-4}$ (0.021%) | $3.0 \times 10^{-3}$ (39%) | 500 |
| M159L | $5.0 \times 10^{-1}$ (18%) | $1.6 \times 10^{-2}$ (210%) | 3.2 |
| M159N | $5.2 \times 10^{-2}$ (1.9%) | $4.2 \times 10^{-4}$ (5.5%) | 0.81 |
| M159P | $1.9 \times 10^{-3}$ (0.068%) | $4.0 \times 10^{-4}$ (5.2%) | 21 |
| M159Q | $3.1 \times 10^{-2}$ (1.1%) | $5.0 \times 10^{-3}$ (65%) | 16 |
| M159R | $1.5 \times 10^{-4}$ (0.0054%) | $4.8 \times 10^{-4}$ (6.2%) | 320 |
| M159S | $1.8 \times 10^{-1}$ (6.4%) | $2.9 \times 10^{-3}$ (38%) | 1.6 |
| M159T | $2.9 \times 10^{-1}$ (10%) | $2.9 \times 10^{-3}$ (38%) | 1 |
| M159V | $4.7 \times 10^{-2}$ (1.7%) | $1.3 \times 10^{-2}$ (170%) | 28 |
| M159W | $2.3 \times 10^{-2}$ (0.82%) | $3.8 \times 10^{-4}$ (4.9%) | 1.7 |
| M159Y | $7.7 \times 10^{-3}$ (0.28%) | $5.0 \times 10^{-3}$ (65%) | 65 |

*n.d. = not detected

TABLE 8

| | Ox activity (U/mg) | Dh activity (U/mg) | Dh/Ox (%) |
|---|---|---|---|
| WT | 2.5-2.9 | $7.0 \times 10^{-3}$-$10 \times 10^{-3}$ | 0.25-0.35 |
| V228A | $3.0 \times 10^{-2}$-$4.3 \times 10^{-2}$ | $5.7 \times 10^{-2}$-$7.4 \times 10^{-2}$ | 150-180 |
| V228C | $7.0 \times 10^{-2}$ | $3.1 \times 10^{-2}$ | 44 |
| V228D | $2.0 \times 10^{-4}$ | n.d | — |
| V228E | $5.0 \times 10^{-3}$ | $1.4 \times 10^{-2}$ | 280 |
| V228F | $2.2 \times 10^{-1}$ | $5.0 \times 10^{-3}$ | 2.3 |
| V228G | $8.0 \times 10^{-3}$ | $1.8 \times 10^{-2}$ | 225 |
| V228H | $1.0 \times 10^{-2}$ | $6.0 \times 10^{-3}$ | 60 |
| V228I | 2.2 | $1.0 \times 10^{-3}$ | 0.06 |
| V228K | $8.8 \times 10^{-3}$ | $3.4 \times 10^{-2}$ | 374 |
| V228L | $9.4 \times 10^{-1}$ | $1.0 \times 10^{-3}$ | 0.1 |
| V228M | $2.2 \times 10^{-1}$ | $6.0 \times 10^{-4}$ | 0.27 |
| V228N | $7.0 \times 10^{-3}$ | $9.0 \times 10^{-3}$ | 130 |
| V228P | $4.8 \times 10^{-2}$ | $1.2 \times 10^{-2}$ | 25 |
| V228Q | $2.9 \times 10^{-2}$ | $6.7 \times 10^{-3}$ | 23 |
| V228R | $2.2 \times 10^{-3}$ | n.d. | — |
| V228S | $9.0 \times 10^{-3}$ | $2.0 \times 10^{-2}$ | 222 |
| V228T | $1.7 \times 10^{-1}$ | $5.6 \times 10^{-2}$ | 33 |
| V228W | $4.9 \times 10^{-2}$ | $6.2 \times 10^{-3}$ | 13 |
| V228Y | $1.2 \times 10^{-1}$ | $1.3 \times 10^{-2}$ | 110 |

TABLE 9

| | Ox activity (U/mg) | Dh activity (U/mg) | Dh/Ox (%) |
|---|---|---|---|
| WT | 2.8 (100%) | $7.7 \times 10^{-3}$ (100%) | 0.28 |
| F396A | $5.9 \times 10^{-2}$ (2.1%) | $1.8 \times 10^{-3}$ (23%) | 3.1 |
| F396C | $2.2 \times 10^{-1}$ (7.9%) | $2.3 \times 10^{-3}$ (30%) | 1.0 |
| F396D | $8.9 \times 10^{-4}$ (0.032%) | $1.1 \times 10^{-3}$ (14%) | 120 |
| F396E | $2.5 \times 10^{-3}$ (0.089%) | n.d. | — |
| F396G | $4.9 \times 10^{-1}$ (18%) | $8.3 \times 10^{-4}$ (11%) | 0.17 |
| F396H | $5.8 \times 10^{-2}$ (2.1%) | $1.5 \times 10^{-3}$ (19%) | 2.6 |
| F396I | $9.7 \times 10^{-1}$ (35%) | $2.3 \times 10^{-3}$ (30%) | 0.24 |
| F396K | $8.9 \times 10^{-2}$ (3.2%) | $3.0 \times 10^{-3}$ (39%) | 3.4 |
| F396L | 1.1 (39%) | $2.6 \times 10^{-3}$ (34%) | 0.24 |
| F396M | $8.4 \times 10^{-1}$ (30%) | $5.9 \times 10^{-3}$ (77%) | 0.70 |
| F396N | $5.3 \times 10^{-2}$ (1.9%) | $1.8 \times 10^{-3}$ (23%) | 3.4 |
| F396P | $2.1 \times 10^{-4}$ (0.0075%) | n.d. | — |
| F396Q | $9.6 \times 10^{-4}$ (0.034%) | n.d. | — |
| F396R | $3.3 \times 10^{-3}$ (0.12%) | n.d. | — |
| F396S | $8.5 \times 10^{-2}$ (3.0%) | $4.1 \times 10^{-3}$ (53%) | 2.7 |
| F396T | $1.9 \times 10^{-1}$ (6.8%) | $3.1 \times 10^{-3}$ (40%) | 1.7 |

TABLE 9-continued

|  | Ox activity (U/mg) | Dh activity (U/mg) | Dh/Ox (%) |
|---|---|---|---|
| F396V | $7.6 \times 10^{-1}$ (27%) | $2.4 \times 10^{-3}$ (31%) | 0.32 |
| F396W | $1.2 \times 10^{-1}$ (4.3%) | $2.0 \times 10^{-2}$ (260%) | 16 |
| F396Y | 1.7 (61%) | $9.1 \times 10^{-3}$ (120%) | 0.54 |

Tables 10-12 show alignments of the amino acid sequences that are annotated to be ChOx's. The entire sequences of these ChOx mutants are set forth in SEQ ID NOs: 1-48. Alignment was created using the AlignX application of Vector NTI suite 6.0. One of skill in the art will appreciate that other alignment software programs such as Blast will provide the same or substantially the same alignment.

It is evident from Table 10 that Met159 of SEQ ID NO:1 is conserved among the amino acid sequences listed in Table 10. Accordingly, one of skill in the art can easily identify the Met or Ile residue corresponding to the Met159 of SEQ ID NO:1 within the conserved region using any of commercially available software programs for sequence alignment, and understand that a ChOx mutant is easily prepared by introducing modification on that Met or Ile residue.

TABLE 10

| Origin* | Position of mutation | | | SEQ ID NO** |
|---|---|---|---|---|
| sp\|P12676 | M159 | 149 | VGGGSLVNGGMAVEPKRSYFE 169 | 1 |
| gb\|ABS32193 | M155 | 145 | VGGGSLVNGGMAVAPKRSYFE 165 | 2 |
| ref\|NP_821583 | M160 | 150 | VGGGSLVNGGMAVTPRRGYFE 170 | 3 |
| emb\|CAC20926 | M162 | 152 | VGGGSLVNGGMAVVPKRSYFE 172 | 4 |
| gb\|ADX66466 | M165 | 155 | VGGGSLVNGGMAVVPKRSYFE 175 | 5 |
| gb\|AAR16516 | M162 | 152 | VGGGSLVNGGMAVVPKRSYFE 172 | 6 |
| gb\|AAZ66744 | M165 | 155 | VGGGSLVNGGMAVVPKRAYFE 175 | 7 |
| gb\|AAA69655 | M160 | 150 | VGGGSLVNGGMAVTPRRSYFQ 170 | 8 |
| ref\|ZP_07282326 | M157 | 147 | VGGGSLVNGAMAVQPKRSYFE 167 | 9 |
| ref\|ZP_07286354 | M165 | 155 | VGGGSLVNGGMAPTPRRSYFA 175 | 10 |
| ref\|ZP_04998002 | M166 | 156 | VGGGSLVNGGMSPTPRRSYFS 176 | 11 |
| ref\|YP_003492288 | M154 | 144 | VGGGSLVNGSMAVTPLRSYFA 164 | 12 |
| gb\|ADI09201 | M158 | 148 | VGGGSLVNGGMAVTPSRAYFQ 168 | 13 |
| ref\|ZP_07603147 | I164 | 154 | VGGGSLVNGGIAVTPSRSYFQ 174 | 14 |
| ref\|YP_003512290 | M148 | 138 | VGGGSLVNGGMAVVPRRKYFQ 158 | 15 |
| ref\|ZP_05008217 | M154 | 144 | VGGGSLVNGGMAVTPPRPYFS 164 | 16 |
| ref\|ZP_06770826 | M168 | 158 | VGGGSLVNGGMAVTPPRPYFS 178 | 17 |
| ref\|ZP_06566730 | M151 | 141 | VGGGSLVNGGMAVTPRRGYFE 161 | 18 |
| ref\|NP_827244 | M159 | 149 | VGGGSLVNGGMAVTPLQSYFA 169 | 19 |
| ref\|YP_001108512 | M139 | 129 | VGGGSLVNGGMAVTPRRGYFE 149 | 20 |
| ref\|ZP_07292951 | I161 | 151 | VGGGSLVNGGIAVTPPRAYFQ 171 | 21 |
| ref\|ZP_07303187 | M159 | 149 | VGGGSLVNGGMAVTPLRSYFA 169 | 22 |
| ref\|ZP_01689718 | M146 | 136 | VGGGSLVNGGMAVTPPMNYFQ 156 | 23 |
| ref\|YP_003384280 | M157 | 147 | VGGGSLVNGGMAPTPRRSYFE 167 | 24 |
| ref\|ZP_06916507 | M159 | 149 | VGGGSLVNGSMAVTPLQSYFA 169 | 25 |
| ref\|YP_003134867 | M150 | 140 | VGGGSLVNGAMAVTPKRATFA 160 | 26 |
| emb\|CAC44897 | M167 | 157 | VGGGSLVNGGMAVTPKRNYFE 177 | 27 |
| pdb\|1COY_A | M122 | 112 | VGGGSLVNGGMAVTPKRNYFE 132 | 28 |
| sp\|P22637 | M167 | 157 | VGGGSLVNGGMAVTPKRNYFE 177 | 29 |
| ref\|ZP_06830857 | M167 | 157 | VGGGSLVNGGMAVTPKRNYFE 177 | 30 |
| gb\|ABC75776 | M167 | 157 | VGGGSLVNGGMAVTPKRNYFE 177 | 31 |

TABLE 10-continued

| Origin* | Position of mutation | | SEQ ID NO** |
|---|---|---|---|
| gb\|ABG24169 | M167 | 157 VGGGSLVNGGMAVTPKRNYFE 177 | 32 |
| emb\|CAZ68116 | M158 | 148 VGGGSLVNGGMAVTPKRNYFE 168 | 33 |
| ref\|YP_002764459 | M167 | 157 VGGGSLVNGGMAVTPKRNYFE 177 | 34 |
| ref\|ZP_04388109 | M137 | 127 VGGGSLVNGGMAVTPKRNYFE 147 | 35 |
| ref\|YP_003769621 | M142 | 132 VGGGSLVNGGMAVTPKRENFG 152 | 36 |
| ref\|YP_003339891 | M166 | 156 VGGGSLVNGGMAVTPKRENFG 176 | 37 |
| ref\|ZP_07290670 | M168 | 158 VGGGSLVNGGMAVTPKRQNFA 178 | 38 |
| ref\|YP_003116660 | M165 | 155 IGGGSLVNGGMAVTPKQENFG 175 | 39 |
| ref\|ZP_06588880 | M169 | 159 VGGGSLVNGGMAVTPRRENFG 179 | 40 |
| ref\|ZP_04697978 | M121 | 111 VGGGSLVNGGMAVTPRRENFG 131 | 41 |
| ref\|ZP_06276136 | M166 | 156 VGGGSLVNGGMAVTPRRENFG 176 | 42 |
| ref\|YP_001821989 | M166 | 156 VGGGSLVNGGMAVTPRRENFG 176 | 43 |
| ref\|ZP_05002034 | M165 | 155 VGGGSLVNGGMAVTPKRERFG 175 | 44 |
| ref\|ZP_06907496 | M166 | 156 VGGGSLVNGGMAVTPRRENFG 176 | 45 |
| ref\|YP_003100211 | M163 | 153 VGGGSLVNGGMAVTPRRERFA 173 | 46 |
| ref\|ZP_07085639 | M142 | 132 VGGGSLVNGGMAVTPKESYFR 152 | 47 |
| gb\|ADX68765 | M139 | 129 VGGGSLVNGGMAVLPKKNYFK 149 | 48 |

*Databases: gb: GenBank; sp: Swissprot; ref: RefSeq; emb: EMBL; pdb: Protein Data Bank
**SEQ ID NOs represent the full-length sequence It is evident from Table 11 that Val228 of SEQ ID NO:1 is conserved among the amino acid sequences listed in Table 11. Accordingly, one of skill in the art can easily identify the Val, Met or Ile residue corresponding to the Val228 of SEQ ID NO:1 within the conserved region using any of commercially available software programs for sequence alignment, and understand that a ChOx mutant is easily prepared by introducing modification on that Val, Met or Ile residue.

TABLE 11

| Origin* | Position of mutation | | SEQ ID NO** |
|---|---|---|---|
| sp\|P12676 | V228 | 218 AGKAGLGTVFVPNVYDFGYMQ 238 | 1 |
| gb\|ABS32193 | V224 | 214 AQKAGLGTVHVPNVYDFDHMR 234 | 2 |
| ref\|NP_821583 | V229 | 219 ASNAGLSTTFVPNVYDWDYMR 239 | 3 |
| emb\|CAC20926 | V231 | 221 AGKAGLGTTFVPNVYDFDYMR 241 | 4 |
| gb\|ADX66466 | V234 | 224 AGKAGLSTTFVPNVYDFDYMR 244 | 5 |
| gb\|AAR16516 | V231 | 221 AGKAGLSTTFVPNVYDFDHMR 241 | 6 |
| gb\|AAZ66744 | V234 | 224 ASKAGLGTTFVPNVYDFGHMR 244 | 7 |
| gb\|AAA69655 | V229 | 219 AENAGLKTTFVPNVYDWDYMR 239 | 8 |
| ref\|ZP_07282326 | V226 | 216 AQKTGLKTTFVPSVYDFEYMK 236 | 9 |
| ref\|ZP_07286354 | V234 | 224 AQNTGLKTTFVPNVYDFGYMK 244 | 10 |
| ref\|ZP_04998002 | V235 | 225 AQNTGLKTVFVPNVYDFEYMK 245 | 11 |
| ref\|YP_003492288 | V223 | 213 AAKAGLRTTFVPSVYDFDHMQ 233 | 12 |
| gb\|ADI09201 | V227 | 217 AKTAGLKTVFVPNVYDFDYMQ 237 | 13 |
| ref\|ZP_07603147 | M233 | 223 AARAGLKTVFMPNVYDFDYMR 243 | 14 |

TABLE 11-continued

| Origin* | Position of mutation | | SEQ ID NO** |
|---|---|---|---|
| ref\|YP_003512290 | V217 | 207 AEETGLATTF<u>V</u>PNVYDFDHMA 227 | 15 |
| ref\|ZP_05008217 | V223 | 213 AARAGLGTVF<u>V</u>PNVYDFDYMR 233 | 16 |
| ref\|ZP_06770826 | V237 | 227 AARAGLGTVF<u>V</u>PNVYDFDYMR 247 | 17 |
| ref\|ZP_06566730 | V220 | 210 AQRAGLRTTF<u>V</u>PNVYDFGYMR 230 | 18 |
| ref\|NP_827244 | V228 | 218 ATNTGLKTTF<u>V</u>PNVYDFGYMQ 238 | 19 |
| ref\|YP_001108512 | V208 | 198 AQRAGLRTTF<u>V</u>PNVYDFGYMR 218 | 20 |
| ref\|ZP_07292951 | V230 | 220 ASAAGLKTVF<u>V</u>PSVYDFDYMR 240 | 21 |
| ref\|ZP_07303187 | V228 | 218 ADNAGLKTTF<u>V</u>PNVYDFGHME 238 | 22 |
| ref\|ZP_01689718 | V215 | 205 AEKAGFKTVT<u>V</u>PNIYDYNYMQ 225 | 23 |
| ref\|YP_003384280 | I226 | 216 AHQAGFRTAV<u>I</u>PNVYDFGYLE 236 | 24 |
| ref\|ZP_06916507 | V228 | 218 AQNTGLKTTF<u>V</u>PSVYDFGYMQ 238 | 25 |
| ref\|YP_003134867 | V219 | 209 AHNAGLTTTF<u>V</u>PSVYDFARMR 229 | 26 |
| emb\|CAC44897 | V236 | 226 AQRSGFTTAF<u>V</u>PNVYDFEYMK 246 | 27 |
| pdb\|1COY_A | V191 | 181 AQRSGFTTAF<u>V</u>PNVYDFEYMK 201 | 28 |
| sp\|P22637 | V236 | 226 AQRSGFTTAF<u>V</u>PNVYDFEYMK 246 | 29 |
| ref\|ZP_06830857 | V236 | 226 AQRSGFTTAF<u>V</u>PNVYDFEYMK 246 | 30 |
| gb\|ABC75776 | V236 | 226 AQRSGFTTAF<u>V</u>PNVYDFEYMK 246 | 31 |
| gb\|ABG24169 | V236 | 226 AQRSGFTTAF<u>V</u>PNVYDFEYMK 246 | 32 |
| emb\|CAZ68116 | V227 | 217 AQRSGFTTAF<u>V</u>PNVYDFEYMK 237 | 33 |
| ref\|YP_002764459 | V236 | 226 AERSGYTTTF<u>V</u>PNVYDFNYMK 246 | 34 |
| ref\|ZP_04388109 | V206 | 196 AERSGYTTTF<u>V</u>PNVYDFNYMK 216 | 35 |
| ref\|YP_003769621 | V211 | 201 AQRSGFPFVF<u>V</u>PDVYDWDYME 221 | 36 |
| ref\|YP_003339891 | V235 | 225 AQRSGFPFVF<u>V</u>PDVYDWDYMK 245 | 37 |
| ref\|ZP_07290670 | V237 | 227 AQRSGFPFVF<u>V</u>PDVYDWDYMK 247 | 38 |
| ref\|YP_003116660 | V234 | 224 AGRSGFPFQF<u>V</u>PDVYDWNYMQ 244 | 39 |
| ref\|ZP_06588880 | V238 | 228 AQRSGFPFLF<u>V</u>PAVYDWDYMK 248 | 40 |
| ref\|ZP_04697978 | V190 | 180 AQRSGFPFLF<u>V</u>PAVYDWDYMK 200 | 41 |
| ref\|ZP_06276136 | V235 | 225 AQRSGFPFLF<u>V</u>PAVYDWDYMK 245 | 42 |
| ref\|YP_001821989 | V235 | 225 AQRSGFPFLF<u>V</u>PAVYDWDYMK 245 | 43 |
| ref\|ZP_05002034 | V234 | 224 AQRSGFPFVF<u>V</u>PNVYDWEYMK 244 | 44 |
| ref\|ZP_06907496 | V235 | 225 AERSGFPFVL<u>V</u>PGVYDWDYLE 245 | 45 |
| ref\|YP_003100211 | V232 | 222 AQRSGFPFEL<u>V</u>PGVYDWAHLE 242 | 46 |
| ref\|ZP_07085639 | V211 | 201 AHKAGFKTIR<u>V</u>PNVYDFKYME 221 | 47 |
| gb\|ADX68765 | V208 | 198 AQKAGYKTIR<u>V</u>PNVYNFKYME 218 | 48 |

*Databases: gb: GenBank; sp: Swissprot; ref: RefSeq; emb: EMBL; pdb: Protein Data Bank
**SEQ ID NOs represent the full-length sequence It is evident from Table 12 that Phe396 of SEQ ID NO:1 is conserved among the amino acid sequences listed in Table 12. Accordingly, one of skill in the art can easily identify the Phe residue corresponding to the Phe396 of SEQ ID NO:1 within the conserved region using any of commercially available software programs for sequence alignment, and understand that a ChOx mutant is easily prepared by introducing modification on that Phe residue.

TABLE 12

| Origin* | Position of mutation | | SEQ ID NO** |
|---|---|---|---|
| sp\|P12676 | F396 | 386 DAWDN----SDSSV<u>F</u>AEIAPMPAGL 406 | 1 |
| gb\|ABS32193 | F392 | 382 DDWDN----PQNPV<u>F</u>AEIAPMPAGL 402 | 2 |
| ref\|NP_821583 | F397 | 387 DDWDN----PDTPV<u>F</u>AEIAPLPAGV 407 | 3 |
| emb\|CAC20926 | F399 | 389 DDWNN----PTAPV<u>F</u>AEIAPMPAGL 409 | 4 |
| gb\|ADX66466 | F402 | 392 DDWDN----PAAPV<u>F</u>AEIAPMPAGL 412 | 5 |
| gb\|AAR16516 | F399 | 389 DDWDN----PAAPV<u>F</u>AEIAPMPAGL 409 | 6 |
| gb\|AAZ66744 | F402 | 392 DDWNN----AAAPV<u>F</u>AEIAPMPAGA 412 | 7 |
| gb\|AAA69655 | F397 | 387 DDWDN----PDNPV<u>F</u>AEIAPMPAGL 407 | 8 |
| ref\|ZP_07282326 | F394 | 384 DDWDN----PAHPV<u>F</u>AEIAPVPAGL 404 | 9 |
| ref\|ZP_07286354 | F402 | 392 DDWDN----AANPV<u>F</u>AEIAPLPMGI 412 | 10 |
| ref\|ZP_04998002 | F403 | 393 DDWDN----AANPV<u>F</u>AEIAPLPMGF 413 | 11 |
| ref\|YP_003492288 | F391 | 381 DDWAN----TANPV<u>F</u>AEIAPLPTGL 401 | 12 |
| gb\|ADI09201 | F395 | 385 DDWSN----ATNPV<u>F</u>AEIAPLPAGT 405 | 13 |
| ref\|ZP_07603147 | F401 | 391 DDWSN----TANPV<u>F</u>AEIAPLPAGL 411 | 14 |
| ref\|YP_003512290 | F385 | 375 DDWDN----EAARV<u>F</u>AEIAPVPAGF 395 | 15 |
| ref\|ZP_05008217 | F397 | 387 DDWNN----PTHPV<u>F</u>AEIAPLPMGL 407 | 16 |
| ref\|ZP_06770826 | F411 | 401 DDWNN----PTHPV<u>F</u>AEIAPLPMGL 421 | 17 |
| ref\|ZP_06566730 | F388 | 378 DNWDD----PVHPV<u>F</u>AEIAPLPAGL 398 | 18 |
| ref\|NP_827244 | F396 | 386 DDWAN----TSNPV<u>F</u>AEIAPLPMGL 406 | 19 |
| ref\|YP_001108512 | F376 | 366 DNWDD----PVHPV<u>F</u>AEIAPLPAGL 386 | 20 |
| ref\|ZP_07292951 | F398 | 388 DDWSN----AANPV<u>F</u>AEIAPLPAGT 408 | 21 |
| ref\|ZP_07303187 | F396 | 386 DDWAN----TANPV<u>F</u>AEIAPLPMGL 406 | 22 |
| ref\|ZP_01689718 | F383 | 373 NDWDN----ASNPV<u>F</u>AEIAPLPTGF 393 | 23 |
| ref\|YP_003384280 | F393 | 383 DNWDD----PVHPA<u>F</u>AEIAPLPTGL 403 | 24 |
| ref\|ZP_06916507 | F396 | 386 DDWAN----TDNPV<u>F</u>AEIAPLPTGL 406 | 25 |
| ref\|YP_003134867 | F387 | 377 DAWDD----PRHPV<u>F</u>AEVAPMPAGV 397 | 26 |
| emb\|CAC44897 | F404 | 394 DNWAD----PTAPI<u>F</u>AEIAPLPAGL 414 | 27 |
| pdb\|1COY_A | F359 | 349 DNWAD----PTAPI<u>F</u>AEIAPLPAGL 369 | 28 |
| sp\|P22637 | F404 | 394 DNWAD----PTAPI<u>F</u>AEIAPLPAGL 414 | 29 |
| ref\|ZP_06830857 | F404 | 394 DNWAD----PTAPI<u>F</u>AEIAPLPAGL 414 | 30 |
| gb\|ABC75776 | F404 | 394 DNWAD----PAAPI<u>F</u>AEIAPLPAGL 414 | 31 |
| gb\|ABG24169 | F405 | 395 DNWAD----PTAPI<u>F</u>AEIAPLPAGL 415 | 32 |
| emb\|CAZ68116 | F395 | 385 DNWAD----PTAPI<u>F</u>AEIAPLPAGL 405 | 33 |
| ref\|YP_002764459 | F405 | 395 DNWAD----TSAPV<u>F</u>AEIAPFPAGT 415 | 34 |
| ref\|ZP_04388109 | F375 | 365 DNWAD----TSAPV<u>F</u>AEIAPFPAGT 385 | 35 |
| ref\|YP_003769621 | F377 | 369 DNWAA----GGA--<u>F</u>AEVAPLPTGI 387 | 36 |

TABLE 12-continued

| Origin* | Position of mutation | | SEQ ID NO** |
|---|---|---|---|
| ref\|YP_003339891 | F401 | 393 DNWAA----GGA--<u>F</u>AEVAPLPTGI 411 | 37 |
| ref\|ZP_07290670 | F403 | 395 DNWDA----GGA--<u>F</u>AEVAPLPTGI 413 | 38 |
| ref\|YP_003116660 | F400 | 392 DNWTK----GGA--<u>F</u>AEVAPLPIGI 410 | 39 |
| ref\|ZP_06588880 | F404 | 396 DNWDA----GGA--<u>F</u>AEIAPLPTGI 414 | 40 |
| ref\|ZP_04697978 | F356 | 348 DNWDA----GGA--<u>F</u>AEIAPLPTGI 366 | 41 |
| ref\|ZP_06276136 | F401 | 393 DNWDA----GGA--<u>F</u>AEVAPLPTGI 411 | 42 |
| ref\|YP_001821989 | F401 | 393 DNWDA----GGA--<u>F</u>AEVAPLPTGI 411 | 43 |
| ref\|ZP_05002034 | F400 | 392 DNWDA----GGA--<u>F</u>AEVAPLPTGI 410 | 44 |
| ref\|ZP_06907496 | F401 | 393 DNWQA----GGA--<u>F</u>AEVAPLPTGI 411 | 45 |
| ref\|YP_003100211 | F397 | 389 DNWAA----GGA--<u>F</u>AEVAPLPTGV 407 | 46 |
| ref\|ZP_07085639 | F380 | 370 DNWDD----PEHQF<u>F</u>TEIAPLPMGM 390 | 47 |
| gb\|ADX68765 | F377 | 367 DNWDD----PKYPF<u>F</u>AEIAPLPMGM 387 | 48 |

*Databases: gb: GenBank; sp: Swissprot; ref: RefSeq; emb: EMBL; pdb: Protein Data Bank
**SEQ ID NOs represent the full-length sequence All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A cholesterol oxidase mutant modified at one or more amino acid positions selected from:
 (a). a position corresponding to position 159 of SEQ ID NO: 1 by substituting the amino acid residue Met with an amino acid residue selected from the group consisting of Phe, Leu, Val, Cys, Ile, Ala, Gln, Tyr, Lys, and Ser or by substituting the amino acid residue Ile with an amino acid residue selected from the group consisting of Phe, Leu, Val, Cys, Ala, Gln, Tyr, Lys and Ser;
 (b). a position corresponding to position 228 of SEQ ID NO: 1 by substituting the amino acid residue Val, Met or Ile with an amino acid residue selected from the group consisting of Ala, Thr, Lys, Cys, Ser, Gly, Glu, Tyr, Pro, Asn, Gln, Trp and His; and
 (c). a position corresponding to position 396 of SEQ ID NO: 1 by substituting the amino acid residue Phe with an amino acid residue selected from the group consisting of Trp, Ser, Thr, Lys, Ala, Asn, His and Asp,
 wherein the cholesterol oxidase mutant has at least about 95% sequence identity to any one of SEQ ID NOS: 1-5.

2. The cholesterol oxidase mutant of claim 1, wherein the cholesterol oxidase mutant has a reduced oxidase activity when compared to a wild-type cholesterol oxidase.

3. The cholesterol oxidase mutant of claim 1, wherein cholesterol oxidase mutant has an oxidase activity that is less than its dehydrogenase activity.

4. The cholesterol oxidase mutant of claim 1, wherein the cholesterol oxidase mutant has a dehydrogenase activity of about 50% or more of a wild-type cholesterol oxidase.

5. A cholesterol oxidase mutant comprising an amino acid sequence selected from the group consisting of SEQ ID NOs: 1-5 modified at one or more positions corresponding to position 159, 228 or 369 of SEQ ID NO: 1, wherein the cholesterol oxidase mutant has a reduced oxidase activity when compared to a wild-type cholesterol oxidase.

6. An isolated polynucleotide encoding the cholesterol oxidase mutant of claim 1.

7. A vector comprising the polynucleotide of claim 6.

8. An isolated host cell transformed with the vector of claim 7.

9. A method of assaying cholesterol in a sample, the method comprising the steps of:
 contacting the sample with a cholesterol oxidase mutant modified at one or more amino acid positions selected from:
 (a). a position corresponding to position 159 of SEQ ID NO: 1 by substituting the amino acid residue Met with an amino acid residue selected from the group consisting of Phe, Leu, Val, Cys, Ile, Ala, Gln, Tyr, Lys, and Ser or by substituting the amino acid residue Ile with an amino acid residue selected from the group consisting of Phe, Leu, Val, Cys, Ala, Gln, Tyr, Lys and Ser, (b). a position corresponding to position 228 of SEQ ID NO: 1 by substituting the amino acid residue Val, Met or Ile with an amino acid residue selected from the group consisting of Ala, Thr, Lys, Cys, Ser, Gly, Glu, Tyr, Pro, Asn, Gln, Trp and His, and (c). a position corresponding to position 396 of SEQ ID NO: 1 by substituting the amino acid residue Phe with an amino acid residue selected from the group consisting of Trp, Ser, Thr, Lys, Ala, Asn, His and Asp; and measuring an amount of the cholesterol oxidized by the cholesterol oxidase, wherein the cholesterol oxidase mutant has at least 95% sequence identity to any one of SEQ ID NOS: 1-5.

10. A method of assaying HDL-associated cholesterol in a sample, the method comprising the steps of:

contacting the sample with the cholesterol oxidase mutant of claim 1, wherein the cholesterol is obtained from HDL-associated cholesterol prior to the contacting; and measuring an amount of oxidized cholesterol.

11. A method for assaying LDL-associated cholesterol in a sample, the method comprising the steps of:

contacting the sample with the cholesterol oxidase mutant of claim 1, wherein the cholesterol is obtained from LDL-associated cholesterol prior to the contacting; and measuring the amount of oxidized cholesterol.

12. A device for assaying cholesterol, HDL-associated cholesterol and/or LDL-associated cholesterol in a sample, the device comprising:

the cholesterol oxidase mutant of claim 1; and an electron mediator.

13. A kit for assaying cholesterol, HDL-associated cholesterol and/or LDL-associated cholesterol in a sample, the kit comprising:

the cholesterol oxidase mutant of claim 1; and an electron mediator.

14. An enzyme electrode comprising the cholesterol oxidase mutant of claim 1 immobilized on an electrode.

15. An enzyme sensor for assaying cholesterol, HDL-associated cholesterol and/or LDL-associated cholesterol comprising the enzyme electrode of claim 14 as a working electrode.

* * * * *

SEQUENCE LISTING

```
<160> NUMBER OF SEQ ID NOS: 162

<210> SEQ ID NO 1
<211> LENGTH: 546
<212> TYPE: PRT
<213> ORGANISM: Streptomyces sp.
<220> FEATURE:
<221> NAME/KEY: MISC_FEATURE
<222> LOCATION: (159)..(159)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (228)..(228)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (396)..(396)
<223> OTHER INFORMATION: Xaa is Phe, Trp, Ser, Thr, Lys, Ala, Asn, His
      or Asp, provided that when Xaa159 is Met, then Xaa396 is not Phe

<400> SEQUENCE: 1

Met Thr Ala Gln Gln His Leu Ser Arg Arg Arg Met Leu Gly Met Ala
1               5                   10                  15

Ala Phe Gly Ala Ala Ala Leu Ala Gly Gly Thr Thr Ile Ala Ala Pro
            20                  25                  30

Arg Ala Ala Ala Ala Ala Lys Ser Ala Ala Asp Asn Gly Gly Tyr Val
        35                  40                  45

Pro Ala Val Val Ile Gly Thr Gly Tyr Gly Ala Ala Val Ser Ala Leu
    50                  55                  60
```

```
Arg Leu Gly Glu Ala Gly Val Gln Thr Leu Met Leu Glu Met Gly Gln
 65                  70                  75                  80

Leu Trp Asn Gln Pro Gly Pro Asp Gly Asn Ile Phe Cys Gly Met Leu
                 85                  90                  95

Asn Pro Asp Lys Arg Ser Ser Trp Phe Lys Asn Arg Thr Glu Ala Pro
            100                 105                 110

Leu Gly Ser Phe Leu Trp Leu Asp Val Val Asn Arg Asn Ile Asp Pro
        115                 120                 125

Tyr Ala Gly Val Leu Asp Arg Val Asn Tyr Asp Gln Met Ser Val Tyr
    130                 135                 140

Val Gly Arg Gly Val Gly Gly Ser Leu Val Asn Gly Gly Xaa Ala
145                 150                 155                 160

Val Glu Pro Lys Arg Ser Tyr Phe Glu Glu Ile Leu Pro Arg Val Asp
            165                 170                 175

Ser Ser Glu Met Tyr Asp Arg Tyr Phe Pro Arg Ala Asn Ser Met Leu
        180                 185                 190

Arg Val Asn His Ile Asp Thr Lys Trp Phe Glu Asp Thr Glu Trp Tyr
    195                 200                 205

Lys Phe Ala Arg Val Ser Arg Glu Gln Ala Gly Lys Ala Gly Leu Gly
    210                 215                 220

Thr Val Phe Xaa Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
            245                 250                 255

Gly Asn Asn His Gly Lys Gln Ser Leu Asp Lys Thr Tyr Leu Ala Ala
        260                 265                 270

Ala Leu Gly Thr Gly Lys Val Thr Ile Gln Thr Leu His Gln Val Lys
    275                 280                 285

Thr Ile Arg Gln Thr Lys Asp Gly Gly Tyr Ala Leu Thr Val Glu Gln
    290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
            325                 330                 335

Arg Ala Arg Asp Thr Gly Thr Leu Pro Asn Leu Asn Ser Glu Val Gly
        340                 345                 350

Ala Gly Trp Gly Pro Asn Gly Asn Ile Met Thr Ala Arg Ala Asn His
    355                 360                 365

Met Trp Asn Pro Thr Gly Ala His Gln Ser Ser Ile Pro Ala Leu Gly
    370                 375                 380

Ile Asp Ala Trp Asp Asn Ser Asp Ser Ser Val Xaa Ala Glu Ile Ala
385                 390                 395                 400

Pro Met Pro Ala Gly Leu Glu Thr Trp Val Ser Leu Tyr Leu Ala Ile
            405                 410                 415

Thr Lys Asn Pro Gln Arg Gly Thr Phe Val Tyr Asp Ala Ala Thr Asp
        420                 425                 430

Arg Ala Lys Leu Asn Trp Thr Arg Asp Gln Asn Ala Pro Ala Val Asn
    435                 440                 445

Ala Ala Lys Ala Leu Phe Asp Arg Ile Asn Lys Ala Asn Gly Thr Ile
    450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
```

```
                        485                 490                 495
Asp Tyr Gly Arg Val Ala Gly Tyr Lys Asn Leu Tyr Val Thr Asp Gly
            500                 505                 510

Ser Leu Ile Pro Gly Ser Val Gly Val Asn Pro Phe Val Thr Ile Thr
            515                 520                 525

Ala Leu Ala Glu Arg Asn Val Glu Arg Ile Ile Lys Gln Asp Val Thr
            530                 535                 540

Ala Ser
545

<210> SEQ ID NO 2
<211> LENGTH: 542
<212> TYPE: PRT
<213> ORGANISM: Streptomyces virginiae
<220> FEATURE:
<221> NAME/KEY: MISC_FEATURE
<222> LOCATION: (155)..(155)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (224)..(224)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (392)..(392)
<223> OTHER INFORMATION: Xaa is Phe, Trp, Ser, Thr, Lys, Ala, Asn, His
      or Asp, provided that when Xaa155 is Met, then Xaa392 is not Phe

<400> SEQUENCE: 2

Met Glu Gln His Leu Ser Arg Arg Leu Leu Gly Met Thr Ala Leu
1               5                   10                  15

Gly Ala Ala Ala Leu Ala Gly Ser Thr Thr Ile Gly Ala Pro Arg Ala
            20                  25                  30

Leu Ala Ala Asp Arg Ala Asp Gly Val Ala Phe Phe Pro Ala Val Val
            35                  40                  45

Ile Gly Thr Gly Tyr Gly Ala Ala Val Ser Ala Leu Arg Leu Gly Glu
    50                  55                  60

Ala Gly Val Arg Thr Val Met Leu Glu Met Gly Gln Leu Trp Asn Gln
65                  70                  75                  80

Pro Gly Pro Asp Gly Asn Val Phe Ala Gly Met Leu Lys Pro Asp Lys
                85                  90                  95

Arg Ser Ser Trp Phe Lys Asn Arg Thr Glu Ala Pro Leu Gly Ser Phe
            100                 105                 110

Leu Trp Leu Asp Leu Ala Asn Arg Asp Ile Asp Pro Tyr Ala Gly Val
            115                 120                 125

Leu Asp Arg Val Asn Phe Asp Gln Met Ser Val Tyr Val Gly Arg Gly
            130                 135                 140

Val Gly Gly Gly Ser Leu Val Asn Gly Gly Xaa Ala Val Ala Pro Lys
145                 150                 155                 160

Arg Ser Tyr Phe Glu Glu Val Leu Pro Arg Val Asp Ser Ala Glu Met
            165                 170                 175

Tyr Ser Arg Tyr Phe Pro Arg Ala Asn Ser Met Leu Arg Val Asn His
            180                 185                 190

Ile Asp Asp Gly Trp Phe Glu Ser Thr Glu Trp Tyr Lys Phe Ala Arg
    195                 200                 205

Val Ser Arg Asp Gln Ala Gln Lys Ala Gly Leu Gly Thr Val His Xaa
    210                 215                 220
```

```
Pro Asn Val Tyr Asp Phe Asp His Met Arg Arg Glu Ala Ala Gly Glu
225                 230                 235                 240

Ala Pro Lys Ser Ala Leu Ala Gly Glu Val Ile Tyr Gly Asn Asn His
            245                 250                 255

Gly Lys Gln Ser Leu Asp Lys Thr Tyr Leu Ala Ala Ala Leu Gly Thr
        260                 265                 270

Gly Lys Val Thr Ile Glu Thr Leu His Gln Ala Arg Thr Ile Arg Gln
    275                 280                 285

Gln Lys Asp Gly Thr Tyr Leu Leu Thr Val Glu Gln Arg Asp Ala Asp
290                 295                 300

Gly Arg Leu Leu Ala Thr Lys Glu Ile Ser Cys Arg His Leu Phe Leu
305                 310                 315                 320

Gly Ala Gly Ser Leu Gly Ser Thr Glu Leu Leu Arg Ala Arg Glu
            325                 330                 335

Thr Gly Thr Leu Pro Asp Leu Ser Ser Glu Ile Gly Ala Gly Trp Gly
            340                 345                 350

Pro Asn Gly Asn Ile Met Thr Ala Arg Ala Asn His Val Trp Asn Pro
            355                 360                 365

Thr Gly Ala Asn Gln Ser Ser Ile Pro Ala Leu Gly Ile Asp Asp Trp
        370                 375                 380

Asp Asn Pro Gln Asn Pro Val Xaa Ala Glu Ile Ala Pro Met Pro Ala
385                 390                 395                 400

Gly Leu Glu Thr Trp Val Ser Leu Tyr Leu Ala Ile Thr Lys Asn Pro
                405                 410                 415

Glu Arg Gly Thr Phe Ala Tyr Asp Ala Ala Thr Asp Arg Ala Ala Leu
            420                 425                 430

Arg Trp Thr Arg Asp Gln Asn Thr Pro Ala Val Ser Ala Ala Lys Ser
        435                 440                 445

Leu Phe Asp Arg Ile Asn Lys Ala Asn Thr Thr Met Tyr Arg Tyr Asp
465                 455                 460

Leu Phe Gly Lys Gln Leu Lys Ala Phe Ser Asp Asp Phe Thr Tyr His
465                 470                 475                 480

Pro Leu Gly Gly Cys Val Leu Gly Arg Ala Thr Asp Asp Tyr Gly Arg
            485                 490                 495

Val Lys Gly Tyr Lys Asn Leu Tyr Val Thr Asp Gly Ser Leu Ile Pro
        500                 505                 510

Gly Ser Ile Gly Val Asn Pro Phe Val Thr Ile Thr Ala Leu Ala Glu
    515                 520                 525

Arg Asn Ile Glu Arg Val Ile Arg Gln Asp Val Thr Ala Ala
530                 535                 540

<210> SEQ ID NO 3
<211> LENGTH: 547
<212> TYPE: PRT
<213> ORGANISM: Streptomyces avermitilis
<220> FEATURE:
<221> NAME/KEY: MISC_FEATURE
<222> LOCATION: (160)..(160)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (229)..(229)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (397)..(397)
<223> OTHER INFORMATION: Xaa is Phe, Trp, Ser, Thr, Lys, Ala, Asn, His
``` or Asp, provided that when Xaa160 is Met, then Xaa397 is not Phe

<400> SEQUENCE: 3

```
Met Ile Ala His Gln Pro Leu Ser Arg Arg Met Leu Gly Val Ala
1               5                   10                  15

Ala Leu Gly Ala Ala Leu Ala Gly Gln Thr Thr Ile Thr Ala Ala
            20                  25                  30

Pro Arg Ala Ala Ala Thr Ala Thr Ser Gly Ser Gly Gly Thr Phe
        35                  40                  45

Val Pro Ala Val Val Gly Thr Gly Tyr Gly Ala Ala Val Ser Ala
    50                  55                  60

Leu Arg Leu Gly Glu Ala Gly Val Pro Thr Leu Met Leu Glu Met Gly
65                  70                  75                  80

Arg Leu Trp Asn Gln Pro Gly Pro Asp Gly Asn Val Phe Ser Gly Met
                85                  90                  95

Leu Lys Pro Asp Lys Arg Ser Ser Trp Phe Lys Thr Arg Thr Glu Ala
            100                 105                 110

Pro Leu Gly Ser Phe Leu Trp Leu Asp Leu Ala Asn Arg Asp Ile Glu
        115                 120                 125

Pro Tyr Ala Gly Val Leu Asp Arg Val Asn Phe Asp Gln Met Ser Val
    130                 135                 140

Tyr Leu Gly Arg Gly Val Gly Gly Ser Leu Val Asn Gly Gly Xaa
145                 150                 155                 160

Ala Val Thr Pro Arg Arg Ser Tyr Phe Glu Glu Val Leu Pro Gln Val
                165                 170                 175

Asp Ala Glu Glu Met Tyr Thr Lys Tyr Phe Pro Arg Ala Asn Ser Thr
            180                 185                 190

Leu Arg Val Asn Asn Ile Asp Lys Ser Trp Phe Glu Gln Thr Asp Trp
        195                 200                 205

Tyr Ser Phe Ala Arg Val Ser Arg Arg Gln Ala Ser Asn Ala Gly Leu
    210                 215                 220

Ser Thr Thr Phe Xaa Pro Asn Val Tyr Asp Trp Asp Tyr Met Arg Arg
225                 230                 235                 240

Glu Ala Asp Gly Ala Val Pro Lys Ser Ala Leu Ala Ala Glu Val Ile
                245                 250                 255

Tyr Gly Asn Asn His Gly Lys Val Ser Leu Asp Lys Ser Tyr Leu Ala
            260                 265                 270

Ala Ala Leu Gly Thr Gly Lys Val Thr Ile Glu Thr Leu His Gln Val
        275                 280                 285

Lys Thr Ile Arg Gln Gln Asn Asp Gly Thr Tyr Leu Leu Thr Val Glu
    290                 295                 300

Gln Arg Asp Thr Gly Gly Lys Leu Leu Gly Thr Lys Glu Val Ser Cys
305                 310                 315                 320

Arg His Leu Phe Leu Gly Ala Gly Ser Leu Gly Ser Thr Glu Leu Leu
                325                 330                 335

Leu Arg Ala Arg Glu Thr Gly Thr Leu Pro Gly Leu Ser Pro Glu Val
            340                 345                 350

Gly Gly Gly Trp Gly Pro Asn Gly Asn Ile Met Thr Ala Arg Ala Asn
        355                 360                 365

His Met Trp Asn Pro Thr Gly Thr Lys Gln Ser Ser Ile Pro Ala Leu
    370                 375                 380

Gly Ile Asp Asp Trp Asp Asn Pro Asp Thr Pro Val Xaa Ala Glu Ile
385                 390                 395                 400
```

-continued

```
Ala Pro Leu Pro Ala Gly Val Glu Thr Trp Val Ser Leu Tyr Leu Ala
            405                 410                 415

Ile Thr Lys Asn Pro Glu Arg Gly Thr Phe Val Tyr Asp Ala Ala Lys
        420                 425                 430

Asp Arg Ala Asp Leu Arg Trp Thr Arg Asp Gln Asn Ala Pro Ala Ile
        435                 440                 445

Ala Ala Ala Lys Ser Leu Phe Asp Arg Ile Asn Lys Ala Asn Ala Thr
    450                 455                 460

Ile Tyr Arg Tyr Asp Leu Phe Gly Lys Gln Ile Lys Ala Phe Ala Asp
465                 470                 475                 480

Asp Phe Cys Tyr His Pro Leu Gly Gly Cys Val Leu Gly Lys Ala Thr
                485                 490                 495

Asp Asp Tyr Gly Arg Val Thr Gly Tyr Lys Asn Leu Tyr Val Thr Asp
                500                 505                 510

Gly Ser Leu Ile Pro Gly Ser Ile Gly Val Asn Pro Phe Val Thr Ile
            515                 520                 525

Ala Ala Leu Ala Glu Arg Asn Ile Glu Arg Val Ile Lys Gln Asp Ile
        530                 535                 540

Ala Asp Ser
545

<210> SEQ ID NO 4
<211> LENGTH: 549
<212> TYPE: PRT
<213> ORGANISM: Streptomyces natalensis
<220> FEATURE:
<221> NAME/KEY: MISC_FEATURE
<222> LOCATION: (162)..(162)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (231)..(231)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (399)..(399)
<223> OTHER INFORMATION: Xaa is Phe, Trp, Ser, Thr, Lys, Ala, Asn, His
      or Asp, provided that when Xaa162 is Met, then Xaa399 is not Phe

<400> SEQUENCE: 4

Met Phe Glu Asn Gln His Leu Ser Arg Arg Leu Leu Gly Leu Ala
1               5                   10                  15

Ala Leu Gly Gly Ala Ala Ala Ala Gly Met Thr Thr Ile Thr Ser Ala
            20                  25                  30

Pro His Ala Ala Ala Ala Asp Arg Arg Ser Pro Gln Ala Arg Ser Gly
        35                  40                  45

Ser Phe Val Pro Ala Val Val Ile Gly Thr Gly Tyr Gly Ala Ala Val
    50                  55                  60

Ser Ala Leu Arg Leu Gly Glu Ala Gly Ile Pro Thr Leu Met Leu Glu
65                  70                  75                  80

Met Gly Gln Leu Trp Asn Lys Pro Ala Asp Asp Gly Asn Val Phe Cys
                85                  90                  95

Gly Met Leu Ser Pro Asp Arg Arg Ser Ser Trp Phe Lys Ser Arg Thr
            100                 105                 110

Glu Ala Pro Leu Gly Ser Phe Leu Trp Leu Asp Val Ile Asn Arg Asp
        115                 120                 125

Ile Asp Pro Tyr Ala Gly Val Leu Asp Lys Val His Phe Asp Gln Met
    130                 135                 140
```

```
Ser Val Tyr Val Gly Arg Gly Val Gly Gly Ser Leu Val Asn Gly
145                 150                 155                 160

Gly Xaa Ala Val Val Pro Lys Arg Ser Tyr Phe Glu Val Leu Pro
            165                 170                 175

Arg Val Asp Ala Ala Glu Met Tyr Asp Arg Tyr Phe Pro Arg Ala Asn
        180                 185                 190

Ser Met Leu Lys Val Asn His Ile Asp Lys Gly Trp Phe Glu Glu Thr
        195                 200                 205

Glu Trp Tyr Lys Phe Ala Arg Val Ser Arg Glu Gln Ala Gly Lys Ala
    210                 215                 220

Gly Leu Gly Thr Thr Phe Xaa Pro Asn Val Tyr Asp Phe Asp Tyr Met
225                 230                 235                 240

Arg Arg Glu Ala Asn Gly Glu Ser Pro Lys Ser Ala Leu Ala Thr Glu
                245                 250                 255

Val Ile Tyr Gly Asn Asn His Gly Lys Gln Ser Leu Asp Lys Thr Tyr
            260                 265                 270

Leu Ala Ala Ala Leu Gly Thr Gly Lys Val Thr Ile Glu Thr Leu His
        275                 280                 285

Gln Val Arg Ala Ile His Gln Gln Pro Asp Gly Ser Tyr Val Leu Ser
    290                 295                 300

Val Asp Gln Ile Asp Thr Ala Gly Gln Thr Val Ala His Lys Glu Ile
305                 310                 315                 320

Ser Cys Arg His Leu Phe Leu Gly Ala Gly Ser Leu Gly Ser Thr Glu
                325                 330                 335

Leu Leu Val Arg Ala Arg Asp Thr Gly Ala Leu Pro Asp Leu Asn Ala
            340                 345                 350

Glu Val Gly Ala Gly Trp Gly Pro Asn Gly Asn Ile Met Thr Gly Arg
        355                 360                 365

Ala Asn His Val Trp Asn Pro Thr Gly Ala His Gln Ser Ser Ile Pro
370                 375                 380

Ala Leu Gly Ile Asp Asp Trp Asn Asn Pro Thr Ala Pro Val Xaa Ala
385                 390                 395                 400

Glu Ile Ala Pro Met Pro Ala Gly Leu Glu Thr Trp Val Ser Leu Tyr
                405                 410                 415

Leu Ala Ile Thr Lys Asn Pro Glu Arg Gly Thr Phe Tyr Tyr Asp Lys
            420                 425                 430

Ala Thr Asp Arg Ala Ala Leu Arg Trp Thr Arg Asp Gln Asn Thr Pro
        435                 440                 445

Ala Val Asn Ala Ala Arg Ser Leu Phe Asp Arg Ile Asn Lys Ala Asn
        450                 455                 460

Gly Thr Met Tyr Arg Tyr Asp Leu Phe Gly Pro Gln Leu Lys Asn Phe
465                 470                 475                 480

Ser Asp Asp Phe Cys Tyr His Pro Leu Gly Gly Cys Val Leu Gly Lys
                485                 490                 495

Ala Thr Asp Gly Tyr Gly Arg Val Ala Gly Tyr His Asn Leu Tyr Val
            500                 505                 510

Thr Asp Gly Ala Leu Ile Pro Gly Ser Ile Gly Val Asn Pro Phe Val
        515                 520                 525

Thr Ile Thr Ala Leu Ala Glu Arg Asn Ile Glu Arg Ile Ile Ala Glu
        530                 535                 540

Asp Val Lys Ala Ala
545
```

```
<210> SEQ ID NO 5
<211> LENGTH: 552
<212> TYPE: PRT
<213> ORGANISM: Streptomyces chattanoogenesis
<220> FEATURE:
<221> NAME/KEY: MISC_FEATURE
<222> LOCATION: (165)..(165)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (234)..(234)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (402)..(402)
<223> OTHER INFORMATION: Xaa is Phe, Trp, Ser, Thr, Lys, Ala, Asn, His
      or Asp, provided that when Xaa165 is Met, then Xaa402 is not Phe

<400> SEQUENCE: 5

Met Phe Glu Asn Gln Gln Asn Gln His Leu Ser Arg Arg Arg Leu Leu
 1               5                  10                  15

Gly Leu Ala Ala Leu Ser Gly Ala Ala Val Ala Gly Met Thr Thr Ile
             20                  25                  30

Ser Ala Ala Pro Arg Ala Ala Ala Asp Lys Arg Ser Pro Lys Ala
         35                  40                  45

Gly Ser Gly Ser Phe Val Pro Ala Val Val Ile Gly Thr Gly Tyr Gly
     50                  55                  60

Ala Ala Val Ser Ala Leu Arg Leu Gly Glu Ala Gly Ile Pro Thr Leu
65                  70                  75                  80

Met Leu Glu Met Gly Gln Leu Trp Asn Lys Pro Ala Asp Asp Gly Asn
                 85                  90                  95

Val Phe Cys Gly Met Leu Lys Pro Asp Arg Arg Ser Ser Trp Phe Lys
            100                 105                 110

Ser Arg Thr Glu Ala Pro Leu Gly Ser Phe Leu Trp Leu Asp Val Ile
        115                 120                 125

Asn Arg Asp Ile Asp Pro Tyr Ala Gly Val Leu Asp Lys Val His Phe
    130                 135                 140

Asp Gln Met Ser Val Tyr Val Gly Arg Gly Val Gly Gly Gly Ser Leu
145                 150                 155                 160

Val Asn Gly Gly Xaa Ala Val Val Pro Lys Arg Ser Tyr Phe Glu Glu
                165                 170                 175

Val Leu Pro Arg Val Asp Ala Ala Glu Met Tyr Asp Arg Tyr Phe Pro
            180                 185                 190

Arg Ala Asn Ser Met Leu Lys Val Asn His Ile Asp Lys Gly Trp Phe
        195                 200                 205

Glu Glu Thr Glu Trp Tyr Lys Phe Ala Arg Val Ser Arg Glu Gln Ala
    210                 215                 220

Gly Lys Ala Gly Leu Ser Thr Thr Phe Xaa Pro Asn Val Tyr Asp Phe
225                 230                 235                 240

Asp Tyr Met Arg Arg Glu Ala Asn Gly Glu Ser Pro Lys Ser Ala Leu
                245                 250                 255

Ala Thr Glu Val Ile Tyr Gly Asn Asn His Gly Lys Gln Ser Leu Asp
            260                 265                 270

Lys Thr Tyr Leu Ala Ala Ala Leu Gly Thr Gly Lys Val Thr Ile Glu
        275                 280                 285

Thr Leu His Gln Val Lys Ala Ile His Gln Gln Pro Asp Gly Ser Tyr
    290                 295                 300
```

```
Val Leu Ser Val Asp Gln Ile Asp Thr Ala Gly Gln Thr Val Ala His
305                 310                 315                 320

Lys Glu Ile Ala Cys Arg His Leu Phe Leu Gly Ala Gly Ser Leu Gly
            325                 330                 335

Ser Thr Glu Leu Leu Val Arg Ala Arg Asp Thr Gly Ala Leu Pro Asp
        340                 345                 350

Leu Asn Ala Glu Val Gly Ala Gly Trp Gly Pro Asn Gly Asn Ile Met
    355                 360                 365

Thr Gly Arg Ala Asn His Val Trp Asn Thr Thr Gly Ala His Gln Ser
370                 375                 380

Ser Ile Pro Ala Leu Gly Ile Asp Asp Trp Asp Asn Pro Ala Ala Pro
385                 390                 395                 400

Val Xaa Ala Glu Ile Ala Pro Met Pro Ala Gly Leu Glu Thr Trp Val
            405                 410                 415

Ser Leu Tyr Leu Ala Ile Thr Lys Asn Pro Glu Arg Gly Thr Phe Val
        420                 425                 430

Tyr Asp Lys Ala Thr Asp Arg Ala Ala Leu Arg Trp Thr Arg Asp Gln
    435                 440                 445

Asn Thr Pro Ala Val Asn Ala Ala Lys Ser Leu Phe Asp Arg Ile Asn
450                 455                 460

Lys Ala Asn Thr Thr Met Tyr Arg Tyr Asp Leu Phe Gly Pro Gln Leu
465                 470                 475                 480

Lys Asn Phe Ser Asp Asp Phe Cys Tyr His Pro Leu Gly Gly Cys Val
            485                 490                 495

Leu Gly Lys Ala Thr Asp Gly Tyr Gly Arg Val Ala Gly Tyr Arg Asn
        500                 505                 510

Leu Tyr Val Thr Asp Gly Ala Leu Ile Pro Gly Ser Ile Gly Val Asn
    515                 520                 525

Pro Phe Val Thr Ile Thr Ala Leu Ala Glu Arg Asn Ile Glu Arg Ile
530                 535                 540

Ile Ala Glu Asp Val Lys Ala Ala
545                 550

<210> SEQ ID NO 6
<211> LENGTH: 549
<212> TYPE: PRT
<213> ORGANISM: Streptomyces diastaticus
<220> FEATURE:
<221> NAME/KEY: MISC_FEATURE
<222> LOCATION: (162)..(162)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (231)..(231)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (399)..(399)
<223> OTHER INFORMATION: Xaa is Phe, Trp, Ser, Thr, Lys, Ala, Asn, His
      or Asp, provided that when Xaa162 is Met, then Xaa399 is not Phe

<400> SEQUENCE: 6

Met Ile Glu Asn Gln His Leu Ser Arg Arg Arg Leu Leu Gly Leu Ala
1               5                   10                  15

Ala Leu Gly Gly Ala Ala Val Ala Gly Met Thr Thr Ile Ser Val Ala
            20                  25                  30

Pro Arg Ala Ala Ala Ala Gly Gln Gly Ser Pro Arg Ala Gly Asp Gly
```

```
                35                  40                  45
Ala Phe Val Pro Ala Val Val Ile Gly Thr Gly Tyr Gly Ala Val
 50                  55                  60

Ser Ala Leu Arg Leu Gly Glu Ala Gly Ile Pro Thr Leu Met Leu Glu
 65                  70                  75                  80

Met Gly Gln Leu Trp Asn Lys Pro Ala Asp Gly Asn Ile Phe Cys
                 85                  90                  95

Gly Met Leu Lys Pro Asp Arg Arg Ser Ser Trp Phe Lys Ser Arg Thr
                100                 105                 110

Glu Ala Pro Leu Gly Ser Phe Leu Trp Leu Asp Val Ile Asn Arg Asn
            115                 120                 125

Ile Asp Pro Tyr Ala Gly Val Leu Asp Lys Val His Phe Asp Glu Met
            130                 135                 140

Ser Val Tyr Val Gly Arg Gly Val Gly Gly Ser Leu Val Asn Gly
145                 150                 155                 160

Gly Xaa Ala Val Val Pro Lys Arg Ser Tyr Phe Glu Glu Val Leu Pro
                165                 170                 175

Arg Val Asp Ala Ala Gln Met Tyr Asp Arg Tyr Phe Pro Arg Ala Asn
            180                 185                 190

Ser Met Leu Lys Val Asn His Ile Asp Lys Gly Trp Phe Glu Asp Thr
            195                 200                 205

Glu Trp Tyr Lys Tyr Ala Arg Val Ser Arg Glu Gln Ala Gly Lys Ala
210                 215                 220

Gly Leu Ser Thr Thr Phe Xaa Pro Asn Val Tyr Asp Phe Asp His Met
225                 230                 235                 240

Arg Arg Glu Ala Asp Gly Thr Ala Pro Lys Ser Ala Leu Ala Gly Glu
                245                 250                 255

Val Ile Tyr Gly Asn Asn His Gly Lys Gln Ser Leu Asp Lys Thr Tyr
                260                 265                 270

Leu Ala Ala Ala Leu Gly Thr Gly Lys Val Thr Ile Glu Thr Leu His
            275                 280                 285

Gln Val Lys Ala Ile Arg Arg Gln Pro Asp Gly Ser Tyr Val Leu Ser
290                 295                 300

Val Val Gln Ser Asp Ala Asp Gly Lys Thr Ile Ala Gln Lys Glu Ile
305                 310                 315                 320

Gly Cys Arg His Leu Phe Leu Gly Ala Gly Ser Leu Gly Ser Thr Glu
                325                 330                 335

Leu Leu Val Arg Ala Arg Asp Thr Gly Thr Leu Pro Glu Leu Asn Ala
            340                 345                 350

Glu Val Gly Ala Gly Trp Gly Pro Asn Gly Asn Ile Met Thr Gly Arg
            355                 360                 365

Ala Asn His Val Trp Asn Pro Thr Gly Ala His Gln Ser Ser Ile Pro
            370                 375                 380

Ala Leu Gly Ile Asp Asp Trp Asp Asn Pro Ala Ala Pro Val Xaa Ala
385                 390                 395                 400

Glu Ile Ala Pro Met Pro Ala Gly Leu Glu Thr Trp Val Ser Leu Tyr
                405                 410                 415

Leu Ala Ile Thr Lys Asn Pro Glu Arg Gly Thr Phe Val Tyr Asp Lys
            420                 425                 430

Ala Thr Asp Arg Ala Lys Leu Arg Trp Thr Arg Asp Gln Asn Thr Pro
            435                 440                 445

Ala Val Asn Ala Ala Lys Ser Leu Phe Asp Arg Ile Asn Lys Ala Asn
450                 455                 460
```

-continued

```
Thr Thr Met Tyr Arg Tyr Asp Leu Phe Gly Ser Gln Leu Lys Asn Phe
465                 470                 475                 480

Ser Asp Asp Phe Ser Tyr His Pro Leu Gly Gly Cys Val Leu Gly Lys
                485                 490                 495

Ala Thr Asp Leu Tyr Gly Arg Val Ala Gly Tyr Gln Asn Leu Tyr Val
            500                 505                 510

Met Asp Gly Ala Leu Val Pro Gly Ser Ile Gly Val Asn Pro Phe Val
        515                 520                 525

Thr Ile Thr Ala Leu Ala Glu Arg Asn Ile Glu Arg Ile Ala Glu
    530                 535                 540

Asp Val Lys Ala Ala
545
```

<210> SEQ ID NO 7
<211> LENGTH: 552
<212> TYPE: PRT
<213> ORGANISM: Streptomyces griseus
<220> FEATURE:
<221> NAME/KEY: MISC_FEATURE
<222> LOCATION: (165)..(165)
<223> OTHER INFORMATION: Xaa is Met, Phe, Leu, Val, Cys, Ile, Ala, Gln, Tyr, Lys or Ser
<220> FEATURE:
<221> NAME/KEY: MISC_FEATURE
<222> LOCATION: (234)..(234)
<223> OTHER INFORMATION: Xaa is Val, Met, Ile, Ala, Thr, Lys, Cys, Ser, Gly, Glu, Tyr, Pro, Asn, Gln, Trp or His
<220> FEATURE:
<221> NAME/KEY: MISC_FEATURE
<222> LOCATION: (402)..(402)
<223> OTHER INFORMATION: Xaa is Phe, Trp, Ser, Thr, Lys, Ala, Asn, His or Asp, provided that when Xaa165 is Met, then Xaa402 is not Phe

<400> SEQUENCE: 7

```
Met Phe Glu Asn Gln Gln Asn Gln His Leu Ser Arg Arg Arg Leu Leu
1               5                   10                  15

Gly Leu Ala Ala Leu Ser Gly Ala Ala Val Ala Gly Leu Thr Thr Ile
            20                  25                  30

Ser Ala Ala Pro Gln Ala Ala Ala Ala Gly Arg Arg Ala Pro Arg Ala
        35                  40                  45

Gly Asp Gly Ser Phe Val Glu Ala Val Val Ile Gly Thr Gly Tyr Gly
    50                  55                  60

Ala Ala Val Ser Ala Leu Arg Leu Gly Glu Ala Gly Val Pro Thr Leu
65                  70                  75                  80

Met Leu Glu Met Gly Arg Leu Trp Asn Lys Pro Ala Glu Asp Gly Asn
                85                  90                  95

Ile Phe Cys Gly Met Leu Lys Pro Asp Arg Arg Ser Thr Trp Phe Lys
            100                 105                 110

Ser Arg Thr Glu Ala Pro Leu Gly Ser Phe Leu Trp Leu Asp Val Val
        115                 120                 125

Asn Arg Asp Ile Asp Pro Tyr Ala Gly Val Leu Asp Arg Val His Phe
    130                 135                 140

Asp Glu Met Ser Val Tyr Val Gly Arg Gly Val Gly Gly Ser Leu
145                 150                 155                 160

Val Asn Gly Gly Xaa Ala Val Val Pro Lys Arg Ala Tyr Phe Glu Glu
                165                 170                 175

Val Leu Pro Lys Val Asp Ala Ala Glu Met Tyr Asp Arg Tyr Phe Pro
            180                 185                 190

Arg Ala Asn Ser Met Leu Lys Val Asn His Ile Asp Lys Thr Trp Phe
```

195                 200                 205
Glu Asp Thr Glu Trp Tyr Lys Phe Ala Arg Val Ser Arg Glu Gln Ala
210                 215                 220

Ser Lys Ala Gly Leu Gly Thr Thr Phe Xaa Pro Asn Val Tyr Asp Phe
225                 230                 235                 240

Gly His Met Arg Arg Glu Ala Thr Gly Glu Ala Pro Lys Ser Ala Leu
                245                 250                 255

Ala Gly Glu Val Ile Tyr Gly Asn Asn His Gly Lys Gln Ser Leu Asp
            260                 265                 270

Lys Thr Tyr Leu Ala Ala Leu Gly Thr Gly Lys Val Thr Ile Glu
275                 280                 285

Thr Leu His Gln Val Lys Ala Ile Arg Gln Gln Lys Asp Gly Gly Tyr
290                 295                 300

Val Leu Ser Val Asp Gln Thr Asp Ala Asp Gly Lys Thr Val Gly His
305                 310                 315                 320

Lys Glu Ile Gly Cys Arg His Leu Phe Leu Gly Ala Gly Ser Leu Gly
                325                 330                 335

Ser Thr Glu Leu Leu Val Arg Ala Arg Asp Thr Gly Ala Leu Pro Asp
                340                 345                 350

Leu Asn Ala Glu Val Gly Gly Gly Trp Gly Pro Asn Gly Asn Ile Met
            355                 360                 365

Thr Gly Arg Ala Asn His Val Trp Asn Pro Thr Gly Ala His Gln Ser
370                 375                 380

Ser Ile Pro Ala Leu Gly Ile Asp Asp Trp Asn Asn Ala Ala Ala Pro
385                 390                 395                 400

Val Xaa Ala Glu Ile Ala Pro Met Pro Ala Gly Ala Glu Thr Trp Val
                405                 410                 415

Ser Leu Tyr Leu Ala Ile Thr Lys Asn Pro Glu Arg Gly Thr Phe Val
                420                 425                 430

Tyr Asp Lys Ala Thr Asp Arg Val Ala Leu Arg Trp Thr Arg Asp Gln
            435                 440                 445

Asn Thr Pro Ala Val Asn Ala Ala Lys Ser Leu Phe Asp Arg Ile Asn
450                 455                 460

Gln Ala Asn Thr Thr Val Tyr Arg Tyr Asp Leu Phe Gly Lys Gln Val
465                 470                 475                 480

Lys Ala Phe Ser Asp Asp Phe Ser Tyr His Pro Leu Gly Gly Cys Val
                485                 490                 495

Leu Gly Lys Ala Thr Asp Leu Tyr Gly Arg Val Ala Gly His Arg Asn
                500                 505                 510

Leu Tyr Val Met Asp Gly Ser Leu Ile Pro Gly Ser Ile Gly Val Asn
            515                 520                 525

Pro Phe Val Thr Ile Thr Ala Leu Ala Glu Arg Asn Ile Glu Arg Ile
            530                 535                 540

Ile Ala Glu Asp Val Lys Ala Ala
545                 550

<210> SEQ ID NO 8
<211> LENGTH: 547
<212> TYPE: PRT
<213> ORGANISM: Streptomyces sp.
<220> FEATURE:
<221> NAME/KEY: MISC_FEATURE
<222> LOCATION: (160)..(160)
<223> OTHER INFORMATION: Xaa is Met, Phe, Leu, Val, Cys, Ile, Ala, Gln,
      Tyr, Lys or Ser
<220> FEATURE:

<221> NAME/KEY: MISC_FEATURE
<222> LOCATION: (229)..(229)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (397)..(397)
<223> OTHER INFORMATION: Xaa is Phe, Trp, Ser, Thr, Lys, Ala, Asn, His
      or Asp, provided that when Xaa160 is Met, then Xaa397 is not Phe

<400> SEQUENCE: 8

Met Asn Ala His Gln Pro Leu Ser Arg Arg Arg Met Leu Gly Leu Ala
1               5                   10                  15

Ala Leu Gly Ala Ala Ala Leu Thr Gly Gln Thr Thr Ile Thr Ala Ala
            20                  25                  30

Pro Arg Ala Ala Ala Ala Thr Ala Pro Gly Gly Ser Gly Gly Thr Phe
        35                  40                  45

Val Pro Ala Val Val Ile Gly Thr Gly Tyr Gly Ala Ala Val Ser Ala
    50                  55                  60

Leu Arg Leu Gly Glu Ala Gly Val Ser Thr Leu Met Leu Glu Met Gly
65                  70                  75                  80

Gln Leu Trp Asn Gln Pro Gly Pro Asp Gly Asn Val Phe Cys Gly Met
                85                  90                  95

Leu Lys Pro Asp Lys Arg Ser Ser Trp Phe Lys Thr Arg Thr Glu Ala
            100                 105                 110

Pro Leu Gly Ser Phe Leu Trp Leu Asp Leu Ala Asn Arg Asp Ile Asp
        115                 120                 125

Pro Tyr Ala Gly Val Leu Asp Arg Val Asn Phe Asp Gln Met Ser Val
    130                 135                 140

Tyr Val Gly Arg Gly Val Gly Gly Ser Leu Val Asn Gly Gly Xaa
145                 150                 155                 160

Ala Val Thr Pro Arg Arg Ser Tyr Phe Gln Glu Val Leu Pro Gln Val
                165                 170                 175

Asp Ala Asp Glu Met Tyr Gly Thr Tyr Phe Pro Arg Ala Asn Ser Gly
            180                 185                 190

Leu Arg Val Asn Asn Ile Asp Lys Asp Trp Phe Glu Gln Thr Glu Trp
        195                 200                 205

Tyr Thr Phe Ala Arg Val Ala Arg Leu Gln Ala Glu Asn Ala Gly Leu
    210                 215                 220

Lys Thr Thr Phe Xaa Pro Asn Val Tyr Asp Trp Asp Tyr Met Arg Gly
225                 230                 235                 240

Glu Ala Asp Gly Thr Asn Pro Lys Ser Ala Leu Ala Ala Glu Val Ile
                245                 250                 255

Tyr Gly Asn Asn His Gly Lys Val Ser Leu Asp Lys Ser Tyr Leu Ala
            260                 265                 270

Ala Ala Leu Gly Thr Gly Lys Val Thr Val Glu Thr Leu His Gln Val
        275                 280                 285

Lys Thr Ile Arg Gln Gln Asn Asp Gly Thr Tyr Leu Leu Thr Val Glu
    290                 295                 300

Gln Lys Asp Pro Asp Gly Lys Leu Leu Gly Thr Lys Glu Ile Ser Cys
305                 310                 315                 320

Arg His Leu Phe Leu Gly Ala Gly Ser Leu Gly Ser Ile Glu Leu Leu
                325                 330                 335

Leu Arg Ala Arg Glu Thr Gly Thr Leu Pro Gly Leu Ser Ser Glu Ile
            340                 345                 350

Gly Gly Gly Trp Gly Pro Asn Gly Asn Ile Met Thr Ala Arg Ala Asn

```
                    355                 360                 365
His Val Trp Asn Pro Thr Gly Ser Lys Gln Ser Ile Pro Ala Leu
    370                 375                 380

Gly Ile Asp Asp Trp Asp Asn Pro Asp Asn Pro Val Xaa Ala Glu Ile
385                 390                 395                 400

Ala Pro Met Pro Ala Gly Leu Glu Thr Trp Val Ser Leu Tyr Leu Ala
                405                 410                 415

Ile Thr Lys Asn Pro Glu Arg Gly Thr Phe Val Tyr Asp Ala Ala Lys
            420                 425                 430

Asp Arg Ala Asp Leu Arg Trp Thr Arg Asp Gln Asn Ala Pro Ala Val
        435                 440                 445

Ala Ala Ala Lys Ser Leu Phe Asp Arg Val Asn Lys Ala Asn Thr Thr
    450                 455                 460

Ile Tyr Arg Tyr Asp Leu Phe Gly Lys Gln Ile Lys Ala Phe Ala Asp
465                 470                 475                 480

Asp Phe Cys Tyr His Pro Leu Gly Gly Cys Val Leu Gly Lys Ala Thr
                485                 490                 495

Asp Asn Tyr Gly Arg Val Ser Gly Tyr Lys Asn Leu Tyr Val Thr Asp
            500                 505                 510

Gly Ser Leu Ile Pro Gly Ser Ile Gly Val Asn Pro Phe Val Thr Ile
        515                 520                 525

Thr Ala Leu Ala Glu Arg Asn Val Glu Arg Val Ile Lys Glu Asp Ile
    530                 535                 540

Ala Gly Ser
545
```

<210> SEQ ID NO 9
<211> LENGTH: 543
<212> TYPE: PRT
<213> ORGANISM: Streptomyces sp.
<220> FEATURE:
<221> NAME/KEY: MISC_FEATURE
<222> LOCATION: (157)..(157)
<223> OTHER INFORMATION: Xaa is Met, Phe, Leu, Val, Cys, Ile, Ala, Gln, Tyr, Lys or Ser
<220> FEATURE:
<221> NAME/KEY: MISC_FEATURE
<222> LOCATION: (226)..(226)
<223> OTHER INFORMATION: Xaa is Val, Met, Ile, Ala, Thr, Lys, Cys, Ser, Gly, Glu, Tyr, Pro, Asn, Gln, Trp or His
<220> FEATURE:
<221> NAME/KEY: MISC_FEATURE
<222> LOCATION: (394)..(394)
<223> OTHER INFORMATION: Xaa is Phe, Trp, Ser, Thr, Lys, Ala, Asn, His or Asp, provided that when Xaa157 is Met, then Xaa394 is not Phe

<400> SEQUENCE: 9

```
Met Pro Gly Met Ala Ser Leu Asn Arg Arg Phe Leu Gly Leu Ala
1               5                   10                  15

Ala Leu Asn Ser Ala Ala Ala Leu Gly Leu Thr Ser Ile Ser Ala Thr
            20                  25                  30

Thr Ala Arg Ala Ala Thr Val Ala Pro Leu Pro Asp Tyr Ser Pro Ala
        35                  40                  45

Val Val Ile Gly Thr Gly Tyr Gly Ala Ala Val Thr Ala Leu Arg Leu
    50                  55                  60

Gly Glu Ala Gly Val Pro Thr Val Met Leu Glu Met Gly Gln Leu Trp
65                  70                  75                  80

Asn Glu Ala Gly Pro Asp Gly Lys Val Phe Cys Asp Met Leu Lys Pro
                85                  90                  95
```

-continued

```
Asp Arg Arg Ser Met Trp Phe Lys Lys Arg Thr Glu Ala Pro Leu Ala
            100                 105                 110

Ser Phe Leu Trp Leu Asp Val Ala Asn His Asp Ile Asp Pro Tyr Ala
        115                 120                 125

Gly Val Leu Asp Arg Val Asn Tyr Gly Gly Met Ser Val Tyr Val Gly
    130                 135                 140

Arg Gly Val Gly Gly Ser Leu Val Asn Gly Ala Xaa Ala Val Gln
145                 150                 155                 160

Pro Lys Arg Ser Tyr Phe Glu Glu Ile Leu Pro Arg Val Asp Ala Asp
                165                 170                 175

Glu Met Tyr Gly Lys Tyr Tyr Pro Arg Ala Asn Ala Gly Leu Gly Val
            180                 185                 190

Asn His Ile Asp Pro Asp Trp Phe Glu Thr Cys Lys Ser Tyr Gln Phe
        195                 200                 205

Ala Arg Val Ser Arg Lys Ala Ala Gln Lys Thr Gly Leu Lys Thr Thr
    210                 215                 220

Phe Xaa Pro Ser Val Tyr Asp Phe Glu Tyr Met Lys Lys Glu Glu Ala
225                 230                 235                 240

Gly Thr Val Glu Arg Ser Ala Leu Ala Ser Glu Val Ile Tyr Gly Asn
                245                 250                 255

Asn His Gly Lys Arg Ser Leu Asp Lys Thr Tyr Leu Ala Ala Ala Leu
            260                 265                 270

Gly Thr Gly His Val Thr Ile Gln Thr Leu His Glu Val Arg Glu Ile
        275                 280                 285

Ile Gln Gln Gln Asp Gly Thr Tyr Thr Leu Val Val Arg Glu Ser Asp
    290                 295                 300

Ala Leu Gly Asn Val Leu Ala Thr Lys His Leu Ser Thr Lys Tyr Leu
305                 310                 315                 320

Phe Leu Gly Ala Gly Ser Leu Gly Ser Thr Glu Leu Val Arg Ala
                325                 330                 335

Arg Asp Thr Gly Arg Leu Pro Arg Leu Ser Glu Ala Val Gly Gln Gly
            340                 345                 350

Trp Gly Thr Asn Gly Asn Val Met Leu Gly Arg Ala Asn His Val Trp
        355                 360                 365

Asp Thr Thr Gly Ser Leu Glu Ser Gly Met Pro Ala Leu Gly Ile Asp
    370                 375                 380

Asp Trp Asp Asn Pro Ala His Pro Val Xaa Ala Glu Ile Ala Pro Val
385                 390                 395                 400

Pro Ala Gly Leu Glu Thr Trp Ala Ser Leu Tyr Leu Ala Ile Thr Lys
                405                 410                 415

Asn Pro Glu Arg Gly His Phe Thr Tyr Asp Ala Ala Ser Asp Ser Ala
            420                 425                 430

Lys Leu Gln Trp Ser Pro Asp Gln Gly Gln Pro Ser Ile Asp Ala Ala
        435                 440                 445

Lys Ser Leu Phe Asp Arg Ile Asn Lys Ala Asn Ser Thr Ile Tyr Arg
    450                 455                 460

Tyr Asp Leu Phe Gly Asp Thr Arg Ala Phe Glu Asn Arg Phe Thr Tyr
465                 470                 475                 480

His Pro Leu Gly Gly Leu Val Leu Gly Glu Ala Thr Asp Asp Tyr Gly
                485                 490                 495

Arg Val Lys Gly Tyr Arg Asn Leu Tyr Val Thr Asp Gly Ser Leu Ile
            500                 505                 510

Pro Gly Ser Thr Gly Val Asn Pro Phe Val Thr Ile Thr Ala Leu Ala
```

```
                515                 520                 525
Glu Arg Asn Ile Glu Arg Val Leu Ala Glu Asp Gly Val Arg Ala
    530                 535                 540
```

<210> SEQ ID NO 10
<211> LENGTH: 547
<212> TYPE: PRT
<213> ORGANISM: Streptomyces sp.
<220> FEATURE:
<221> NAME/KEY: MISC_FEATURE
<222> LOCATION: (165)..(165)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (234)..(234)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (402)..(402)
<223> OTHER INFORMATION: Xaa is Phe, Trp, Ser, Thr, Lys, Ala, Asn, His
      or Asp, provided that when Xaa165 is Met, then Xaa402 is not Phe

<400> SEQUENCE: 10

```
Met Ala Gly Trp Ala Glu Ser Ala His Asp Ala Met Thr His Asn
1               5                   10                  15

Leu Thr Arg Arg Gln Leu Gly Leu Asn Ala Leu Arg Ala Ala Ala
            20                  25                  30

Leu Gly Ile Thr Arg Ile Gly Leu Gly Ala Ala Ala Ala Glu Pro
        35                  40                  45

Pro Ala Ala Pro Tyr Ala Pro Ala Val Val Val Gly Ser Gly Tyr Gly
    50                  55                  60

Ser Ala Val Ala Ala Leu Arg Leu Gly Gln Ala Gly Val Arg Thr Val
65                  70                  75                  80

Val Leu Glu Met Gly Arg Leu Trp Asp Thr Pro Gly Pro Asp Gly Lys
                85                  90                  95

Val Phe Pro Ser Thr Ser Ala Pro Asp Gln Arg Ser Met Trp Phe Arg
            100                 105                 110

Thr Arg Thr Glu Ala Pro Leu Ala Gln Phe Leu Trp Leu Asp Val Val
        115                 120                 125

Asn Arg Asp Ile Ser Pro Tyr Pro Gly Val Leu Asp Arg Val Asn His
    130                 135                 140

Gly Gly Met Ser Val Tyr Val Gly Arg Gly Val Gly Gly Gly Ser Leu
145                 150                 155                 160

Val Asn Gly Gly Xaa Ala Pro Thr Pro Arg Arg Ser Tyr Phe Ala Glu
                165                 170                 175

Val Phe Pro Arg Val Asp Ala Glu Met Tyr Gly Tyr Tyr Phe Pro
            180                 185                 190

Arg Ala Arg Ala Met Leu Gly Val Asn Gly Ile Asp Pro Ala Trp Phe
        195                 200                 205

Glu Ser Thr Glu Trp Tyr Arg Phe Ala Arg Ile Ser Arg Lys His Ala
    210                 215                 220

Gln Asn Thr Gly Leu Lys Thr Thr Phe Xaa Pro Asn Val Tyr Asp Phe
225                 230                 235                 240

Gly Tyr Met Lys Arg Glu Ala Ala Gly Thr Ala Thr Arg Ser Ala Leu
                245                 250                 255

Ala Gly Glu Val Ile Tyr Gly Asn Asn His Gly Lys Lys Ser Val Asp
            260                 265                 270
```

```
Lys Thr Tyr Leu Ala Ala Ala Leu Gly Thr Gly Asn Val Thr Ile Glu
            275                 280                 285

Thr Met Gln Arg Val Val Ala Val Arg Gln Asp Leu Ala Gly Gly Tyr
        290                 295                 300

Val Leu Thr Val His Thr Ser Asp Val Thr Gly Arg Val Thr Gln Val
305                 310                 315                 320

Arg Glu Leu Gly Cys Arg Gln Leu Phe Leu Gly Ala Gly Ser Leu Gly
                325                 330                 335

Thr Thr Glu Ile Leu Leu Arg Ala Arg Glu Thr Gly Ala Leu Pro Ala
            340                 345                 350

Leu Ser Glu Lys Val Gly Leu Gly Trp Gly Pro Asn Gly Asn Val Met
        355                 360                 365

Thr Ala Arg Ala Asn His Leu Trp Asp Thr Val Gly Cys Asn Gln Ala
370                 375                 380

Thr Met Pro Ala Leu Gly Ile Asp Asp Trp Asp Asn Ala Ala Asn Pro
385                 390                 395                 400

Val Xaa Ala Glu Ile Ala Pro Leu Pro Met Gly Ile Glu His Trp Ile
                405                 410                 415

Ser Met Tyr Leu Ala Ile Thr Lys Asn Pro Glu Arg Gly Arg Phe Val
            420                 425                 430

Tyr Asp Ala Ala Thr Asp Ser Ala Arg Leu Asn Trp Thr Arg Asp Gln
        435                 440                 445

Asn Ala Pro Ala Val Ala Ala Lys Asn Leu Phe Asp Arg Ile Asn
450                 455                 460

Arg Arg Asn Val Thr Ile Tyr Arg Tyr Asp Leu Phe Gly Asp Asn Lys
465                 470                 475                 480

Ala Phe Ala Asp Asp Phe Thr Tyr His Pro Leu Gly Gly Cys Val Leu
                485                 490                 495

Gly Glu Ala Thr Asp Ala Tyr Gly Arg Val Lys Gly Tyr Gln Gly Leu
            500                 505                 510

Tyr Val Leu Asp Gly Ser Leu Val Pro Gly Ser Leu Gly Val Asn Pro
        515                 520                 525

Phe Val Thr Ile Thr Ala Leu Ala Glu Arg Asn Met Glu Arg Ile Leu
530                 535                 540

Ala Gln Pro
545

<210> SEQ ID NO 11
<211> LENGTH: 550
<212> TYPE: PRT
<213> ORGANISM: Streptomyces sp.
<220> FEATURE:
<221> NAME/KEY: MISC_FEATURE
<222> LOCATION: (166)..(166)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (235)..(235)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (403)..(403)
<223> OTHER INFORMATION: Xaa is Phe, Trp, Ser, Thr, Lys, Ala, Asn, His
      or Asp, provided that when Xaa166 is Met, then Xaa403 is not Phe

<400> SEQUENCE: 11

Met Gly Gly Arg Arg Glu Ser Ala His Asp Ala Ala Met Thr Ser Asn
1               5                   10                  15
```

```
Leu Thr Arg Arg Gln Met Leu Gly Leu Gly Ala Leu Ser Thr Ala Ala
             20                  25                  30

Ala Leu Gly Phe Thr Arg Ile Gly Ala Ala Ser Ala Ala Ala Leu Glu
         35                  40                  45

Pro Pro Ala Ala Ser Tyr Ala Pro Ala Ile Val Val Gly Ser Gly Tyr
 50                      55                  60

Gly Ser Ala Val Ala Ala Leu Arg Leu Gly Gln Ala Gly Val Arg Thr
 65                  70                  75                  80

Val Val Leu Glu Met Gly Arg Leu Trp Asp Thr Pro Gly Ala Asp Gly
                 85                  90                  95

Lys Val Phe Pro Ser Thr Ser Ala Pro Asp Gln Arg Ser Met Trp Phe
            100                 105                 110

Arg Asn Arg Thr Glu Ala Pro Leu Ala Gln Phe Leu Trp Leu Asp Val
            115                 120                 125

Val Asn Arg Asp Ile Ser Pro Tyr Pro Gly Val Leu Asp Arg Val Asn
130                 135                 140

Tyr Gly Asp Met Ser Val Tyr Val Gly Arg Gly Val Gly Gly Gly Ser
145                 150                 155                 160

Leu Val Asn Gly Gly Xaa Ser Pro Thr Pro Arg Arg Ser Tyr Phe Ser
                165                 170                 175

Glu Val Leu Pro Arg Val Asp Ala Asp Glu Met Tyr Gly Thr Tyr Tyr
            180                 185                 190

Pro Arg Ala Arg Ala Met Leu Gly Val Gly Asp Ile Asp Pro Ala Trp
            195                 200                 205

Phe Glu Ser Thr Glu Trp Tyr Arg Phe Ala Arg Ile Ser Arg Lys His
    210                 215                 220

Ala Gln Asn Thr Gly Leu Lys Thr Val Phe Xaa Pro Asn Val Tyr Asp
225                 230                 235                 240

Phe Glu Tyr Met Lys Arg Glu Ala Ala Gly Thr Ala Thr Arg Ser Ala
                245                 250                 255

Leu Ala Gly Glu Val Ile Tyr Gly Asn Asn His Gly Lys Lys Ser Val
            260                 265                 270

Asp Lys Thr Tyr Leu Ala Ala Ile Gly Thr Gly Asn Val Thr Ile
            275                 280                 285

Glu Thr Met Gln Arg Val Val Ala Val Arg Gln Asp Pro Ala Gly Gly
            290                 295                 300

Tyr Val Leu Thr Val Arg Thr Ser Asp Val Thr Gly Arg Val Thr Gln
305                 310                 315                 320

Val Arg Glu Leu Gly Cys Arg Arg Leu Phe Leu Gly Ala Gly Ser Leu
                325                 330                 335

Gly Thr Thr Glu Ile Leu Leu Arg Ala Arg Glu Thr Gly Thr Leu Pro
            340                 345                 350

Ala Leu Ser Glu Lys Val Gly Leu Gly Trp Gly Pro Asn Gly Asn Val
            355                 360                 365

Met Thr Ala Arg Ala Asn His Leu Trp Asp Thr Val Gly Ser Asn Gln
            370                 375                 380

Ala Thr Met Pro Ala Leu Gly Ile Asp Asp Trp Asp Asn Ala Ala Asn
385                 390                 395                 400

Pro Val Xaa Ala Glu Ile Ala Pro Leu Pro Met Gly Phe Glu His Trp
                405                 410                 415

Ile Ser Met Tyr Leu Ala Ile Thr Lys Asn Pro Glu Arg Gly His Phe
            420                 425                 430
```

-continued

```
Thr Tyr Asp Ala Ala Ser Asp Ser Ala Arg Leu Gln Trp Arg Arg Asp
            435                 440                 445

Gln Asn Thr Pro Ala Val Arg Ala Ala Lys Asn Leu Phe Asp Arg Ile
    450                 455                 460

Asn Arg Ala Asn Phe Thr Ile Tyr Arg Tyr Asp Leu Phe Gly Gly Asn
465                 470                 475                 480

Lys Asn Phe Ala Asp Asp Phe Thr Tyr His Pro Leu Gly Gly Cys Val
                485                 490                 495

Leu Gly Glu Ala Thr Asp Asp Phe Gly Arg Ala Lys Gly Tyr Gln Gly
            500                 505                 510

Leu Tyr Val Val Asp Gly Ser Leu Val Pro Gly Ser Leu Gly Val Asn
        515                 520                 525

Pro Phe Val Thr Ile Thr Ala Leu Ala Glu Arg Asn Met Ala Arg Ile
    530                 535                 540

Leu Ala Gln Asp Pro His
545                 550

<210> SEQ ID NO 12
<211> LENGTH: 540
<212> TYPE: PRT
<213> ORGANISM: Streptomyces scabiei
<220> FEATURE:
<221> NAME/KEY: MISC_FEATURE
<222> LOCATION: (154)..(154)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (223)..(223)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (391)..(391)
<223> OTHER INFORMATION: Xaa is Phe, Trp, Ser, Thr, Lys, Ala, Asn, His
      or Asp, provided that when Xaa154 is Met, then Xaa391 is not Phe

<400> SEQUENCE: 12

Met Gln Arg Gln Leu Thr Arg Arg His Ile Leu Gly Met Ala Ala Leu
1               5                   10                  15

Gln Thr Ala Ala Gly Leu Gly Leu Thr Arg Ile Gly Leu Gln Ser Ala
            20                  25                  30

Arg Ala Ala Glu Pro Asp Ala Val Asp Asn Ala Pro Ala Leu Val Ile
        35                  40                  45

Gly Ser Gly Tyr Gly Ala Ala Val Ala Ala Leu Arg Leu Gly Gln Ala
    50                  55                  60

Gly Ile Arg Thr Leu Val Leu Glu Met Gly Arg Ala Trp Thr Thr Pro
65                  70                  75                  80

Gly Ala Asp Gly Lys Ile Phe Cys Ser Thr Lys Glu Pro Asp Glu Arg
                85                  90                  95

Ser Met Trp Phe Lys Thr Arg Thr Glu Ala Pro Leu Ala Thr Phe Leu
            100                 105                 110

Trp Leu Asp Val Val Asn Gln Asp Ile Ser Arg Tyr Pro Gly Val Leu
        115                 120                 125

Asp Arg Val Arg His Ala Asn Met Ser Val Phe Leu Gly Arg Gly Val
    130                 135                 140

Gly Gly Gly Ser Leu Val Asn Gly Ser Xaa Ala Val Thr Pro Leu Arg
145                 150                 155                 160

Ser Tyr Phe Ala Glu Gln Phe Pro Thr Val Asp Thr Ala Glu Met Tyr
                165                 170                 175
```

```
Ser Thr Tyr Phe Pro Arg Ala Arg Ser Met Leu Gly Val Asn Thr Val
            180                 185                 190

Asp Pro Ala Trp Phe Glu Ser Thr Glu Trp Tyr Arg Phe Ser Arg Val
        195                 200                 205

Ser Arg Ala His Ala Ala Lys Ala Gly Leu Arg Thr Thr Phe Xaa Pro
    210                 215                 220

Ser Val Tyr Asp Phe Asp His Met Gln Arg Glu Ala Ala Gly Thr Ala
225                 230                 235                 240

Thr Lys Ser Ala Leu Ala Gly Glu Val Ile Tyr Gly Asn Asn His Gly
                245                 250                 255

Lys Lys Ser Leu Asp Lys Thr Tyr Leu Ala Ala Ala Leu Gly Thr Gly
            260                 265                 270

Asn Val Thr Ile His Thr Met Glu Arg Ala Arg Gly Ile Arg Arg Leu
        275                 280                 285

Gly Asp Gly Thr Tyr Val Val Thr Ala Asp Arg Ile Asp Gly Thr Gly
    290                 295                 300

Ala Val Val Glu Thr Lys Glu Tyr Gly Cys Thr Tyr Leu Phe Leu Gly
305                 310                 315                 320

Ala Gly Ser Val Gly Thr Thr Glu Leu Leu Val Arg Ala Arg Ala Lys
                325                 330                 335

Gly Thr Leu Pro Ala Leu Asn Ala Ser Val Gly Ala Gly Trp Gly Pro
            340                 345                 350

Asn Gly Asn Val Met Leu Gly Arg Ala Asn His Leu Trp Asp Thr Val
        355                 360                 365

Gly Ala Asn Gln Ser Thr Met Pro Val Met Gly Ile Asp Asp Trp Ala
    370                 375                 380

Asn Thr Ala Asn Pro Val Xaa Ala Glu Ile Ala Pro Leu Pro Thr Gly
385                 390                 395                 400

Leu Glu His Trp Val Ser Leu Tyr Leu Ala Ile Thr Lys Asn Thr Glu
                405                 410                 415

Arg Ala Ser Phe Thr Tyr Asp Ala Ala Thr Asp Ser Ala Lys Leu Gly
            420                 425                 430

Trp Ser Ala Ala Gln Ser Ala Val Ser Ser Met Ala Lys Lys Leu
        435                 440                 445

Phe Asp Arg Ile Asn Ser Ala Asn Ser Thr Met Tyr Arg Tyr Asp Leu
    450                 455                 460

Phe Gly Ser Ser Asn Lys Val Phe Ala Asp Asp Phe Thr Tyr His Pro
465                 470                 475                 480

Leu Gly Gly Cys Val Leu Gly Arg Ala Thr Asp Tyr Gly Arg Val
                485                 490                 495

Lys Gly Tyr Glu Asn Leu Tyr Val Thr Asp Gly Ser Leu Val Pro Gly
            500                 505                 510

Ser Ile Gly Val Asn Pro Phe Val Thr Ile Thr Ala Leu Ala Glu Arg
        515                 520                 525

Asn Val Ala Arg Val Leu Val Glu Asp Thr Ala Pro
    530                 535                 540

<210> SEQ ID NO 13
<211> LENGTH: 543
<212> TYPE: PRT
<213> ORGANISM: Streptomyces bingchenggensis
<220> FEATURE:
<221> NAME/KEY: MISC_FEATURE
<222> LOCATION: (158)..(158)
<223> OTHER INFORMATION: Xaa is Met, Phe, Leu, Val, Cys, Ile, Ala, Gln,
```

```
        Tyr, Lys or Ser
<220> FEATURE:
<221> NAME/KEY: MISC_FEATURE
<222> LOCATION: (227)..(227)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (395)..(395)
<223> OTHER INFORMATION: Xaa is Phe, Trp, Ser, Thr, Lys, Ala, Asn, His
      or Asp, provided that when Xaa158 is Met, then Xaa395 is not Phe

<400> SEQUENCE: 13

Met Thr Ala Asn Leu Thr Arg Arg His Ile Leu Gly Leu Ala Ala Leu
 1               5                  10                  15

Arg Gly Ala Ala Ala Leu Gly Leu Thr Arg Ile Ala Leu Ser Pro Ala
            20                  25                  30

Ala Ala Ala Asp Arg Pro Ala Pro Ala Ala Ser Ala Glu Tyr Ala Pro
        35                  40                  45

Ala Val Val Val Gly Ser Gly Tyr Gly Ala Ala Val Ala Ala Leu Arg
    50                  55                  60

Leu Gly Glu Ala Gly Val Lys Thr Leu Val Leu Glu Met Gly Arg Leu
65                  70                  75                  80

Trp Asn Ala Pro Ala Ser Asp Gly Lys Val Tyr Cys Ser Met Thr Ala
                85                  90                  95

Pro Asp Arg Arg Ser Met Trp Phe Lys Thr Arg Thr Glu Ala Pro Leu
            100                 105                 110

Ala Thr Phe Leu Trp Leu Asp Val Ile Asn Lys Asp Ile Thr Pro Tyr
        115                 120                 125

Pro Gly Val Leu Asp Arg Val Arg Phe Pro Asn Met Ser Val Tyr Val
    130                 135                 140

Gly Arg Gly Val Gly Gly Gly Ser Leu Val Asn Gly Gly Xaa Ala Val
145                 150                 155                 160

Thr Pro Ser Arg Ala Tyr Phe Gln Glu Val Leu Pro Gln Val Asp Ala
                165                 170                 175

Asp Ala Met Tyr Ala Thr Tyr Phe Pro Leu Ala Asn Arg Met Leu Gly
            180                 185                 190

Ala Ala Thr Val Pro Ser Ala Trp Phe Glu Ser Thr Glu Trp Tyr Lys
        195                 200                 205

Tyr Ala Arg Val Ser Arg Asp Gln Ala Lys Thr Ala Gly Leu Lys Thr
    210                 215                 220

Val Phe Xaa Pro Asn Val Tyr Asp Phe Asp Tyr Met Gln Arg Glu Ala
225                 230                 235                 240

Ala Gly Thr Ala Thr Lys Ser Ala Leu Ala Gln Glu Val Ile Tyr Gly
                245                 250                 255

Asn Asn Phe Gly Lys Arg Ser Leu Asp Lys Thr Tyr Leu Ala Ala Ala
            260                 265                 270

Leu Gly Thr Gly Asn Val Thr Ile Arg Thr Leu Ser Arg Ala Arg Ala
        275                 280                 285

Ile Arg Arg Ala Ala Asp Gly Thr Tyr Val Leu Thr Val Asp Arg Leu
    290                 295                 300

Asp Asp Thr Gly Ala Val Val Gly Thr Asp Glu Ile Ser Cys Arg Ser
305                 310                 315                 320

Leu Phe Leu Gly Ala Gly Ser Leu Gly Thr Thr Glu Leu Leu Leu Arg
                325                 330                 335

Ala Arg Glu Thr Gly Thr Leu Pro Ala Leu Ser Pro Gln Ile Gly Arg
            340                 345                 350
```

```
Gly Trp Gly Gly Asn Gly Asn Val Met Leu Gly Arg Ala Asn His Ile
            355                 360                 365

Trp Asn Thr Thr Gly Ala Asn Gln Ser Thr Ile Pro Val Met Gly Ile
    370                 375                 380

Asp Asp Trp Ser Asn Ala Thr Asn Pro Val Xaa Ala Glu Ile Ala Pro
385                 390                 395                 400

Leu Pro Ala Gly Thr Glu Thr Trp Ala Ser Leu Tyr Leu Ala Ile Thr
                405                 410                 415

Lys Asn Pro Glu Arg Gly Thr Phe Thr Tyr Asp Ala Ala Lys Asp Ala
                420                 425                 430

Ala Val Leu Asn Trp Thr Gly Thr Gln Ser Ala Pro Ser Val Thr Ala
            435                 440                 445

Ala Lys Ser Leu Phe Asp Arg Leu Asn Ser Ala Asn Gly Thr Ile Tyr
        450                 455                 460

Arg Tyr Asp Leu Phe Gly Asp Thr Arg Ala Phe Ala Ala Asp Phe Cys
465                 470                 475                 480

Tyr His Pro Leu Gly Gly Cys Val Leu Gly Arg Ala Thr Asp Ala Tyr
                485                 490                 495

Gly Arg Ala Val Gly Tyr Asp Arg Leu Tyr Val Thr Asp Gly Ser Leu
            500                 505                 510

Ile Pro Gly Ser Ile Gly Val Asn Pro Phe Val Thr Ile Thr Ala Leu
        515                 520                 525

Ala Glu Arg Thr Met Ala Arg Val Leu Ala Glu Asp Gly Val Gly
            530                 535                 540

<210> SEQ ID NO 14
<211> LENGTH: 551
<212> TYPE: PRT
<213> ORGANISM: Streptomyces violaceusniger
<220> FEATURE:
<221> NAME/KEY: MISC_FEATURE
<222> LOCATION: (164)..(164)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (233)..(233)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (401)..(401)
<223> OTHER INFORMATION: Xaa is Phe, Trp, Ser, Thr, Lys, Ala, Asn, His
      or Asp, provided that when Xaa164 is Ile, then Xaa401 is not Phe

<400> SEQUENCE: 14

Met Ala Arg Ser Gly Asp Ser Ala His His Ala Ala Met Thr Ala Asp
1               5                   10                  15

Leu Thr Arg Arg His Ile Leu Gly Leu Ala Ala Leu Gln Ser Ala Ala
            20                  25                  30

Ala Leu Gly Leu Thr Arg Ile Gly Leu Thr Pro Ala Ala Ala Ala Gln
        35                  40                  45

Arg Ala Asp His Phe Pro Ala Val Val Gly Ser Gly Tyr Gly Ala
    50                  55                  60

Ala Val Ala Ala Leu Arg Leu Gly Glu Ala Gly Ile Arg Thr Leu Val
65                  70                  75                  80

Val Glu Met Gly Arg Leu Trp Asp Thr Pro Gly Pro Asp Gly Arg Val
                85                  90                  95

His Cys Ser Met Thr Ala Pro Asp Gln Arg Ser Met Trp Phe Lys Thr
```

```
                100             105                 110
Arg Thr Glu Ala Pro Leu Ser Thr Phe Leu Trp Leu Asp Val Ile Asn
            115                 120                 125

Lys Asp Ile Thr Pro Tyr Pro Gly Val Leu Asp Arg Val Arg Phe Pro
        130                 135                 140

Gly Met Ser Val Tyr Val Gly Arg Gly Val Gly Gly Ser Leu Val
145                 150                 155                 160

Asn Gly Gly Xaa Ala Val Thr Pro Ser Arg Ser Tyr Phe Gln Gln Met
                165                 170                 175

Leu Pro Gln Val Ala Ala Asp Pro Met Tyr Asp Thr Tyr Phe Pro Leu
            180                 185                 190

Ala Asn Arg Met Leu Gly Ala Asn Thr Val Pro Ser Ala Trp Phe Glu
        195                 200                 205

Ala Thr Glu Trp Tyr Thr Tyr Ala Arg Val Ala Arg Asp Gln Ala Ala
    210                 215                 220

Arg Ala Gly Leu Lys Thr Val Phe Xaa Pro Asn Val Tyr Asp Phe Asp
225                 230                 235                 240

Tyr Met Arg Arg Glu Ala Asp Gly Thr Ala Thr Lys Ser Ala Leu Ala
                245                 250                 255

Gln Glu Val Ile Tyr Gly Asn Asn Phe Gly Lys Arg Ser Leu Asp Lys
            260                 265                 270

Thr Tyr Leu Ala Ala Ala Leu Gly Thr Gly Gln Val Thr Leu His Thr
        275                 280                 285

Leu Ser Arg Ala Arg Ala Leu Arg Arg Ala Pro Asp Gly Ser Tyr Val
    290                 295                 300

Leu Thr Val Glu Arg Val Asp Thr Thr Gly Thr Val Val Ser Thr Asp
305                 310                 315                 320

Glu Ile Thr Cys Gly Ser Leu Phe Leu Gly Ala Gly Ser Leu Gly Thr
                325                 330                 335

Thr Glu Leu Leu Leu Arg Ala Arg Glu Thr Gly Ala Leu Pro Glu Leu
            340                 345                 350

Ser Glu Glu Val Gly Arg Gly Trp Gly Gly Asn Gly Asn Val Met Leu
        355                 360                 365

Gly Arg Ala Asn His Val Trp His Pro Thr Gly Ala Arg Gln Ser Thr
    370                 375                 380

Ile Pro Val Met Ala Ile Asp Asp Trp Ser Asn Thr Ala Asn Pro Val
385                 390                 395                 400

Xaa Ala Glu Ile Ala Pro Leu Pro Ala Gly Leu Glu Thr Trp Val Ser
                405                 410                 415

Leu Tyr Leu Ala Ile Thr Arg Asn Pro Glu Arg Ala Thr Phe Thr Tyr
            420                 425                 430

Asp Ala Ala Lys Asp Ala Ala Val Leu Asp Trp Thr Arg Ala Gln Ser
        435                 440                 445

Ala Pro Ser Val Ala Ala Lys Ala Leu Phe Asp Arg Val Asn Tyr
    450                 455                 460

Ala Asn Ala Thr Ile Tyr Arg Tyr Asp Leu Phe Gly Asp Thr Arg Ala
465                 470                 475                 480

Ile Ala Asp Asp Phe Cys Tyr His Pro Leu Gly Gly Cys Val Leu Gly
                485                 490                 495

Arg Ala Thr Asp Pro Tyr Gly Arg Val Thr Gly Tyr Asp Gly Leu Tyr
            500                 505                 510

Val Thr Asp Gly Ser Leu Ile Pro Gly Ser Ile Gly Val Asn Pro Phe
        515                 520                 525
```

```
Val Thr Ile Thr Ala Leu Ala Glu Arg Thr Met Ala Arg Val Leu Ala
    530                 535                 540

Glu Asp Arg Val Gly Ala Arg
545                 550

<210> SEQ ID NO 15
<211> LENGTH: 533
<212> TYPE: PRT
<213> ORGANISM: Stackebrandtia nassauensis
<220> FEATURE:
<221> NAME/KEY: MISC_FEATURE
<222> LOCATION: (148)..(148)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (217)..(217)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (385)..(385)
<223> OTHER INFORMATION: Xaa is Phe, Trp, Ser, Thr, Lys, Ala, Asn, His
      or Asp, provided that when Xaa148 is Met, then Xaa385 is not Phe

<400> SEQUENCE: 15

Met Gly Ile Ser Arg Arg Lys Leu Leu Gly Leu Gly Ala Leu Ala Ala
1               5                   10                  15

Gly Ala Ser Ala Gly Val Thr Thr Ile Gly Pro Ala Ala Ala Ala Thr
                20                  25                  30

Ser Gly Asp Phe Val Pro Ala Leu Val Ile Gly Ser Gly Tyr Gly Ala
            35                  40                  45

Ala Val Ala Ala Leu Arg Leu Gly Glu Ala Gly Val Arg Thr Thr Ile
        50                  55                  60

Leu Glu Met Gly Arg Leu Trp His Asp Pro Gly His Asp Gly Lys Ile
65                  70                  75                  80

Phe Cys Ala Thr Thr Asn Pro Asp His Arg Ser Met Trp Phe Arg His
                85                  90                  95

Arg Thr Glu Ala Pro Leu Asp Thr Phe Leu Trp Leu Asp Val Val Asn
            100                 105                 110

Arg Pro Ile Lys Pro Tyr Pro Gly Val Leu Asp Arg Val His Phe Asp
        115                 120                 125

Glu Met Ser Val Tyr Val Gly Arg Gly Val Gly Gly Ser Leu Val
    130                 135                 140

Asn Gly Gly Xaa Ala Val Val Pro Arg Arg Lys Tyr Phe Gln Gln Val
145                 150                 155                 160

Leu Pro Glu Val Asp Ala Asp Asp Met Tyr Arg Lys Phe Phe Pro Leu
                165                 170                 175

Ala Thr Glu Cys Leu Gly Val Asn Asp Ile Asp Thr Asp Tyr Phe Thr
            180                 185                 190

Asp Ser Asp Tyr Tyr Glu Phe Ala Arg Val Ala Gly Arg Gln Ala Glu
        195                 200                 205

Glu Thr Gly Leu Ala Thr Thr Phe Xaa Pro Asn Val Tyr Asp Phe Asp
    210                 215                 220

His Met Ala Arg Glu Glu Ala Gly Thr Ala Thr Lys Ser Ala Leu Ala
225                 230                 235                 240

Ala Glu Val Ile Tyr Gly Asn Asn His Gly Lys Arg Ser Leu Asp His
                245                 250                 255

Ser Tyr Leu Ala Ser Ala Leu Gly Thr Gly Asn Val Thr Ile Glu Thr
```

-continued

```
                    260                 265                 270
Leu His Gln Val Arg Asp Ile Arg Gln Asn Arg Asp Gly Ser Tyr Val
                275                 280                 285

Val Thr Val Asp His Ile Asp Glu Thr Gly Glu Val Glu Ser Lys
            290                 295                 300

Gln Ile Gly Cys Arg His Leu Phe Leu Gly Ala Gly Ser Leu Gly Thr
305                 310                 315                 320

Thr Glu Leu Leu Leu Arg Ala Arg Asp Thr Gly Ala Leu Pro Asp Leu
                325                 330                 335

Asp Ala Asp Val Gly Gln Gly Trp Gly Pro Asn Gly Asn Ile Met Ala
                340                 345                 350

Gly Arg Ala Asn Asn Ala Ser Gln Pro Thr Gly Ala Arg Gln Ser Ala
                355                 360                 365

Ile Pro Val Leu Ala Ile Asp Asp Trp Asp Asn Glu Ala Ala Arg Val
                370                 375                 380

Xaa Ala Glu Ile Ala Pro Val Pro Ala Gly Phe Glu Thr Trp Ile Ser
385                 390                 395                 400

Met Tyr Leu Ala Ile Thr Glu Asn Pro Glu Arg Ala Ser Phe Arg Tyr
                405                 410                 415

Asp Pro Ala Thr Asp Arg Ala Val Leu Asp Trp Arg Arg Asp Gln Asn
                420                 425                 430

Thr Pro Ser Val Ala Ser Ala Lys Ser Leu Leu Asp Arg Ile Asn Glu
                435                 440                 445

Thr Gln Lys Thr Thr Tyr Arg His Asp Leu Phe Gly Asp Asp Arg Ala
                450                 455                 460

Phe Ala Asp Asp Phe Cys Tyr His Pro Leu Gly Gly Cys Val Leu Gly
465                 470                 475                 480

Asn Ala Thr Asp Asn Tyr Gly Arg Leu Lys Gly Tyr Arg Asn Leu Tyr
                485                 490                 495

Ala Thr Asp Gly Ala Leu Ile Pro Gly Ser Leu Gly Val Asn Pro Phe
                500                 505                 510

Val Thr Ile Thr Ala Leu Ala Glu Arg Asn Met Ala Lys Ile Ile Ala
                515                 520                 525

Thr Asp Ile Thr Thr
                530

<210> SEQ ID NO 16
<211> LENGTH: 545
<212> TYPE: PRT
<213> ORGANISM: Streptomyces clavuligerus
<220> FEATURE:
<221> NAME/KEY: MISC_FEATURE
<222> LOCATION: (154)..(154)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (223)..(223)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (397)..(397)
<223> OTHER INFORMATION: Xaa is Phe, Trp, Ser, Thr, Lys, Ala, Asn, His
      or Asp, provided that when Xaa154 is Met, then Xaa397 is not Phe

<400> SEQUENCE: 16

Met Thr Pro His Leu Thr Arg Arg Gln Leu Met Gly Ala Ala Ala Leu
1               5                   10                  15
```

```
Gln Thr Ala Ala Val Leu Gly Phe Thr Arg Val Gly Leu Ser Ser Ala
             20                  25                  30

His Ala Val Glu Pro Pro Ala Ala Pro His Ala Pro Ala Val Val Ile
         35                  40                  45

Gly Ser Gly Tyr Gly Ala Ala Val Ala Ala Leu Arg Leu Gly Leu Ala
     50                  55                  60

Gly Val Pro Thr Leu Val Leu Glu Met Gly Arg Leu Trp Asp Thr Ala
 65                  70                  75                  80

Gly Pro Asp Gly Lys Val Phe Cys Pro Thr Ile Thr Pro Asp Arg Arg
                 85                  90                  95

Ser Met Trp Phe Arg Thr Arg Thr Glu Ala Pro Leu Ser Thr Phe Leu
             100                 105                 110

Trp Leu Asp Val Val Asn Arg Arg Ile Asp Pro Tyr Pro Gly Val Leu
         115                 120                 125

Asp Arg Val Asn Tyr Gly Asp Met Ser Val Tyr Val Gly Arg Gly Val
     130                 135                 140

Gly Gly Gly Ser Leu Val Asn Gly Gly Xaa Ala Val Thr Pro Pro Arg
145                 150                 155                 160

Pro Tyr Phe Ser Glu Val Leu Pro Gly Val Asp Ala Glu Ala Met Tyr
             165                 170                 175

Gly Thr Tyr Phe Pro Arg Ala Arg Arg Met Leu Gly Val Asn Glu Val
         180                 185                 190

Asp Arg Ser Trp Phe Glu Ser Thr Pro Trp Tyr Arg Phe Ser Arg Val
     195                 200                 205

Ser Arg Thr His Ala Ala Arg Ala Gly Leu Gly Thr Val Phe Xaa Pro
210                 215                 220

Asn Val Tyr Asp Phe Asp Tyr Met Arg Arg Glu Ala Ala Gly Glu Val
225                 230                 235                 240

Pro Arg Ser Ala Leu Ala Gly Glu Val Ile Tyr Gly Asn Asn His Gly
             245                 250                 255

Lys Arg Ser Leu Asp Arg Thr Tyr Leu Ala Ala Ala Leu Ala Thr Gly
         260                 265                 270

Arg Val Thr Val Glu Thr Met Ser Arg Val Arg Ala Leu Arg Pro Ala
     275                 280                 285

Asn Thr Gly Gly Thr Gly Gly Ala Gly Gly Tyr Val Leu Thr Val Glu
290                 295                 300

Arg Leu Asp Leu Ser Gly Arg Val Thr Ala Val Asp Glu Ile Thr Thr
305                 310                 315                 320

Gly Arg Leu Phe Leu Gly Ala Gly Ser Leu Gly Thr Thr Glu Leu Leu
             325                 330                 335

Leu Arg Ala Arg Glu Thr Gly Ala Leu Pro Asp Leu Asp Pro Glu Val
         340                 345                 350

Gly Arg Gly Trp Gly His Asn Gly Asn Val Met Thr Ala Arg Ala Asn
     355                 360                 365

His Leu Trp Asp Thr Val Gly Ala Gln Gln Ser Thr Met Pro Val Leu
370                 375                 380

Gly Ile Asp Asp Trp Asn Asn Pro Thr His Pro Val Xaa Ala Glu Ile
385                 390                 395                 400

Ala Pro Leu Pro Met Gly Leu Glu His Trp Ile Ser Leu Tyr Leu Ala
             405                 410                 415

Ile Thr Lys Asn Pro Glu Arg Gly His Phe Thr Tyr Asp Ala Ala Thr
         420                 425                 430

Asp Ser Ala Arg Leu Arg Trp Thr Arg Asp Gln Asn Glu Pro Ser Val
```

```
                  435                 440                 445
Ala Ala Ala Arg Ser Leu Phe Asp Arg Ile Asn Arg Ala Asn Gly Thr
        450                 455                 460

Ile His Arg Tyr Asp Leu Phe Gly Gly Asn Arg Lys Phe Ala Asp Asp
465                 470                 475                 480

Phe Thr Tyr His Pro Leu Gly Gly Cys Val Leu Gly Arg Ala Thr Asp
                485                 490                 495

Gly Tyr Gly Arg Ala Lys Gly His Pro Gly Leu Tyr Val Val Asp Gly
                500                 505                 510

Ser Leu Val Pro Gly Ser Ile Gly Val Asn Pro Phe Val Thr Ile Thr
        515                 520                 525

Ala Leu Ala Glu Arg Asn Met Glu Arg Ile Val Gln Glu Asp Ile Leu
        530                 535                 540

Gly
545

<210> SEQ ID NO 17
<211> LENGTH: 559
<212> TYPE: PRT
<213> ORGANISM: Streptomyces clavuligerus
<220> FEATURE:
<221> NAME/KEY: MISC_FEATURE
<222> LOCATION: (168)..(168)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (237)..(237)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (411)..(411)
<223> OTHER INFORMATION: Xaa is Phe, Trp, Ser, Thr, Lys, Ala, Asn, His
      or Asp, provided that when Xaa168 is Met, then Xaa411 is not Phe

<400> SEQUENCE: 17

Met Ala Leu Gly Ile Arg Pro Val Leu Val Asp Asp Gln His Met Thr
1               5                   10                  15

Pro His Leu Thr Arg Arg Gln Leu Met Gly Ala Ala Ala Leu Gln Thr
            20                  25                  30

Ala Ala Val Leu Gly Phe Thr Arg Val Gly Leu Ser Ser Ala His Ala
        35                  40                  45

Val Glu Pro Pro Ala Ala Pro His Ala Pro Ala Val Val Ile Gly Ser
    50                  55                  60

Gly Tyr Gly Ala Ala Val Ala Ala Leu Arg Leu Gly Leu Ala Gly Val
65                  70                  75                  80

Pro Thr Leu Val Leu Glu Met Gly Arg Leu Trp Asp Thr Ala Gly Pro
                85                  90                  95

Asp Gly Lys Val Phe Cys Pro Thr Ile Thr Pro Asp Arg Arg Ser Met
                100                 105                 110

Trp Phe Arg Thr Arg Thr Glu Ala Pro Leu Ser Thr Phe Leu Trp Leu
            115                 120                 125

Asp Val Val Asn Arg Arg Ile Asp Pro Tyr Pro Gly Val Leu Asp Arg
        130                 135                 140

Val Asn Tyr Gly Asp Met Ser Val Tyr Val Gly Arg Gly Val Gly Gly
145                 150                 155                 160

Gly Ser Leu Val Asn Gly Gly Xaa Ala Val Thr Pro Pro Arg Pro Tyr
                165                 170                 175
```

Phe Ser Glu Val Leu Pro Gly Val Asp Ala Glu Ala Met Tyr Gly Thr
            180                 185                 190

Tyr Phe Pro Arg Ala Arg Arg Met Leu Gly Val Asn Glu Val Asp Arg
        195                 200                 205

Ser Trp Phe Glu Ser Thr Pro Trp Tyr Arg Phe Ser Arg Val Ser Arg
210                 215                 220

Thr His Ala Ala Arg Ala Gly Leu Gly Thr Val Phe Xaa Pro Asn Val
225                 230                 235                 240

Tyr Asp Phe Asp Tyr Met Arg Arg Glu Ala Ala Gly Glu Val Pro Arg
                245                 250                 255

Ser Ala Leu Ala Gly Glu Val Ile Tyr Gly Asn Asn His Gly Lys Arg
            260                 265                 270

Ser Leu Asp Arg Thr Tyr Leu Ala Ala Ala Leu Ala Thr Gly Arg Val
        275                 280                 285

Thr Val Glu Thr Met Ser Arg Val Arg Ala Leu Arg Pro Ala Asn Thr
    290                 295                 300

Gly Gly Thr Gly Gly Ala Gly Gly Tyr Val Leu Thr Val Glu Arg Leu
305                 310                 315                 320

Asp Leu Ser Gly Arg Val Thr Ala Val Asp Glu Ile Thr Thr Gly Arg
                325                 330                 335

Leu Phe Leu Gly Ala Gly Ser Leu Gly Thr Thr Glu Leu Leu Leu Arg
            340                 345                 350

Ala Arg Glu Thr Gly Ala Leu Pro Asp Leu Asp Pro Glu Val Gly Arg
        355                 360                 365

Gly Trp Gly His Asn Gly Asn Val Met Thr Ala Arg Ala Asn His Leu
370                 375                 380

Trp Asp Thr Val Gly Ala Gln Gln Ser Thr Met Pro Val Leu Gly Ile
385                 390                 395                 400

Asp Asp Trp Asn Asn Pro Thr His Pro Val Xaa Ala Glu Ile Ala Pro
                405                 410                 415

Leu Pro Met Gly Leu Glu His Trp Ile Ser Leu Tyr Leu Ala Ile Thr
            420                 425                 430

Lys Asn Pro Glu Arg Gly His Phe Thr Tyr Asp Ala Ala Thr Asp Ser
        435                 440                 445

Ala Arg Leu Arg Trp Thr Arg Asp Gln Asn Glu Pro Ser Val Ala Ala
450                 455                 460

Ala Arg Ser Leu Phe Asp Arg Ile Asn Arg Ala Asn Gly Thr Ile His
465                 470                 475                 480

Arg Tyr Asp Leu Phe Gly Gly Asn Arg Lys Phe Ala Asp Asp Phe Thr
                485                 490                 495

Tyr His Pro Leu Gly Gly Cys Val Leu Gly Arg Ala Thr Asp Gly Tyr
            500                 505                 510

Gly Arg Ala Lys Gly His Pro Gly Leu Tyr Val Val Asp Gly Ser Leu
        515                 520                 525

Val Pro Gly Ser Ile Gly Val Asn Pro Phe Val Thr Ile Thr Ala Leu
    530                 535                 540

Ala Glu Arg Asn Met Glu Arg Ile Val Gln Glu Asp Ile Leu Gly
545                 550                 555

<210> SEQ ID NO 18
<211> LENGTH: 534
<212> TYPE: PRT
<213> ORGANISM: Saccharopolyspora erythraea
<220> FEATURE:
<221> NAME/KEY: MISC_FEATURE

```
<222> LOCATION: (151)..(151)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (220)..(220)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (388)..(388)
<223> OTHER INFORMATION: Xaa is Phe, Trp, Ser, Thr, Lys, Ala, Asn, His
      or Asp, provided that when Xaa151 is Met, then Xaa388 is not Phe

<400> SEQUENCE: 18

Met Thr Ser Ser Val Thr Arg Arg Arg Phe Leu Gly Met Ala Ala Met
1               5                   10                  15

Gln Ser Ala Ala Val Leu Gly Leu Gly Ala Val Ser Leu Gly Arg Ala
            20                  25                  30

Asp Ala Ala Glu Arg Pro Phe Val Pro Ala Val Val Gly Ser Gly
        35                  40                  45

Tyr Gly Ser Ala Ala Thr Ala Leu Arg Leu Gly Glu Ala Gly Val Ser
    50                  55                  60

Thr Leu Val Leu Glu Met Gly Arg Leu Trp Asp Arg Ala Gly Glu Asp
65                  70                  75                  80

Gly Ala Ile Phe Cys Ser Met Leu Gln Pro Asp His Arg Ala Met Trp
                85                  90                  95

Phe Lys Ala Arg Thr Glu Ala Pro Leu Ser Ser Leu Leu Trp Met Asp
            100                 105                 110

Leu Val Asn Arg Asp Ile Lys Pro Phe Ala Gly Val Leu Asp Arg Val
        115                 120                 125

His His Gly Asp Met Ser Val Tyr Val Gly Arg Gly Val Gly Gly Gly
    130                 135                 140

Ser Leu Val Asn Gly Gly Xaa Ala Val Thr Pro Arg Arg Gly Tyr Phe
145                 150                 155                 160

Glu Glu Val Leu Pro Arg Val Asp Ala Gly Glu Met Tyr Gly Arg Phe
            165                 170                 175

Phe Pro Leu Ala Asn Arg Met Leu Gly Val Asn Thr Val Asp Arg Thr
        180                 185                 190

Trp Phe Glu Glu Cys Glu Ser Tyr Arg Tyr Ala Arg Val Ser Arg Gly
    195                 200                 205

His Ala Gln Arg Ala Gly Leu Arg Thr Thr Phe Xaa Pro Asn Val Tyr
210                 215                 220

Asp Phe Gly Tyr Met Arg Arg Glu Glu Arg Gly Glu Val Pro Lys Ser
225                 230                 235                 240

Ala Leu Ser Ser Glu Val Ile Tyr Gly Asn Asn His Gly Lys Arg Ser
            245                 250                 255

Leu Asp Arg Ser Tyr Leu Pro Ala Ala Val Gly Thr Gly Asn Val Thr
        260                 265                 270

Ile Gln Ser Leu His Arg Val Arg Ser Phe Arg Gln Glu Pro Asp Gly
    275                 280                 285

Thr Tyr Val Leu Thr Val Glu Arg Ile Asp Glu Leu Gly Asn Met Leu
290                 295                 300

Gly Thr Thr Glu Ile Gly Cys Arg Trp Leu Phe Leu Gly Ala Gly Ser
305                 310                 315                 320

Met Gly Thr Thr Glu Leu Leu Leu Arg Ala Arg Glu Thr Gly Val Leu
            325                 330                 335
```

```
Pro Arg Leu Asp Asp Ser Val Gly His Gly Trp Gly Thr Asn Gly Asn
            340                 345                 350

Val Met Leu Gly Arg Ala Leu His Ser Trp Asp Arg Thr Gly Ser Val
        355                 360                 365

Gln Ser Gly Met Pro Ala Leu Gly Ile Asp Asn Trp Asp Asp Pro Val
    370                 375                 380

His Pro Val Xaa Ala Glu Ile Ala Pro Leu Pro Ala Gly Leu Glu Leu
385                 390                 395                 400

Leu Thr Ser Leu Ser Leu Ala Ile Thr Arg Asn Pro Glu Arg Gly Ser
            405                 410                 415

Phe Ser Tyr Asp Pro Ala Ala Asp Ala Ala Arg Leu His Trp Ser Ala
        420                 425                 430

Ser Gln Gly Lys Pro Ser Val Glu Ala Ala Lys Ala Leu Phe Asp Pro
    435                 440                 445

Ile Asn Arg Ala Asn Gly Thr Val Tyr Arg His Asp Leu Phe Gly Asp
        450                 455                 460

Ser Arg Ala Phe Glu Asp Arg Phe Thr Tyr His Pro Leu Gly Gly Cys
465                 470                 475                 480

Val Leu Gly Glu Ala Thr Asp Asp Phe Gly Arg Val Arg Gly Tyr Arg
            485                 490                 495

Asn Leu Tyr Val Thr Asp Gly Ser Leu Ile Pro Gly Ser Thr Gly Val
        500                 505                 510

Asn Pro Phe Val Thr Ile Thr Ala Leu Ala Glu Arg Asn Ile Asp Arg
            515                 520                 525

Val Leu Ser Glu Asp Phe
            530
```

<210> SEQ ID NO 19
<211> LENGTH: 544
<212> TYPE: PRT
<213> ORGANISM: Streptomyces avermitilis
<220> FEATURE:
<221> NAME/KEY: MISC_FEATURE
<222> LOCATION: (159)..(159)
<223> OTHER INFORMATION: Xaa is Met, Phe, Leu, Val, Cys, Ile, Ala, Gln, Tyr, Lys or Ser
<220> FEATURE:
<221> NAME/KEY: MISC_FEATURE
<222> LOCATION: (228)..(228)
<223> OTHER INFORMATION: Xaa is Val, Met, Ile, Ala, Thr, Lys, Cys, Ser, Gly, Glu, Tyr, Pro, Asn, Gln, Trp or His
<220> FEATURE:
<221> NAME/KEY: MISC_FEATURE
<222> LOCATION: (396)..(396)
<223> OTHER INFORMATION: Xaa is Phe, Trp, Ser, Thr, Lys, Ala, Asn, His or Asp, provided that when Xaa159 is Met, then Xaa396 is not Phe

<400> SEQUENCE: 19

```
Met Thr Glu Lys Leu Thr His Arg His Leu Thr Arg Arg Gln Ile Leu
1               5                   10                  15

Gly Met Ala Ala Leu Gln Thr Ala Thr Leu Gly Phe Thr Arg Ile
            20                  25                  30

Gly Leu Gln Ser Ala Arg Ala Ala Glu Pro Asp Ala Val Glu Thr Ala
        35                  40                  45

Pro Ala Ile Val Val Gly Ser Gly Tyr Gly Ala Ala Val Ala Ala Leu
    50                  55                  60

Arg Leu Gly Gln Ala Gly Leu Arg Thr Leu Val Ile Glu Met Gly Gly
65                  70                  75                  80

Leu Trp Asn Thr Pro Gly Ser Asp Gly Lys Val Phe Cys Ser Thr Ser
            85                  90                  95
```

-continued

```
Ala Pro Asp Arg Arg Ser Met Trp Phe Arg Thr Arg Thr Glu Ala Pro
            100                 105                 110
Leu Ala Glu Phe Leu Trp Leu Asp Val Val Asn Lys Asp Ile Ser Pro
        115                 120                 125
Tyr Pro Gly Val Leu Asp Arg Val His Phe Ala Asn Met Ser Val Tyr
    130                 135                 140
Val Gly Arg Gly Val Gly Gly Ser Leu Val Asn Gly Gly Xaa Ala
145                 150                 155                 160
Val Thr Pro Leu Gln Ser Tyr Phe Ala Glu Gln Phe Pro Thr Val Asp
                165                 170                 175
Ala Ala Glu Met Tyr Ser Thr Tyr Phe Pro Arg Ala Arg Thr Met Leu
            180                 185                 190
Gly Val Asn Thr Val Asp Pro Ala Trp Phe Glu Ser Thr Glu Trp Tyr
        195                 200                 205
Arg Phe Thr Arg Thr Ser Arg Lys Ala Ala Thr Asn Thr Gly Leu Lys
    210                 215                 220
Thr Thr Phe Xaa Pro Asn Val Tyr Asp Phe Gly Tyr Met Gln Arg Glu
225                 230                 235                 240
Ala Ala Gly Thr Ala Thr Lys Ser Ala Leu Ala Gly Glu Val Ile Tyr
                245                 250                 255
Gly Asn Asn Tyr Gly Lys Arg Ser Leu Asp Lys Thr Tyr Leu Ala Ser
            260                 265                 270
Ala Leu Gly Thr Gly Asn Val Thr Ile His Thr Leu Glu Arg Val Arg
        275                 280                 285
Glu Ile Arg Arg Ala Ser Asp Gly Thr Tyr Leu Leu Thr Ala Asp Arg
    290                 295                 300
Ile Asp Thr Thr Gly Ala Val Val Glu Thr Lys Gln Tyr Ser Cys Thr
305                 310                 315                 320
Tyr Leu Phe Leu Gly Gly Ser Leu Gly Thr Ser Glu Leu Leu Val
                325                 330                 335
Arg Ala Arg Glu Thr Gly Ala Leu Pro Ala Leu Asp Ala Ser Val Gly
            340                 345                 350
Thr Gly Trp Gly Thr Asn Gly Asn Val Met Thr Gly Arg Ala Asn His
        355                 360                 365
Ile Trp Asp Thr Val Gly Ala Asn Gln Ser Thr Met Pro Val Met Gly
    370                 375                 380
Ile Asp Asp Trp Ala Asn Thr Ser Asn Pro Val Xaa Ala Glu Ile Ala
385                 390                 395                 400
Pro Leu Pro Met Gly Leu Glu His Trp Ile Ser Leu Tyr Leu Ala Ile
                405                 410                 415
Thr Lys Asn Pro Glu Arg Ala Ser Phe Thr Tyr Asp Ala Ala Ser Asp
            420                 425                 430
Ser Ala Lys Leu Gly Trp Ser Ala Ala Gln Ser Ala Val Ser Val Ser
        435                 440                 445
Met Ala Lys Lys Leu Phe Asp Arg Ile Asn Ser Ala Asn Ala Thr Ile
    450                 455                 460
Tyr Arg Tyr Asp Leu Phe Gly Asn Asn Lys Thr Phe Ala Asp Asp Phe
465                 470                 475                 480
Thr Tyr His Pro Leu Gly Gly Cys Val Leu Gly Lys Ser Thr Asp Asn
                485                 490                 495
Tyr Gly Arg Val Lys Gly Tyr Ser Lys Leu Tyr Val Thr Asp Gly Ser
            500                 505                 510
```

-continued

```
Leu Val Pro Gly Ser Ile Gly Val Asn Pro Phe Val Thr Ile Thr Ala
            515                 520                 525

Leu Ala Glu Arg Thr Met Ala Arg Val Leu Ala Glu Asp Thr Ala Pro
        530                 535                 540

<210> SEQ ID NO 20
<211> LENGTH: 522
<212> TYPE: PRT
<213> ORGANISM: Saccharopolyspora erythraea
<220> FEATURE:
<221> NAME/KEY: MISC_FEATURE
<222> LOCATION: (139)..(139)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (208)..(208)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (376)..(376)
<223> OTHER INFORMATION: Xaa is Phe, Trp, Ser, Thr, Lys, Ala, Asn, His
      or Asp, provided that when Xaa139 is Met, then Xaa376 is not Phe

<400> SEQUENCE: 20

Met Ala Ala Met Gln Ser Ala Ala Val Leu Gly Leu Gly Ala Val Ser
1               5                  10                  15

Leu Gly Arg Ala Asp Ala Ala Glu Arg Pro Phe Val Pro Ala Val Val
            20                  25                  30

Val Gly Ser Gly Tyr Gly Ser Ala Ala Thr Ala Leu Arg Leu Gly Glu
        35                  40                  45

Ala Gly Val Ser Thr Leu Val Leu Glu Met Gly Arg Leu Trp Asp Arg
    50                  55                  60

Ala Gly Glu Asp Gly Ala Ile Phe Cys Ser Met Leu Gln Pro Asp His
65                  70                  75                  80

Arg Ala Met Trp Phe Lys Ala Arg Thr Glu Ala Pro Leu Ser Ser Leu
                85                  90                  95

Leu Trp Met Asp Leu Val Asn Arg Asp Ile Lys Pro Phe Ala Gly Val
            100                 105                 110

Leu Asp Arg Val His His Gly Asp Met Ser Val Tyr Val Gly Arg Gly
        115                 120                 125

Val Gly Gly Gly Ser Leu Val Asn Gly Gly Xaa Ala Val Thr Pro Arg
    130                 135                 140

Arg Gly Tyr Phe Glu Glu Val Leu Pro Arg Val Asp Ala Gly Glu Met
145                 150                 155                 160

Tyr Gly Arg Phe Phe Pro Leu Ala Asn Arg Met Leu Gly Val Asn Thr
                165                 170                 175

Val Asp Arg Thr Trp Phe Glu Glu Cys Glu Ser Tyr Tyr Ala Arg
            180                 185                 190

Val Ser Arg Gly His Ala Gln Arg Ala Gly Leu Arg Thr Thr Phe Xaa
        195                 200                 205

Pro Asn Val Tyr Asp Phe Gly Tyr Met Arg Arg Glu Glu Arg Gly Glu
    210                 215                 220

Val Pro Lys Ser Ala Leu Ser Ser Glu Val Ile Tyr Gly Asn Asn His
225                 230                 235                 240

Gly Lys Arg Ser Leu Asp Arg Ser Tyr Leu Pro Ala Ala Val Gly Thr
                245                 250                 255

Gly Asn Val Thr Ile Gln Ser Leu His Arg Val Arg Ser Phe Arg Gln
            260                 265                 270
```

```
Glu Pro Asp Gly Thr Tyr Val Leu Thr Val Glu Arg Ile Asp Glu Leu
            275                 280                 285

Gly Asn Met Leu Gly Thr Thr Glu Ile Gly Cys Arg Trp Leu Phe Leu
290                 295                 300

Gly Ala Gly Ser Met Gly Thr Thr Glu Leu Leu Leu Arg Ala Arg Glu
305                 310                 315                 320

Thr Gly Val Leu Pro Arg Leu Asp Asp Ser Val Gly His Gly Trp Gly
                325                 330                 335

Thr Asn Gly Asn Val Met Leu Gly Arg Ala Leu His Ser Trp Asp Arg
                340                 345                 350

Thr Gly Ser Val Gln Ser Gly Met Pro Ala Leu Gly Ile Asp Asn Trp
            355                 360                 365

Asp Asp Pro Val His Pro Val Xaa Ala Glu Ile Ala Pro Leu Pro Ala
            370                 375                 380

Gly Leu Glu Leu Leu Thr Ser Leu Ser Leu Ala Ile Thr Arg Asn Pro
385                 390                 395                 400

Glu Arg Gly Ser Phe Ser Tyr Asp Pro Ala Ala Asp Ala Ala Arg Leu
                405                 410                 415

His Trp Ser Ala Ser Gln Gly Lys Pro Ser Val Glu Ala Ala Lys Ala
                420                 425                 430

Leu Phe Asp Pro Ile Asn Arg Ala Asn Gly Thr Val Tyr Arg His Asp
            435                 440                 445

Leu Phe Gly Asp Ser Arg Ala Phe Glu Asp Arg Phe Thr Tyr His Pro
            450                 455                 460

Leu Gly Gly Cys Val Leu Gly Glu Ala Thr Asp Phe Gly Arg Val
465                 470                 475                 480

Arg Gly Tyr Arg Asn Leu Tyr Val Thr Asp Gly Ser Leu Ile Pro Gly
                485                 490                 495

Ser Thr Gly Val Asn Pro Phe Val Thr Ile Thr Ala Leu Ala Glu Arg
                500                 505                 510

Asn Ile Asp Arg Val Leu Ser Glu Asp Phe
            515                 520

<210> SEQ ID NO 21
<211> LENGTH: 547
<212> TYPE: PRT
<213> ORGANISM: Streptomyces hygroscopicus
<220> FEATURE:
<221> NAME/KEY: MISC_FEATURE
<222> LOCATION: (161)..(161)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (230)..(230)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (398)..(398)
<223> OTHER INFORMATION: Xaa is Phe, Trp, Ser, Thr, Lys, Ala, Asn, His
      or Asp, provided that when Xaa161 is Ile, then Xaa398 is not Phe

<400> SEQUENCE: 21

Met Ser His Ser Ala His Asp Ala Ala Met Glu Gly Lys Leu Thr Arg
1               5                   10                  15

Arg His Phe Leu Gly Leu Ala Ala Leu Gln Thr Ala Ala Ala Leu Gly
            20                  25                  30

Leu Thr Arg Ile Gly Leu Thr Pro Ala Ala Ala Ala Gln Ser Ala Asp
```

```
                35                  40                  45
His Thr Pro Ala Leu Val Ile Gly Ser Gly Tyr Gly Ala Val Ala
 50                  55                  60

Ala Leu Arg Leu Gly Glu Ala Gly Ile Arg Thr Leu Val Ile Glu Met
 65                  70                  75                  80

Gly Arg Leu Trp Glu Ala Pro Asp Ser Gly Thr Val Phe Cys Ser
                 85                  90                  95

Met Thr Ala Pro Asp Gln Arg Ser Met Trp Phe Lys Arg Arg Thr Glu
                100                 105                 110

Ala Pro Leu Ser Thr Phe Leu Trp Leu Asp Val Ile Asn Lys Asp Ile
            115                 120                 125

Thr Pro Tyr Pro Gly Val Leu Asp Arg Val Arg His Pro Asn Met Ser
130                 135                 140

Val Tyr Val Gly Arg Gly Val Gly Gly Ser Leu Val Asn Gly Gly
145                 150                 155                 160

Xaa Ala Val Thr Pro Pro Arg Ala Tyr Phe Gln Glu Val Leu Pro Gly
                165                 170                 175

Val Asp Ala Asp Ala Met Tyr Gly Thr Tyr Phe Pro Arg Ala Asn Arg
            180                 185                 190

Met Leu Gly Thr Ala Thr Ile Pro Ser Asp Trp Phe Glu Gly Thr Glu
        195                 200                 205

Trp Tyr Gln Tyr Ala Arg Val Ala Arg Ala Gln Ala Ser Ala Ala Gly
210                 215                 220

Leu Lys Thr Val Phe Xaa Pro Ser Val Tyr Asp Phe Asp Tyr Met Arg
225                 230                 235                 240

Arg Glu Ala Ala Gly Thr Ala Thr Lys Ser Ala Leu Ala Gln Glu Val
                245                 250                 255

Ile Tyr Gly Asn Asn His Gly Lys Arg Ser Leu Asp Lys Thr Tyr Leu
            260                 265                 270

Ala Ala Ala Leu Gly Thr Gly Asn Val Thr Ile His Thr Leu Ser Arg
        275                 280                 285

Ala Arg Ala Ile Arg Arg Ala Ala Asp Gly Ser Tyr Thr Val Thr Val
    290                 295                 300

Asp Arg Ile Asp Thr Thr Gly Ala Val Thr Ala Thr Asp Glu Ile Ser
305                 310                 315                 320

Cys Arg Ala Leu Phe Leu Gly Ala Gly Ser Leu Gly Thr Thr Glu Leu
                325                 330                 335

Leu Leu Arg Ala Arg Glu Thr Gly Thr Leu Pro Gly Leu Asn Ala Glu
            340                 345                 350

Val Gly Arg Gly Trp Gly Gly Asn Gly Asn Val Met Leu Gly Arg Ala
        355                 360                 365

Asn His Val Trp Asn Pro Thr Gly Ala His Gln Ser Thr Ile Pro Val
370                 375                 380

Thr Ala Ile Asp Asp Trp Ser Asn Ala Ala Asn Pro Val Xaa Ala Glu
385                 390                 395                 400

Ile Ala Pro Leu Pro Ala Gly Thr Glu Thr Trp Ala Ser Leu Tyr Leu
                405                 410                 415

Ala Ile Thr Lys Asn Pro Glu Arg Gly Thr Phe Thr Tyr Asp Ala Ala
            420                 425                 430

Lys Asp Ala Ala Val Leu Asn Trp Thr Ala Gly Gln Ser Ala Pro Ala
        435                 440                 445

Ile Ala Ala Ala Lys Ala Leu Phe Asp Arg Val Asn Ala Ala Asn Val
    450                 455                 460
```

```
Thr Ile Tyr Arg Tyr Asp Leu Phe Gly Asp Thr Arg Ala Phe Ala Ala
465                 470                 475                 480

Asp Phe Cys Tyr His Pro Leu Gly Gly Cys Val Leu Gly Arg Ala Thr
                485                 490                 495

Asp Ala Tyr Gly Arg Val Ala Gly Tyr Pro Arg Leu Tyr Val Thr Asp
            500                 505                 510

Gly Ser Leu Ile Pro Gly Ser Ile Gly Val Asn Pro Phe Val Thr Ile
        515                 520                 525

Thr Ala Leu Ala Glu Arg Thr Met Ala Arg Val Leu Ala Glu Asp Asp
    530                 535                 540

Val Gly Arg
545

<210> SEQ ID NO 22
<211> LENGTH: 545
<212> TYPE: PRT
<213> ORGANISM: Streptomyces viridochromogenes
<220> FEATURE:
<221> NAME/KEY: MISC_FEATURE
<222> LOCATION: (159)..(159)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (228)..(228)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (396)..(396)
<223> OTHER INFORMATION: Xaa is Phe, Trp, Ser, Thr, Lys, Ala, Asn, His
      or Asp, provided that when Xaa159 is Met, then Xaa396 is not Phe

<400> SEQUENCE: 22

Met Thr Val Lys Leu Met Gln Arg Gln Leu Thr Arg Arg Gln Ile Leu
1               5                   10                  15

Gly Met Val Ala Leu Gln Gly Ala Ala Ala Gly Leu Thr Arg Ile
            20                  25                  30

Gly Leu Gln Val Ala Ser Ala Ala Glu Pro Ala Ala Val Asp Asn Ala
        35                  40                  45

Pro Ala Ile Val Val Gly Ser Gly Tyr Gly Gly Ala Val Ala Ala Leu
    50                  55                  60

Arg Leu Gly Gln Ala Gly Ile Arg Thr Leu Val Leu Glu Met Gly Arg
65                  70                  75                  80

Leu Trp Asn Thr Pro Gly Pro Asp Gly Lys Val Phe Cys Ser Thr Arg
                85                  90                  95

Thr Pro Asp Gln Arg Ser Met Trp Phe Arg Thr Arg Thr Glu Ala Pro
            100                 105                 110

Leu Ala Thr Phe Leu Trp Leu Asp Leu Val Asn Gln Asp Ile Ser Ser
        115                 120                 125

Tyr Pro Gly Val Leu Asp Arg Val His Tyr Asp His Met Ser Val Tyr
    130                 135                 140

Val Gly Arg Gly Val Gly Gly Ser Leu Val Asn Gly Gly Xaa Ala
145                 150                 155                 160

Val Thr Pro Leu Arg Ser Tyr Phe Ala Glu Gln Phe Pro Thr Val Asp
                165                 170                 175

Thr Ala Glu Met Tyr Asp Thr Tyr Phe Pro Arg Ala Arg Ser Met Leu
            180                 185                 190

Gly Val Asn Thr Val Asp Pro Ala Trp Phe Glu Ser Thr Glu Trp Tyr
```

```
            195                 200                 205
Arg Phe Thr Arg Ile Ser Arg Lys His Ala Asp Asn Ala Gly Leu Lys
    210                 215                 220

Thr Thr Phe Xaa Pro Asn Val Tyr Asp Phe Gly His Met Glu Arg Glu
225                 230                 235                 240

Ala Ala Gly Thr Ala Thr Lys Ser Ala Leu Ala Gly Glu Val Ile Tyr
                245                 250                 255

Gly Asn Asn Gln Gly Lys Arg Ser Leu Asp Lys Thr Tyr Leu Ala Ser
                260                 265                 270

Ala Leu Gly Thr Gly Asn Val Thr Leu His Thr Met Glu Arg Val Thr
            275                 280                 285

Ser Ile Ser Arg Ala Ala Asp Gly Thr Tyr Leu Leu Thr Ala Asp Arg
        290                 295                 300

Ile Asp Asp Thr Gly Thr Val Val Glu Thr Lys Glu Tyr Ala Cys Thr
305                 310                 315                 320

Tyr Leu Phe Leu Gly Gly Gly Ser Ile Gly Thr Thr Glu Leu Leu Val
                325                 330                 335

Arg Ala Arg Glu Ser Gly Thr Leu Pro Arg Leu Asp Ala Ser Val Gly
                340                 345                 350

Thr Gly Trp Gly Thr Asn Gly Asn Val Met Leu Gly Arg Ala Asn His
            355                 360                 365

Val Trp Asp Thr Val Gly Ala Asn Gln Ser Thr Met Pro Val Met Gly
        370                 375                 380

Ile Asp Asp Trp Ala Asn Thr Ala Asn Pro Val Xaa Ala Glu Ile Ala
385                 390                 395                 400

Pro Leu Pro Met Gly Leu Glu His Trp Val Ser Leu Tyr Leu Ala Ile
                405                 410                 415

Thr Lys Asn Pro Glu Arg Ala Ser Phe Thr Tyr Asp Pro Ala Ser Gly
                420                 425                 430

Ala Val Arg Leu Gly Trp Ser Ala Ala Gln Ser Ala Val Ser Val Gly
            435                 440                 445

Met Ala Lys Lys Leu Phe Asp Arg Ile Asn Lys Ala Asn Ala Thr Ile
        450                 455                 460

Tyr Arg Tyr Asp Leu Phe Gly Ser Ser Asn Lys Val Phe Ala Asp Asp
465                 470                 475                 480

Phe Thr Tyr His Pro Leu Gly Gly Cys Val Leu Gly Arg Ser Thr Asp
                485                 490                 495

Ala Tyr Gly Arg Val Lys Gly Tyr Ser Arg Leu Tyr Val Thr Asp Gly
                500                 505                 510

Ser Leu Val Pro Gly Ser Ile Gly Val Asn Pro Phe Val Thr Ile Thr
            515                 520                 525

Ala Leu Ala Glu Arg Thr Met Ala Arg Val Leu Ala Glu Asp Thr Ala
        530                 535                 540

Pro
545

<210> SEQ ID NO 23
<211> LENGTH: 531
<212> TYPE: PRT
<213> ORGANISM: Microscilla marina
<220> FEATURE:
<221> NAME/KEY: MISC_FEATURE
<222> LOCATION: (146)..(146)
<223> OTHER INFORMATION: Xaa is Met, Phe, Leu, Val, Cys, Ile, Ala, Gln,
      Tyr, Lys,or Ser
<220> FEATURE:
```

```
<221> NAME/KEY: MISC_FEATURE
<222> LOCATION: (215)..(215)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (383)..(383)
<223> OTHER INFORMATION: Xaa is Phe, Trp, Ser, Thr, Lys, Ala, Asn, His
      or Asp, provided that when Xaa146 is Met, then Xaa383 is not Phe

<400> SEQUENCE: 23

Met Gly Ser Ala Ser Val Met Gly Leu Thr Thr Ile Ser Leu Ala Asn
1               5                   10                  15

Cys Phe Asn Pro Thr Leu Pro Gln Lys Glu Lys Asn Arg Asn Glu Thr
            20                  25                  30

Thr His Phe Thr Ser Ile Val Ile Gly Thr Gly Tyr Gly Gly Ala Val
        35                  40                  45

Ser Ala Leu Arg Leu Gly Glu Ala Gly Val Asp Thr Leu Met Leu Glu
    50                  55                  60

Met Gly Gln Leu Trp Asp Lys Pro Gly Pro Asp Gly Lys Val Phe Cys
65                  70                  75                  80

Lys Met Thr Lys Pro Asp Gly Arg Ala Met Trp Phe Lys Asn Arg Thr
                85                  90                  95

Glu Ala Pro Leu Ser Ser Phe Leu Trp Ile Asp Ala Ile Asn Arg Pro
            100                 105                 110

Ile Asp Tyr Tyr Ala Gly Val Leu Asp Arg Ile Asn Tyr Pro Asn Met
        115                 120                 125

Ser Val Tyr Val Gly Arg Gly Val Gly Gly Ser Leu Val Asn Gly
    130                 135                 140

Gly Xaa Ala Val Thr Pro Pro Met Asn Tyr Phe Gln Glu Ile Leu Pro
145                 150                 155                 160

Glu Val Asn Thr His Glu Met Tyr Asn Lys Tyr Phe Pro Arg Ala Asn
                165                 170                 175

Gln Lys Leu Gln Val Asn Thr Ile Pro Asn Thr Leu Leu Glu Asn Ser
            180                 185                 190

Pro Tyr Tyr Arg Phe Thr Arg Val Gly Arg Gln Gln Ala Glu Lys Ala
        195                 200                 205

Gly Phe Lys Thr Val Thr Xaa Pro Asn Ile Tyr Asp Tyr Asn Tyr Met
    210                 215                 220

Gln Gln Glu Glu Ala Gly Lys Val His Lys Ser Ala Phe Gly Lys Glu
225                 230                 235                 240

Val Ile Tyr Gly Asn Asn Gly Gly Lys Arg Ser Leu Asp Lys Thr Tyr
                245                 250                 255

Leu Ala Asp Ala Leu Gly Thr Gly Lys Val Thr Leu Lys Tyr Leu His
            260                 265                 270

Arg Val Asp Ala Ile Thr Gln Asn Ser Gln Gly Leu Tyr Gln Ile Asp
        275                 280                 285

Val Ser Glu Ile Asn Thr Ser Gly Ala Thr Val Ala Lys Lys Thr Phe
    290                 295                 300

Thr Cys Lys His Leu Phe Met Cys Ala Gly Ser Val Gly Ser Thr Glu
305                 310                 315                 320

Met Leu Val Arg Ala Arg Glu Thr Gly Lys Leu Pro Ser Leu Pro Ser
                325                 330                 335

Glu Val Gly Thr His Trp Gly Asn Asn Gly Asn Val Met Thr Ala Arg
            340                 345                 350

Ala Asn His Met Trp His Pro Thr Gly Thr Lys Gln Ser Thr Ile Pro
```

```
                355                 360                 365
Ala Met Gly Ile Asn Asp Trp Asp Asn Ala Ser Asn Pro Val Xaa Ala
    370                 375                 380

Glu Ile Ala Pro Leu Pro Thr Gly Phe Glu Thr Trp Ile Ser Leu Tyr
385                 390                 395                 400

Leu Ala Ile Thr Lys Asn Pro Glu Arg Gly His Phe Glu Tyr Asp Ala
                405                 410                 415

Thr Lys Gln Gln Ala Val Leu Arg Trp Gly Ala His Gln Ser Gln Pro
            420                 425                 430

Ser Ile Asn Ser Ala Lys Ala Met Phe Asp Lys Ile Asn Lys Ala Asn
        435                 440                 445

Thr Thr Ile Tyr Arg Tyr Asp Leu Phe Gly Asn Asn Lys Ala Phe Ala
    450                 455                 460

Asp Asp Phe Thr Tyr His Pro Leu Gly Gly Cys Val Leu Gly Lys Ala
465                 470                 475                 480

Thr Asp Leu Tyr Gly Arg Ile Lys Gly Tyr Ser Asn Leu Tyr Val Asn
                485                 490                 495

Asp Gly Ala Leu Val Pro Gly Asn Thr Gly Val Asn Pro Phe Ile Thr
            500                 505                 510

Ile Thr Ala Met Ala Glu Arg Asn Ile Glu Lys Ile Ile Gln Glu Asp
        515                 520                 525

Met Leu Lys
    530

<210> SEQ ID NO 24
<211> LENGTH: 541
<212> TYPE: PRT
<213> ORGANISM: Kribbella flavida
<220> FEATURE:
<221> NAME/KEY: MISC_FEATURE
<222> LOCATION: (157)..(157)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (226)..(226)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (393)..(393)
<223> OTHER INFORMATION: Xaa is Phe, Trp, Ser, Thr, Lys, Ala, Asn, His
      or Asp, provided that when Xaa157 is Met, then Xaa393 is not Phe

<400> SEQUENCE: 24

Met Thr Ala Ser Asn Glu Thr Asn Gln Ser Val Val Thr Arg Arg Arg
1               5                   10                  15

Phe Ala Gly Leu Ala Ala Phe Thr Ser Ala Ala Ala Leu Gly Leu Ser
            20                  25                  30

Arg Val Gly Asp Ala Val Ala Ala Glu Arg Ser Phe Val Pro Ala Val
        35                  40                  45

Val Val Gly Thr Gly Tyr Gly Ala Ala Val Thr Ala Leu Arg Leu Gly
    50                  55                  60

Glu Ala Gly Val Ala Thr Thr Met Leu Glu Met Gly Gln Pro Trp Asn
65                  70                  75                  80

Gln Pro Gly Ala Asp Gly Lys Val Phe Cys Ser Thr Leu Ala Pro Asp
                85                  90                  95

Arg Arg Ser Met Trp Phe His Arg Thr Ala Ala Pro Leu Asp Thr
            100                 105                 110
```

```
Phe Leu Trp Leu Asp Val Val Asn Arg Asp Leu Gly Thr Pro Tyr Ala
            115                 120                 125
Gly Val Leu Asp Arg Ile Asp Phe Pro Ala Met Asp Val Tyr Val Gly
        130                 135                 140
Arg Gly Val Gly Gly Ser Leu Val Asn Gly Gly Xaa Ala Pro Thr
145                 150                 155                 160
Pro Arg Arg Ser Tyr Phe Glu Gln Val Leu Pro Arg Val Asp Ala Asp
                165                 170                 175
Gln Met Tyr Arg Arg Trp Phe Pro Leu Ala Asn Arg Met Leu Gly Val
            180                 185                 190
Asn Ser Ile Asp Pro Arg Tyr Leu Glu Thr Thr Pro Ala Tyr Arg Tyr
        195                 200                 205
Ala Arg Val Ser Arg Arg His Ala His Gln Ala Gly Phe Arg Thr Ala
210                 215                 220
Val Xaa Pro Asn Val Tyr Asp Phe Gly Tyr Leu Glu Gln Glu Glu Arg
225                 230                 235                 240
Arg Gln Val Pro Arg Ser Ala Leu Ala Gly Glu Val Ile Tyr Gly Asn
                245                 250                 255
Asn His Gly Lys Gln Ser Leu Asp Lys Thr Tyr Leu Ala Asp Ala Val
            260                 265                 270
Gly Thr Gly Arg Val Thr Ile Arg Thr Leu Thr Arg Val Val Ser Val
        275                 280                 285
Arg Ala Asp Arg Arg Gly Tyr Val Leu Gly Leu Glu Gln Ile Asp Ala
290                 295                 300
Ser Gly Lys Val Val Arg Arg Ser Glu Leu Gly Cys Arg Gln Leu Phe
305                 310                 315                 320
Leu Gly Ala Gly Ser Ile Gly Thr Thr Glu Leu Leu Leu Arg Ala Arg
                325                 330                 335
Glu Thr Gly Thr Leu Pro Asp Leu Pro Asp Ala Ile Gly Glu Gly Trp
            340                 345                 350
Gly Thr Asn Gly Asn Val Met Thr Ala Arg Ala Asn His Ala Trp Asp
        355                 360                 365
Pro Thr Gly Ser Leu Gln Ser Thr Ile Pro Ala Val Ala Ile Asp Asn
370                 375                 380
Trp Asp Asp Pro Val His Pro Ala Xaa Ala Glu Ile Ala Pro Leu Pro
385                 390                 395                 400
Thr Gly Leu Glu Thr Trp Ala Gly Leu Tyr Leu Ala Ile Thr Ala Asn
                405                 410                 415
Pro Glu Arg Gly Arg Leu Ser Tyr Asp His Ala Thr Arg Ala Ile
            420                 425                 430
Leu His Trp Gln Ala Ser Gln Ser Thr Pro Ser Ile Gln Ala Ala Lys
        435                 440                 445
Ala Leu Phe Asp Arg Ile Asn Arg Ala Thr Gly Thr Thr Tyr Arg Arg
450                 455                 460
Asp Leu Phe Ser Gly Asn Arg Ala Phe Ala Asp Phe Cys Tyr His
465                 470                 475                 480
Pro Leu Gly Gly Cys Val Leu Gly Arg Ala Thr Asp Tyr Gly Arg
                485                 490                 495
Val Arg Gly His Arg Asn Leu Tyr Val Thr Asp Ser Ala Leu Leu Pro
            500                 505                 510
Gly Ser Ile Gly Val Asn Pro Phe Val Thr Ile Thr Ala Leu Ala Glu
        515                 520                 525
Arg Asn Ile Ala Arg Val Ile Ala Thr Asp Leu Thr Arg
```

-continued

<210> SEQ ID NO 25
<211> LENGTH: 543
<212> TYPE: PRT
<213> ORGANISM: Streptomyces sviceus
<220> FEATURE:
<221> NAME/KEY: MISC_FEATURE
<222> LOCATION: (159)..(159)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (228)..(228)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (396)..(396)
<223> OTHER INFORMATION: Xaa is Phe, Trp, Ser, Thr, Lys, Ala, Asn, His
      or Asp, provided that when Xaa159 is Met, then Xaa396 is not Phe

<400> SEQUENCE: 25

```
Met Ala Thr Lys Leu Ile Gln Arg Gln Leu Thr Arg Arg Gln Ile Leu
  1               5                  10                  15

Gly Met Ala Ala Leu Gln Thr Ala Thr Leu Gly Phe Thr Arg Val
             20                  25                  30

Gly Leu Gln Ser Ala Arg Ala Asp Glu Pro Ala Ala Val Glu Ser Ala
         35                  40                  45

Pro Ala Ile Val Val Gly Ser Gly Tyr Gly Ala Ser Val Ala Ala Leu
     50                  55                  60

Arg Leu Gly Gln Ala Gly Ile Arg Thr Leu Val Leu Glu Met Gly Arg
 65                  70                  75                  80

Leu Trp Asn Thr Ala Gly Pro Asp Gly Lys Val Phe Cys Asn Thr Ala
                 85                  90                  95

Asn Pro Asp Gln Arg Ser Met Trp Phe Arg Thr Arg Thr Glu Ala Pro
            100                 105                 110

Leu Ala Thr Phe Leu Trp Leu Asp Val Val Asn Lys Asp Val Ser Pro
        115                 120                 125

Tyr Pro Gly Val Leu Asp Arg Val His Phe Asp His Met Ser Val Phe
    130                 135                 140

Val Gly Arg Gly Val Gly Gly Ser Leu Val Asn Gly Ser Xaa Ala
145                 150                 155                 160

Val Thr Pro Leu Gln Ser Tyr Phe Ala Glu Gln Phe Pro Thr Val Asp
                165                 170                 175

Thr Ala Glu Met Tyr Gly Thr Tyr Phe Pro Arg Ala Arg Ala Met Leu
            180                 185                 190

Gly Val Asn Thr Ile Asp Pro Ala Trp Phe Glu Ser Thr Glu Trp Tyr
        195                 200                 205

Lys Phe Thr Arg Val Ser Arg Lys His Ala Gln Asn Thr Gly Leu Lys
    210                 215                 220

Thr Thr Phe Xaa Pro Ser Val Tyr Asp Phe Gly Tyr Met Gln Arg Glu
225                 230                 235                 240

Ala Ala Gly Thr Ala Thr Lys Ser Ala Leu Gly Gln Glu Val Ile Tyr
                245                 250                 255

Gly Asn Asn Phe Gly Lys Lys Ser Leu Asp Lys Thr Tyr Leu Ala Ser
            260                 265                 270

Ala Leu Gly Thr Gly Asn Val Thr Ile His Thr Met Glu Lys Val Thr
        275                 280                 285
```

```
Gly Ile Ser Arg Ala Gly Asp Gly Ser Trp Val Leu Ser Ala Glu Arg
            290                 295                 300

Ile Asp Tyr Ser Gly Ala Val Glu Thr Lys Gln Tyr Ser Cys Thr
305                 310                 315                 320

Tyr Leu Phe Leu Gly Gly Ser Leu Gly Thr Ser Glu Leu Leu Leu
                325                 330                 335

Arg Ser Arg Gln Ser Gly Thr Leu Pro Ala Leu Asp Ala Ser Val Gly
            340                 345                 350

Ala Gly Trp Gly Pro Asn Gly Asn Thr Met Leu Gly Arg Ala Asn His
            355                 360                 365

Leu Trp Asp Thr Val Gly Ala Asn Gln Ser Thr Met Pro Val Met Gly
370                 375                 380

Ile Asp Asp Trp Ala Asn Thr Asp Asn Pro Val Xaa Ala Glu Ile Ala
385                 390                 395                 400

Pro Leu Pro Thr Gly Leu Glu His Trp Val Ser Leu Tyr Leu Ala Ile
                405                 410                 415

Thr Lys Asn Pro Gln Arg Ala Arg Phe Ser Tyr Gly Ser Gly Gly Leu
            420                 425                 430

Ser Leu Asp Trp Ser Gly Ala Gln Ser Ala Val Ser Ser Gly Met Ala
            435                 440                 445

Lys Lys Leu Phe Asp Arg Ile Asn Ser Ala Asn Ser Thr Ile Tyr Arg
450                 455                 460

Tyr Asp Leu Phe Gly Ser Pro Ser Arg Val Phe Ala Asp Asp Phe Thr
465                 470                 475                 480

Tyr His Pro Leu Gly Gly Cys Val Leu Gly Lys Ala Thr Asp Asn Tyr
                485                 490                 495

Gly Arg Val Lys Gly Tyr Ser Arg Leu Tyr Val Thr Asp Gly Ser Leu
            500                 505                 510

Ile Pro Gly Asn Ile Gly Val Asn Pro Phe Val Thr Ile Thr Ala Leu
            515                 520                 525

Ala Glu Arg Thr Met Ala Arg Val Leu Val Glu Asp Thr Ala Pro
            530                 535                 540

<210> SEQ ID NO 26
<211> LENGTH: 534
<212> TYPE: PRT
<213> ORGANISM: Saccharomonospora viridis
<220> FEATURE:
<221> NAME/KEY: MISC_FEATURE
<222> LOCATION: (150)..(150)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (219)..(219)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (387)..(387)
<223> OTHER INFORMATION: Xaa is Phe, Trp, Ser, Thr, Lys, Ala, Asn, His
      or Asp, provided that when Xaa150 is Met, then Xaa387 is not Phe

<400> SEQUENCE: 26

Met Arg Pro Leu Ser Arg Arg Leu Leu Gly Leu Leu Ala Val Asn
1               5                   10                  15

Thr Ala Ser Ala Leu Gly Leu Gly Thr Ile Ala Thr Pro Ser Ala Ala
            20                  25                  30

Ala Ala Ser Arg Arg Asp Phe Ser Pro Ala Val Val Val Gly Thr Gly
            35                  40                  45
```

Tyr Gly Ala Ala Val Thr Ala Leu Arg Leu Gly Gln Ala Gly Ile Pro
    50                  55                  60

Thr Val Met Leu Glu Met Gly Arg Leu Trp Asp Thr Pro Gly Asp Asp
65                  70                  75                  80

Gly Arg Val Phe Cys Asp Met Leu Asn Pro Asp Arg Arg Ala Met Trp
                85                  90                  95

Leu Ala Thr Arg Thr Gln Met Pro Leu Ser Ser Phe Leu Trp Leu Asp
            100                 105                 110

Ile Asp Arg Arg Ile Glu Arg Phe Thr Gly Val Leu Asp Cys Val His
        115                 120                 125

His Gly Asp Ile Ser Val Tyr Val Gly Arg Gly Val Gly Gly Gly Ser
130                 135                 140

Leu Val Asn Gly Ala Xaa Ala Val Thr Pro Lys Arg Ala Thr Phe Ala
145                 150                 155                 160

Glu Ala Phe Pro Asp Val Asp Ser Asp Gly Met Tyr Arg Thr Tyr Phe
                165                 170                 175

Pro Arg Ala Ala Ala Met Leu Gly Val Asn His Ile Asp Pro Ala Trp
            180                 185                 190

Phe Glu Thr Cys Glu Ser Tyr Arg Tyr Ala Arg Val Ser Arg Ala His
        195                 200                 205

Ala His Asn Ala Gly Leu Thr Thr Thr Phe Xaa Pro Ser Val Tyr Asp
210                 215                 220

Phe Ala Arg Met Arg Arg Glu Glu Ala Gly Glu Val Pro Arg Ser Ala
225                 230                 235                 240

Leu Ala Ala Glu Val Ile Tyr Gly Asn Asn His Gly Lys Arg Ser Leu
                245                 250                 255

Asp Lys Thr Tyr Leu Ala Asp Ala Leu Gly Thr Gly Cys Val Ser Ile
            260                 265                 270

Arg Thr Leu His His Val Arg Ala Ile Glu Gln Asp Ala Asp Gly Thr
        275                 280                 285

Tyr Val Leu Thr Val Asp Glu Leu Asp Leu Asp Gly Thr Arg Val Ala
290                 295                 300

Thr Arg Gln Leu Gly Ala Arg Tyr Leu Phe Leu Gly Ala Gly Ser Leu
305                 310                 315                 320

Gly Ser Thr Glu Leu Leu Leu Arg Ala Arg Asp Thr Gly Ala Leu Pro
                325                 330                 335

Gly Leu Ser Pro Leu Ile Gly Arg Asp Trp Gly Pro Asn Gly Asn Val
            340                 345                 350

Met Val Gly Arg Ala Asn Arg Pro Arg Asp Arg Thr Gly Thr Val Gln
        355                 360                 365

Ser Gly Met Pro Ala Leu Gly Ile Asp Ala Trp Asp Asp Pro Arg His
370                 375                 380

Pro Val Xaa Ala Glu Val Ala Pro Met Pro Ala Gly Val Glu Leu Trp
385                 390                 395                 400

Val Ser Leu Tyr Leu Ala Val Thr Arg Asn Pro Glu Arg Gly Leu Leu
                405                 410                 415

Thr Tyr Asp Ala Gly Ser Asp Arg Val Arg Leu His Trp Leu Ser Gly
            420                 425                 430

Gln Ala Gln Pro Ser Val Asp Gln Ala Lys Ala Leu Phe Asp Arg Leu
        435                 440                 445

Asn Ala Ala Asn Gly Thr Glu Tyr Arg Ser Asp Leu Phe Gly Asp Thr
450                 455                 460

-continued

```
Arg Val Phe Glu Thr Arg Leu Thr Tyr His Pro Leu Gly Gly Ala Val
465                 470                 475                 480

Leu Gly Lys Ala Thr Asp Ala Tyr Gly Arg Val Arg Gly Gln Arg Arg
            485                 490                 495

Leu Tyr Val Thr Asp Gly Ser Leu Val Pro Gly Asn Ile Gly Val Asn
        500                 505                 510

Pro Phe Leu Thr Ile Thr Ala Leu Ala Glu Arg Asn Ile Glu Arg Ile
    515                 520                 525

Leu Ala Glu Asp Leu Arg
    530

<210> SEQ ID NO 27
<211> LENGTH: 552
<212> TYPE: PRT
<213> ORGANISM: Rhodococcus equi
<220> FEATURE:
<221> NAME/KEY: MISC_FEATURE
<222> LOCATION: (167)..(167)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (236)..(236)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (404)..(404)
<223> OTHER INFORMATION: Xaa is Phe, Trp, Ser, Thr, Lys, Ala, Asn, His
      or Asp, provided that when Xaa167 is Met, then Xaa404 is not Phe

<400> SEQUENCE: 27

Met Thr Asp Ser Arg Ala Asn Arg Ala Asp Ala Thr Arg Gly Val Ala
1               5                   10                  15

Ser Val Ser Arg Arg Arg Phe Leu Ala Gly Ala Gly Leu Thr Ala Gly
            20                  25                  30

Ala Ile Ala Leu Ser Ser Met Ser Thr Ser Ala Ser Ala Ala Pro Ser
        35                  40                  45

Arg Thr Leu Ala Asp Gly Asp Arg Val Pro Ala Leu Val Ile Gly Ser
    50                  55                  60

Gly Tyr Gly Gly Ala Val Ala Ala Leu Arg Leu Thr Gln Ala Gly Ile
65                  70                  75                  80

Pro Thr Gln Ile Val Glu Met Gly Arg Ser Trp Asp Thr Pro Gly Ser
                85                  90                  95

Asp Gly Lys Ile Phe Cys Gly Met Leu Asn Pro Asp Lys Arg Ser Met
            100                 105                 110

Trp Leu Ala Asp Lys Thr Asp Gln Pro Val Ser Asn Phe Met Gly Phe
        115                 120                 125

Gly Ile Asn Lys Ser Ile Asp Arg Tyr Val Gly Val Leu Asp Ser Glu
    130                 135                 140

Arg Phe Ser Gly Ile Lys Val Tyr Gln Gly Arg Gly Val Gly Gly Gly
145                 150                 155                 160

Ser Leu Val Asn Gly Gly Xaa Ala Val Thr Pro Lys Arg Asn Tyr Phe
                165                 170                 175

Glu Glu Ile Leu Pro Ser Val Asp Ser Asn Glu Met Tyr Asn Lys Tyr
            180                 185                 190

Phe Pro Arg Ala Asn Thr Gly Leu Gly Val Asn Asn Ile Asp Gln Ala
        195                 200                 205

Trp Phe Glu Ser Thr Glu Trp Tyr Lys Phe Ala Arg Thr Gly Arg Lys
    210                 215                 220
```

-continued

```
Thr Ala Gln Arg Ser Gly Phe Thr Thr Ala Phe Xaa Pro Asn Val Tyr
225                 230                 235                 240

Asp Phe Glu Tyr Met Lys Lys Glu Ala Ala Gly Gln Val Thr Lys Ser
            245                 250                 255

Gly Leu Gly Gly Glu Val Ile Tyr Gly Asn Asn Ala Gly Lys Lys Ser
        260                 265                 270

Leu Asp Lys Thr Tyr Leu Ala Gln Ala Ala Thr Gly Lys Leu Thr
    275                 280                 285

Ile Thr Thr Leu His Arg Val Thr Lys Val Ala Pro Ala Thr Gly Ser
290                 295                 300

Gly Tyr Ser Val Thr Met Glu Gln Ile Asp Gln Gly Asn Val Val
305                 310                 315                 320

Ala Thr Lys Val Val Thr Ala Asp Arg Val Phe Phe Ala Ala Gly Ser
                325                 330                 335

Val Gly Thr Ser Lys Leu Leu Val Ser Met Lys Ala Gln Gly His Leu
            340                 345                 350

Pro Asn Leu Ser Ser Gln Val Gly Glu Gly Trp Gly Asn Asn Gly Asn
        355                 360                 365

Ile Met Val Gly Arg Ala Asn His Met Trp Asp Ala Thr Gly Ser Lys
370                 375                 380

Gln Ala Thr Ile Pro Thr Met Gly Ile Asp Asn Trp Ala Asp Pro Thr
385                 390                 395                 400

Ala Pro Ile Xaa Ala Glu Ile Ala Pro Leu Pro Ala Gly Leu Glu Thr
                405                 410                 415

Tyr Val Ser Leu Tyr Leu Ala Ile Thr Lys Asn Pro Glu Arg Ala Arg
            420                 425                 430

Phe Gln Phe Asn Ser Gly Thr Gly Lys Val Asp Leu Thr Trp Ala Gln
        435                 440                 445

Ser Gln Asn Gln Lys Gly Ile Asp Met Ala Lys Lys Val Phe Asp Lys
450                 455                 460

Ile Asn Gln Lys Glu Gly Thr Ile Tyr Arg Thr Asp Leu Phe Gly Val
465                 470                 475                 480

Tyr Phe Lys Thr Trp Gly Asp Asp Phe Thr Tyr His Pro Leu Gly Gly
                485                 490                 495

Val Leu Leu Asn Lys Ala Thr Asp Asn Phe Gly Arg Leu Pro Glu Tyr
            500                 505                 510

Pro Gly Leu Tyr Val Val Asp Gly Ser Leu Val Pro Gly Asn Val Gly
        515                 520                 525

Val Asn Pro Phe Val Thr Ile Thr Ala Leu Ala Glu Arg Asn Met Asp
530                 535                 540

Lys Ile Ile Ser Ser Asp Ile Gln
545                 550

<210> SEQ ID NO 28
<211> LENGTH: 507
<212> TYPE: PRT
<213> ORGANISM: Brevibacterium sterolicum
<220> FEATURE:
<221> NAME/KEY: MISC_FEATURE
<222> LOCATION: (122)..(122)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (191)..(191)
<223> OTHER INFORMATION: Xaa is Val, Met, Ile, Ala, Thr, Lys, Cys, Ser,
      Gly, Glu, Tyr, Pro, Asn, Gln, Trp or His
```

```
<220> FEATURE:
<221> NAME/KEY: MISC_FEATURE
<222> LOCATION: (359)..(359)
<223> OTHER INFORMATION: Xaa is Phe, Trp, Ser, Thr, Lys, Ala, Asn, His
      or Asp, provided that when Xaa122 is Met, then Xaa359 is not Phe

<400> SEQUENCE: 28

Ala Pro Ser Arg Thr Leu Ala Asp Gly Asp Arg Val Pro Ala Leu Val
1               5                   10                  15

Ile Gly Ser Gly Tyr Gly Ala Val Ala Leu Arg Leu Thr Gln
            20                  25                  30

Ala Gly Ile Pro Thr Gln Ile Val Glu Met Gly Arg Ser Trp Asp Thr
            35                  40                  45

Pro Gly Ser Asp Gly Lys Ile Phe Cys Gly Met Leu Asn Pro Asp Lys
        50                  55                  60

Arg Ser Met Trp Leu Ala Asp Lys Thr Asp Gln Pro Val Ser Asn Phe
65                  70                  75                  80

Met Gly Phe Gly Ile Asn Lys Ser Ile Asp Arg Tyr Val Gly Val Leu
                85                  90                  95

Asp Ser Glu Arg Phe Ser Gly Ile Lys Val Tyr Gln Gly Arg Gly Val
            100                 105                 110

Gly Gly Gly Ser Leu Val Asn Gly Gly Xaa Ala Val Thr Pro Lys Arg
            115                 120                 125

Asn Tyr Phe Glu Glu Ile Leu Pro Ser Val Asp Ser Asn Glu Met Tyr
130                 135                 140

Asn Lys Tyr Phe Pro Arg Ala Asn Thr Gly Leu Gly Val Asn Asn Ile
145                 150                 155                 160

Asp Gln Ala Trp Phe Glu Ser Thr Glu Trp Tyr Lys Phe Ala Arg Thr
                165                 170                 175

Gly Arg Lys Thr Ala Gln Arg Ser Gly Phe Thr Thr Ala Phe Xaa Pro
            180                 185                 190

Asn Val Tyr Asp Phe Glu Tyr Met Lys Lys Glu Ala Ala Gly Gln Val
            195                 200                 205

Thr Lys Ser Gly Leu Gly Gly Glu Val Ile Tyr Gly Asn Asn Ala Gly
210                 215                 220

Lys Lys Ser Leu Asp Lys Thr Tyr Leu Ala Gln Ala Ala Thr Gly
225                 230                 235                 240

Lys Leu Thr Ile Thr Thr Leu His Arg Val Thr Lys Val Ala Pro Ala
                245                 250                 255

Thr Gly Ser Gly Tyr Ser Val Thr Met Glu Gln Ile Asp Glu Gln Gly
            260                 265                 270

Asn Val Val Ala Thr Lys Val Thr Ala Asp Arg Val Phe Phe Ala
            275                 280                 285

Ala Gly Ser Val Gly Thr Ser Lys Leu Leu Val Ser Met Lys Ala Gln
290                 295                 300

Gly His Leu Pro Asn Leu Ser Ser Gln Val Gly Glu Gly Trp Gly Asn
305                 310                 315                 320

Asn Gly Asn Ile Met Val Gly Arg Ala Asn His Met Trp Asp Ala Thr
                325                 330                 335

Gly Ser Lys Gln Ala Thr Ile Pro Thr Met Gly Ile Asp Asn Trp Ala
            340                 345                 350

Asp Pro Thr Ala Pro Ile Xaa Ala Glu Ile Ala Pro Leu Pro Ala Gly
            355                 360                 365

Leu Glu Thr Tyr Val Ser Leu Tyr Leu Ala Ile Thr Lys Asn Pro Glu
370                 375                 380
```

```
Arg Ala Arg Phe Gln Phe Asn Ser Gly Thr Gly Lys Val Asp Leu Thr
385                 390                 395                 400

Trp Ala Gln Ser Gln Asn Gln Lys Gly Ile Asp Met Ala Lys Lys Val
                405                 410                 415

Phe Asp Lys Ile Asn Gln Lys Glu Gly Thr Ile Tyr Arg Thr Asp Leu
            420                 425                 430

Phe Gly Val Tyr Tyr Lys Thr Trp Gly Asp Asp Phe Thr Tyr His Pro
        435                 440                 445

Leu Gly Gly Val Leu Leu Asn Lys Ala Thr Asp Asn Phe Gly Arg Leu
    450                 455                 460

Pro Glu Tyr Pro Gly Leu Tyr Val Val Asp Gly Ser Leu Val Pro Gly
465                 470                 475                 480

Asn Val Gly Val Asn Pro Phe Val Thr Ile Thr Ala Leu Ala Glu Arg
                485                 490                 495

Asn Met Asp Lys Ile Ile Ser Ser Asp Ile Gln
                500                 505
```

<210> SEQ ID NO 29
<211> LENGTH: 552
<212> TYPE: PRT
<213> ORGANISM: Brevibacterium sterolicum
<220> FEATURE:
<221> NAME/KEY: MISC_FEATURE
<222> LOCATION: (167)..(167)
<223> OTHER INFORMATION: Xaa is Met, Phe, Leu, Val, Cys, Ile, Ala, Gln, Tyr, Lys or Ser
<220> FEATURE:
<221> NAME/KEY: MISC_FEATURE
<222> LOCATION: (236)..(236)
<223> OTHER INFORMATION: Xaa is Val, Met, Ile, Ala, Thr, Lys, Cys, Ser, Gly, Glu, Tyr, Pro, Asn, Gln, Trp or His
<220> FEATURE:
<221> NAME/KEY: MISC_FEATURE
<222> LOCATION: (404)..(404)
<223> OTHER INFORMATION: Xaa is Phe, Trp, Ser, Thr, Lys, Ala, Asn, His or Asp, provided that when Xaa167 is Met, then Xaa404 is not Phe

<400> SEQUENCE: 29

```
Met Thr Asp Ser Arg Ala Asn Arg Ala Asp Ala Thr Arg Gly Val Ala
1               5                   10                  15

Ser Val Ser Arg Arg Phe Leu Ala Gly Ala Gly Leu Thr Ala Gly
            20                  25                  30

Ala Ile Ala Leu Ser Ser Met Ser Thr Ser Ala Ser Ala Ala Pro Ser
            35                  40                  45

Arg Thr Leu Ala Asp Gly Asp Arg Val Pro Ala Leu Val Ile Gly Ser
50                  55                  60

Gly Tyr Gly Gly Ala Val Ala Ala Leu Arg Leu Thr Gln Ala Gly Ile
65                  70                  75                  80

Pro Thr Gln Ile Val Glu Met Gly Arg Ser Trp Asp Thr Pro Gly Ser
                85                  90                  95

Asp Gly Lys Ile Phe Cys Gly Met Leu Asn Pro Asp Lys Arg Ser Met
            100                 105                 110

Trp Leu Ala Asp Lys Thr Asp Gln Pro Val Ser Asn Phe Met Gly Phe
        115                 120                 125

Gly Ile Asn Lys Ser Ile Asp Arg Tyr Val Gly Leu Asp Ser Glu
    130                 135                 140

Arg Phe Ser Gly Ile Lys Val Tyr Gln Gly Arg Gly Val Gly Gly Gly
145                 150                 155                 160

Ser Leu Val Asn Gly Gly Xaa Ala Val Thr Pro Lys Arg Asn Tyr Phe
```

```
                    165                 170                 175
Glu Glu Ile Leu Pro Ser Val Asp Ser Asn Glu Met Tyr Asn Lys Tyr
                180                 185                 190

Phe Pro Arg Ala Asn Thr Gly Leu Gly Val Asn Asn Ile Asp Gln Ala
            195                 200                 205

Trp Phe Glu Ser Thr Glu Trp Tyr Lys Phe Ala Arg Thr Gly Arg Lys
        210                 215                 220

Thr Ala Gln Arg Ser Gly Phe Thr Thr Ala Phe Xaa Pro Asn Val Tyr
225                 230                 235                 240

Asp Phe Glu Tyr Met Lys Lys Glu Ala Ala Gly Gln Val Thr Lys Ser
                245                 250                 255

Gly Leu Gly Gly Glu Val Ile Tyr Gly Asn Asn Ala Gly Lys Lys Ser
                260                 265                 270

Leu Asp Lys Thr Tyr Leu Ala Gln Ala Ala Thr Gly Lys Leu Thr
                275                 280                 285

Ile Thr Thr Leu His Arg Val Thr Lys Val Ala Pro Ala Thr Gly Ser
        290                 295                 300

Gly Tyr Ser Val Thr Met Glu Gln Ile Asp Glu Gln Gly Asn Val Val
305                 310                 315                 320

Ala Thr Lys Val Val Thr Ala Asp Arg Val Phe Phe Ala Ala Gly Ser
                325                 330                 335

Val Gly Thr Ser Lys Leu Leu Val Ser Met Lys Ala Gln Gly His Leu
                340                 345                 350

Pro Asn Leu Ser Ser Gln Val Gly Glu Gly Trp Gly Asn Asn Gly Asn
                355                 360                 365

Ile Met Val Gly Arg Ala Asn His Met Trp Asp Ala Thr Gly Ser Lys
        370                 375                 380

Gln Ala Thr Ile Pro Thr Met Gly Ile Asp Asn Trp Ala Asp Pro Thr
385                 390                 395                 400

Ala Pro Ile Xaa Ala Glu Ile Ala Pro Leu Pro Ala Gly Leu Glu Thr
                405                 410                 415

Tyr Val Ser Leu Tyr Leu Ala Ile Thr Lys Asn Pro Glu Arg Ala Arg
                420                 425                 430

Phe Gln Phe Asn Ser Gly Thr Gly Lys Val Asp Leu Thr Trp Ala Gln
            435                 440                 445

Ser Gln Asn Gln Lys Gly Ile Asp Met Ala Lys Lys Val Phe Asp Lys
        450                 455                 460

Ile Asn Gln Lys Glu Gly Thr Ile Tyr Arg Thr Asp Leu Phe Gly Val
465                 470                 475                 480

Tyr Phe Lys Thr Trp Gly Asp Asp Phe Thr Tyr His Pro Leu Gly Gly
                485                 490                 495

Val Leu Leu Asn Lys Ala Thr Asp Asn Phe Gly Arg Leu Pro Glu Tyr
                500                 505                 510

Pro Gly Leu Tyr Val Val Asp Gly Ser Leu Val Pro Gly Asn Val Gly
            515                 520                 525

Val Asn Pro Phe Val Thr Ile Thr Arg Leu Ala Glu Arg Asn Met Asp
530                 535                 540

Lys Ile Ile Ser Ser Asp Ile Gln
545                 550

<210> SEQ ID NO 30
<211> LENGTH: 551
<212> TYPE: PRT
<213> ORGANISM: Rhodococcus equi
```

```
<220> FEATURE:
<221> NAME/KEY: MISC_FEATURE
<222> LOCATION: (167)..(167)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (236)..(236)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (404)..(404)
<223> OTHER INFORMATION: Xaa is Phe, Trp, Ser, Thr, Lys, Ala, Asn, His
      or Asp, provided that when Xaa167 is Met, then Xaa404 is not Phe

<400> SEQUENCE: 30

Met Thr Asp Ser Arg Ala Asn Arg Ala Asp Ala Thr Arg Gly Val Ala
1               5                   10                  15

Ser Val Ser Arg Arg Phe Leu Ala Gly Ala Gly Leu Thr Ala Gly
            20                  25                  30

Ala Ile Ala Leu Ser Ser Met Ser Thr Ser Ala Ser Ala Ala Pro Ser
        35                  40                  45

Arg Thr Leu Ala Asp Gly Asp Arg Val Pro Ala Leu Val Ile Gly Ser
50                  55                  60

Gly Tyr Gly Gly Ala Val Ala Ala Leu Arg Leu Thr Gln Ala Gly Ile
65                  70                  75                  80

Pro Thr Gln Ile Val Glu Met Gly Arg Ser Trp Asp Thr Pro Gly Ser
                85                  90                  95

Asp Gly Lys Ile Phe Cys Gly Met Leu Asn Pro Asp Lys Arg Ser Met
            100                 105                 110

Trp Leu Ala Asp Lys Thr Asp Gln Pro Val Ser Asn Phe Met Gly Phe
        115                 120                 125

Gly Ile Asn Lys Ser Ile Asp Arg Tyr Val Gly Val Leu Asp Ser Glu
130                 135                 140

Arg Phe Ser Gly Ile Lys Val Tyr Gln Gly Arg Gly Val Gly Gly Gly
145                 150                 155                 160

Ser Leu Val Asn Gly Gly Xaa Ala Val Thr Pro Lys Arg Asn Tyr Phe
                165                 170                 175

Glu Glu Ile Leu Pro Ser Val Asp Ser Asn Glu Met Tyr Asn Lys Tyr
            180                 185                 190

Phe Pro Arg Ala Asn Thr Gly Leu Gly Val Asn Asn Ile Asp Gln Ala
        195                 200                 205

Trp Phe Glu Ser Thr Glu Trp Tyr Lys Phe Ala Arg Thr Gly Arg Lys
210                 215                 220

Thr Ala Gln Arg Ser Gly Phe Thr Thr Ala Phe Xaa Pro Asn Val Tyr
225                 230                 235                 240

Asp Phe Glu Tyr Met Lys Lys Glu Ala Ala Gly Gln Val Thr Lys Ser
            245                 250                 255

Gly Leu Gly Gly Glu Val Ile Tyr Gly Asn Asn Ala Gly Lys Lys Ser
        260                 265                 270

Leu Asp Lys Thr Tyr Leu Ala Gln Ala Ala Thr Gly Lys Leu Thr
                275                 280                 285

Ile Thr Thr Leu His Arg Val Thr Lys Val Ala Pro Ala Thr Gly Ser
            290                 295                 300

Gly Tyr Ser Val Thr Met Glu Gln Ile Asp Glu Gln Gly Asn Val Val
305                 310                 315                 320

Ala Thr Lys Val Val Thr Ala Asp Arg Val Phe Phe Ala Ala Gly Ser
```

325                 330                 335
Val Gly Thr Ser Lys Leu Leu Val Ser Met Lys Ala Gln Gly His Leu
            340                 345                 350

Pro Asn Leu Ser Ser Gln Val Gly Glu Gly Trp Gly Asn Asn Gly Asn
            355                 360                 365

Ile Met Val Gly Arg Ala Asn His Met Trp Asp Ala Thr Gly Ser Lys
    370                 375                 380

Gln Ala Thr Ile Pro Thr Met Gly Ile Asp Asn Trp Ala Asp Pro Thr
385                 390                 395                 400

Ala Pro Ile Xaa Ala Glu Ile Ala Pro Leu Pro Ala Gly Leu Glu Thr
                405                 410                 415

Tyr Val Ser Leu Tyr Leu Ala Ile Thr Lys Asn Pro Glu Arg Ala Arg
            420                 425                 430

Phe Gln Phe Asn Ser Gly Thr Gly Lys Val Asp Leu Thr Trp Ala Gln
            435                 440                 445

Ser Gln Asn Gln Lys Gly Ile Asp Met Ala Lys Lys Val Phe Asp Lys
450                 455                 460

Ile Asn Gln Lys Glu Gly Thr Ile Tyr Arg Thr Asp Leu Phe Gly Val
465                 470                 475                 480

Tyr Lys Thr Trp Gly Asp Asp Phe Thr Tyr His Pro Leu Gly Gly Val
                485                 490                 495

Leu Leu Asn Lys Ala Thr Asp Asn Phe Gly Arg Leu Pro Glu Tyr Pro
            500                 505                 510

Gly Leu Tyr Val Val Asp Gly Ser Leu Val Pro Gly Asn Val Gly Val
            515                 520                 525

Asn Pro Phe Val Thr Ile Thr Ala Leu Ala Glu Arg Asn Met Asp Lys
            530                 535                 540

Ile Ile Ser Ser Asp Ile Gln
545                 550

<210> SEQ ID NO 31
<211> LENGTH: 551
<212> TYPE: PRT
<213> ORGANISM: Brevibacterium sp.
<220> FEATURE:
<221> NAME/KEY: MISC_FEATURE
<222> LOCATION: (167)..(167)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (236)..(236)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (404)..(404)
<223> OTHER INFORMATION: Xaa is Phe, Trp, Ser, Thr, Lys, Ala, Asn, His
      or Asp, provided that when Xaa167 is Met, then Xaa404 is not Phe

<400> SEQUENCE: 31

Met Thr Asp Ser Arg Ala Asn Arg Ala Asp Ala Thr Arg Gly Val Ala
1               5                   10                  15

Ser Val Ser Arg Arg Arg Phe Leu Ala Gly Ala Gly Leu Thr Ala Gly
            20                  25                  30

Ala Ile Ala Leu Ser Ser Met Ser Thr Ser Ala Ser Ala Ala Pro Ser
        35                  40                  45

Arg Thr Leu Ala Asp Gly Asp Arg Val Pro Ala Leu Val Ile Gly Ser
    50                  55                  60

```
Gly Tyr Gly Gly Ala Val Ala Leu Arg Leu Thr Gln Ala Gly Ile
 65                  70                  75                  80

Pro Thr Gln Ile Val Glu Met Gly Arg Ser Trp Asp Thr Pro Gly Ser
                 85                  90                  95

Asp Gly Lys Ile Phe Cys Gly Met Leu Asn Pro Asp Lys Arg Ser Met
            100                 105                 110

Arg Leu Ala Asp Lys Thr Asp Gln Pro Val Ser Asn Phe Met Gly Phe
        115                 120                 125

Gly Ile Asn Lys Ser Ile Asp Arg Tyr Val Gly Val Leu Asp Ser Glu
    130                 135                 140

Arg Phe Ser Gly Ile Lys Val Tyr Gln Gly Arg Gly Val Gly Gly Gly
145                 150                 155                 160

Ser Leu Val Asn Gly Gly Xaa Ala Val Thr Pro Lys Arg Asn Tyr Phe
                165                 170                 175

Glu Glu Ile Leu Pro Ser Val Asp Ser Asn Glu Met Tyr Asn Lys Tyr
            180                 185                 190

Phe Pro Arg Ala Asn Thr Gly Leu Gly Val Asn Asn Ile Asp Gln Ala
        195                 200                 205

Trp Phe Glu Ser Thr Glu Trp Tyr Lys Phe Ala Arg Thr Gly Arg Lys
210                 215                 220

Thr Ala Gln Arg Ser Gly Phe Thr Thr Ala Phe Xaa Pro Asn Val Tyr
225                 230                 235                 240

Asp Phe Glu Tyr Met Lys Lys Glu Ala Ala Gly Gln Val Thr Lys Ser
                245                 250                 255

Gly Leu Gly Gly Glu Val Ile Tyr Gly Asn Asn Ala Gly Lys Lys Ser
            260                 265                 270

Leu Asp Lys Thr Tyr Leu Ala Gln Ala Ala Thr Gly Lys Leu Thr
        275                 280                 285

Ile Thr Thr Leu His Arg Val Thr Lys Val Ala Pro Ala Thr Gly Ser
    290                 295                 300

Gly Tyr Ser Val Thr Met Glu Gln Ile Asp Gln Gly Asn Val Val
305                 310                 315                 320

Ala Thr Lys Val Val Thr Ala Asp Arg Val Phe Phe Ala Ala Gly Ser
                325                 330                 335

Val Gly Thr Ser Lys Leu Leu Val Ser Met Lys Ala Gln Gly His Leu
            340                 345                 350

Pro Asn Leu Ser Ser Gln Val Gly Glu Gly Trp Gly Asn Asn Gly Asn
        355                 360                 365

Ile Met Val Gly Arg Ala Asn His Met Trp Asp Ala Thr Gly Ser Lys
    370                 375                 380

Gln Ala Thr Ile Pro Thr Met Gly Ile Asp Asn Trp Ala Asp Pro Ala
385                 390                 395                 400

Ala Pro Ile Xaa Ala Glu Ile Ala Pro Leu Pro Ala Gly Leu Glu Thr
                405                 410                 415

Tyr Val Ser Leu Tyr Leu Ala Ile Thr Lys Asn Pro Glu Arg Ala Arg
            420                 425                 430

Phe Gln Phe Asn Ser Gly Thr Gly Lys Val Asp Leu Thr Trp Ala Gln
        435                 440                 445

Ser Gln Asn Gln Lys Gly Ile Asp Met Ala Lys Lys Val Phe Asp Lys
    450                 455                 460

Ile Asn Gln Lys Glu Gly Thr Ile Tyr Arg Thr Asp Leu Phe Gly Val
465                 470                 475                 480

Tyr Lys Thr Trp Gly Asp Asp Phe Thr Tyr His Pro Leu Gly Gly Val
```

```
                    485                 490                 495

Leu Leu Asn Lys Ala Thr Asp Asn Phe Gly Arg Leu Pro Glu Tyr Pro
            500                 505                 510

Gly Leu Tyr Val Val Asp Gly Ser Leu Val Pro Gly Asn Val Gly Val
            515                 520                 525

Asn Pro Phe Val Thr Ile Thr Ala Leu Ala Glu Arg Asn Met Asp Lys
            530                 535                 540

Ile Ile Ser Ser Asp Ile Gln
545                 550

<210> SEQ ID NO 32
<211> LENGTH: 551
<212> TYPE: PRT
<213> ORGANISM: Rhodococcus sp.
<220> FEATURE:
<221> NAME/KEY: MISC_FEATURE
<222> LOCATION: (167)..(167)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (236)..(236)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (405)..(405)
<223> OTHER INFORMATION: Xaa is Phe, Trp, Ser, Thr, Lys, Ala, Asn, His
      or Asp, provided that when Xaa167 is Met, then Xaa405 is not Phe

<400> SEQUENCE: 32

Met Thr Asp Ser Arg Ala Asn Arg Ala Asp Ala Thr Arg Gly Val Ala
1               5                   10                  15

Ser Val Ser Arg Arg Arg Phe Leu Ala Gly Ala Gly Leu Thr Ala Gly
            20                  25                  30

Ala Ile Ala Leu Ser Ser Met Ser Thr Ser Ala Ser Ala Ala Pro Ser
        35                  40                  45

Arg Thr Leu Ala Asp Gly Asp Arg Val Pro Ala Leu Val Ile Gly Ser
    50                  55                  60

Gly Tyr Gly Gly Ala Val Ala Ala Leu Arg Leu Thr Gln Ala Gly Ile
65                  70                  75                  80

Pro Thr Gln Ile Val Glu Met Gly Arg Ser Trp Asp Thr Pro Gly Ser
                85                  90                  95

Asp Gly Lys Ile Phe Cys Gly Met Leu Asn Pro Asp Lys Arg Ser Met
            100                 105                 110

Trp Leu Ala Asp Lys Thr Asp Gln Pro Val Ser Asn Phe Met Gly Phe
        115                 120                 125

Gly Ile Asn Lys Ser Ile Asp Arg Tyr Val Gly Val Leu Asp Ser Glu
    130                 135                 140

Arg Phe Ser Gly Ile Lys Val Tyr Gln Gly Arg Gly Val Gly Gly Gly
145                 150                 155                 160

Ser Leu Val Asn Gly Gly Xaa Ala Val Thr Pro Lys Arg Asn Tyr Phe
                165                 170                 175

Glu Glu Ile Leu Pro Ser Val Asp Ser Asn Glu Met Tyr Asn Lys Tyr
            180                 185                 190

Phe Pro Arg Ala Asn Thr Gly Leu Gly Val Asn His Ile Asp Gln Ala
        195                 200                 205

Trp Phe Glu Ser Thr Glu Trp Tyr Lys Phe Ala Arg Thr Gly Arg Lys
    210                 215                 220
```

```
Thr Ala Gln Arg Ser Gly Phe Thr Thr Ala Phe Xaa Pro Asn Val Tyr
225                 230                 235                 240

Asp Phe Glu Tyr Met Lys Lys Glu Ala Ala Gly Gln Val Thr Lys Ser
            245                 250                 255

Gly Leu Gly Gly Glu Val Ile Tyr Gly Asn Asn Ala Gly Lys Lys Ser
        260                 265                 270

Leu Asp Lys Thr Tyr Leu Ala Gln Ala Ala Thr Gly Lys Leu Thr
            275                 280                 285

Ile Thr Thr Leu His Arg Val Thr Lys Val Ala Pro Ala Thr Gly Ser
        290                 295                 300

Gly Tyr Ser Val Thr Met Glu Gln Ile Asp Glu Gln Gly Asn Val Val
305                 310                 315                 320

Ala Ala Thr Lys Val Val Thr Ala Asp Arg Val Phe Phe Ala Ala Gly
            325                 330                 335

Ser Val Gly Thr Ser Lys Leu Leu Val Ser Met Lys Ala Gln Gly His
            340                 345                 350

Leu Pro Asn Leu Ser Ser Gln Val Gly Glu Gly Trp Gly Asn Asn Gly
            355                 360                 365

Asn Ile Met Val Gly Arg Ala Asn His Met Trp Asp Ala Thr Gly Ser
370                 375                 380

Lys Gln Ala Thr Ile Pro Thr Met Gly Ile Asp Asn Trp Ala Asp Pro
385                 390                 395                 400

Thr Ala Pro Ile Xaa Ala Glu Ile Ala Pro Leu Pro Ala Gly Leu Glu
                405                 410                 415

Thr Tyr Val Ser Leu Tyr Leu Ala Ile Thr Lys Asn Pro Glu Arg Ala
            420                 425                 430

Arg Phe Gln Phe Asn Ser Gly Thr Gly Lys Val Asp Leu Thr Trp Ala
        435                 440                 445

Gln Ser Gln Asn Gln Lys Gly Ile Asp Met Ala Lys Lys Val Phe Asp
    450                 455                 460

Lys Ile Asn Gln Lys Glu Gly Thr Ile Tyr Arg Thr Asp Leu Phe Gly
465                 470                 475                 480

Val Tyr Lys Thr Trp Gly Asp Asp Phe Thr Tyr His Pro Leu Gly Gly
            485                 490                 495

Val Leu Leu Asn Lys Ala Thr Asp Asn Phe Gly Arg Leu Pro Glu Tyr
            500                 505                 510

Pro Gly Leu Tyr Val Val Asp Gly Ser Leu Val Pro Gly Asn Val Gly
        515                 520                 525

Val Asn Pro Phe Val Thr Ile Thr Ala Leu Ala Arg Asn Met Asp Lys
530                 535                 540

Ile Ile Ser Ser Asp Ile Gln
545                 550

<210> SEQ ID NO 33
<211> LENGTH: 533
<212> TYPE: PRT
<213> ORGANISM: Rhodococcus sp.
<220> FEATURE:
<221> NAME/KEY: MISC_FEATURE
<222> LOCATION: (1)..(1)
<223> OTHER INFORMATION: Xaa is unknown
<220> FEATURE:
<221> NAME/KEY: MISC_FEATURE
<222> LOCATION: (158)..(158)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
```

<222> LOCATION: (227)..(227)
<223> OTHER INFORMATION: Xaa is Val, Met, Ile, Ala, Thr, Lys, Cys, Ser, Gly, Glu, Tyr, Pro, Asn, Gln, Trp or His
<220> FEATURE:
<221> NAME/KEY: MISC_FEATURE
<222> LOCATION: (395)..(395)
<223> OTHER INFORMATION: Xaa is Phe, Trp, Ser, Thr, Lys, Ala, Asn, His or Asp, provided that when Xaa158 is Met, then Xaa395 is not Phe

<400> SEQUENCE: 33

```
Xaa Ala Thr Arg Gly Val Ala Ser Val Ser Arg Arg Arg Phe Leu Ala
1               5                   10                  15

Gly Ala Gly Leu Thr Ala Gly Ala Ile Ala Leu Ser Ser Met Ser Thr
            20                  25                  30

Ser Ala Ser Ala Ala Pro Ser Arg Thr Leu Ala Asp Gly Asp Arg Val
        35                  40                  45

Pro Ala Leu Val Ile Gly Ser Gly Tyr Gly Gly Ala Val Ala Ala Leu
    50                  55                  60

Arg Leu Thr Gln Ala Gly Ile Pro Thr Gln Ile Val Glu Met Gly Arg
65                  70                  75                  80

Ser Trp Asp Thr Pro Gly Ser Asp Gly Lys Ile Phe Cys Gly Met Leu
                85                  90                  95

Asn Pro Asp Lys Arg Ser Met Trp Leu Ala Asp Lys Thr Asp Gln Pro
            100                 105                 110

Val Ser Asn Phe Met Gly Phe Gly Ile Asn Lys Ser Ile Asp Arg Tyr
        115                 120                 125

Val Gly Val Leu Asp Ser Glu Arg Phe Ser Gly Ile Lys Val Tyr Gln
    130                 135                 140

Gly Arg Gly Val Gly Gly Gly Ser Leu Val Asn Gly Gly Xaa Ala Val
145                 150                 155                 160

Thr Pro Lys Arg Asn Tyr Phe Glu Glu Ile Leu Pro Ser Val Asp Ser
                165                 170                 175

Asn Glu Met Tyr Asn Lys Tyr Phe Pro Arg Ala Asn Thr Gly Leu Gly
            180                 185                 190

Val Asn Asn Ile Asp Gln Ala Trp Phe Glu Ser Thr Glu Trp Tyr Lys
        195                 200                 205

Phe Ala Arg Thr Gly Arg Lys Thr Ala Gln Arg Ser Gly Phe Thr Thr
    210                 215                 220

Ala Phe Xaa Pro Asn Val Tyr Asp Phe Glu Tyr Met Lys Lys Glu Ala
225                 230                 235                 240

Ala Gly Gln Val Thr Lys Ser Gly Leu Gly Gly Glu Val Ile Tyr Gly
                245                 250                 255

Asn Asn Ala Gly Lys Lys Ser Leu Asp Lys Thr Tyr Leu Ala Gln Ala
            260                 265                 270

Ala Ala Thr Gly Lys Leu Thr Ile Thr Thr Leu His Arg Val Thr Lys
        275                 280                 285

Val Ala Pro Ala Thr Gly Ser Gly Tyr Ser Val Thr Met Glu Gln Ile
    290                 295                 300

Asp Glu Gln Gly Asn Val Val Ala Thr Lys Val Val Thr Ala Asp Arg
305                 310                 315                 320

Val Phe Phe Ala Ala Gly Ser Val Gly Thr Ser Lys Leu Leu Val Ser
                325                 330                 335

Met Lys Ala Gln Gly His Leu Pro Asn Leu Ser Ser Gln Val Gly Glu
            340                 345                 350

Gly Trp Gly Asn Asn Gly Asn Ile Met Val Gly Arg Ala Asn His Met
        355                 360                 365
```

-continued

```
Trp Asp Ala Thr Gly Ser Lys Gln Ala Thr Ile Pro Thr Met Gly Ile
        370                 375                 380

Asp Asn Trp Ala Asp Pro Thr Ala Pro Ile Xaa Ala Glu Ile Ala Pro
385                 390                 395                 400

Leu Pro Ala Gly Leu Glu Thr Tyr Val Ser Leu Tyr Leu Ala Ile Thr
                405                 410                 415

Lys Asn Pro Glu Arg Ala Arg Phe Gln Phe Asn Ser Gly Thr Gly Lys
            420                 425                 430

Val Asp Leu Thr Trp Ala Gln Ser Gln Asn Gln Lys Gly Ile Asp Met
        435                 440                 445

Ala Lys Lys Val Phe Asp Lys Ile Asn Gln Lys Glu Gly Thr Ile Tyr
    450                 455                 460

Arg Thr Asp Leu Phe Gly Val Tyr Lys Thr Trp Gly Asp Asp Phe Thr
465                 470                 475                 480

Tyr His Pro Leu Gly Gly Val Leu Leu Asn Lys Ala Thr Asp Asn Phe
                485                 490                 495

Gly Arg Leu Pro Glu Tyr Pro Gly Leu Tyr Val Val Asp Gly Ser Leu
            500                 505                 510

Val Pro Gly Asn Val Gly Val Asn Pro Phe Val Thr Ile Thr Ala Leu
        515                 520                 525

Ala Glu Arg Asn Met
    530
```

<210> SEQ ID NO 34
<211> LENGTH: 552
<212> TYPE: PRT
<213> ORGANISM: Rhodococcus erythropolis
<220> FEATURE:
<221> NAME/KEY: MISC_FEATURE
<222> LOCATION: (167)..(167)
<223> OTHER INFORMATION: Xaa is Met, Phe, Leu, Val, Cys, Ile, Ala, Gln,
    Tyr, Lys or Ser
<220> FEATURE:
<221> NAME/KEY: MISC_FEATURE
<222> LOCATION: (236)..(236)
<223> OTHER INFORMATION: Xaa is Val, Met, Ile, Ala, Thr, Lys, Cys, Ser,
    Gly, Glu, Tyr, Pro, Asn, Gln, Trp or His
<220> FEATURE:
<221> NAME/KEY: MISC_FEATURE
<222> LOCATION: (405)..(405)
<223> OTHER INFORMATION: Xaa is Phe, Trp, Ser, Thr, Lys, Ala, Asn, His
    or Asp, provided that when Xaa167 is Met, then Xaa405 is not Phe

<400> SEQUENCE: 34

```
Met Ser Ile Arg Ala Gly Ser Asn Glu Arg His Ala Arg Thr Asn Ser
1               5                   10                  15

Thr Leu Ser Arg Arg Asn Phe Leu Ala Ala Thr Gly Leu Ala Val Gly
            20                  25                  30

Ala Ala Ala Leu Ser Ser Ser Trp Thr Thr Ala Ala Ala Pro Arg
        35                  40                  45

Arg Ala Leu Ser Asp Gly Asp Arg Val Pro Ala Leu Val Ile Gly Ser
    50                  55                  60

Gly Tyr Gly Gly Ala Val Ala Ala Leu Arg Leu Thr Gln Ala Gly Ile
65                  70                  75                  80

Asp Thr His Met Val Glu Met Gly Lys Ser Trp Thr Thr Pro Gly Ser
                85                  90                  95

Asp Gly Lys Val Phe Cys Pro Met Leu Ser Pro Asp Gly Arg Ser Phe
            100                 105                 110

Trp Leu Arg Asp Arg Thr Val Gln Pro Val Ser His Phe Ser Gly Gly
```

```
            115                 120                 125
Ser Val Asp Lys Asn Ile Ser Arg Tyr Val Gly Val Leu Asp Ala Glu
130                 135                 140

Asp Phe Gly Gly Ile Lys Val Tyr Gln Gly Arg Gly Val Gly Gly Gly
145                 150                 155                 160

Ser Leu Val Asn Gly Gly Xaa Ala Val Thr Pro Lys Arg Asn Tyr Phe
                165                 170                 175

Glu Glu Ile Leu Pro Gly Val Asp Ser Asn Glu Met Tyr Ser Thr Tyr
                180                 185                 190

Phe Pro Arg Ala Asn Ala Ala Leu Gly Val Asn Asn Ile Asp Pro Ala
            195                 200                 205

Trp Phe Glu Ser Thr Glu Tyr Tyr Lys Phe Ala Arg Thr Gly Arg Lys
        210                 215                 220

Thr Ala Glu Arg Ser Gly Tyr Thr Thr Thr Phe Xaa Pro Asn Val Tyr
225                 230                 235                 240

Asp Phe Asn Tyr Met Lys Gln Glu Ala Ala Gly Gln Val Thr Lys Ser
                245                 250                 255

Ala Leu Val Ser Glu Val Ile Tyr Gly Asn Asn Ala Gly Lys Lys Ser
                260                 265                 270

Leu Asp Lys Thr Tyr Leu Ala Ala Ala Ser Ala Thr Gly Lys Leu Thr
            275                 280                 285

Ile Ser Ala Leu His Val Val Thr Ser Val Ala Pro Ala Ala Thr Gly
        290                 295                 300

Gly Gly Tyr Gln Val Val Met Asn Gln Ile Asn Glu Gln Gly Asn Thr
305                 310                 315                 320

Val Gly Thr Lys Thr Val Thr Ala Asp Lys Val Phe Phe Ala Ala Gly
                325                 330                 335

Ser Ile Gly Thr Ser Lys Leu Leu Val Ala Met Lys Ala Gln Gly Gln
                340                 345                 350

Leu Ala Asn Leu Pro Gly Ala Val Gly Gln Glu Trp Gly His Asn Gly
            355                 360                 365

Asn Val Met Val Gly Arg Ala Asn His Met Trp Asp Ala Thr Gly Ala
        370                 375                 380

Lys Gln Ser Ala Ile Pro Val Met Gly Ile Asp Asn Trp Ala Asp Thr
385                 390                 395                 400

Ser Ala Pro Val Xaa Ala Glu Ile Ala Pro Phe Pro Ala Gly Thr Glu
                405                 410                 415

Leu Trp Val Ser Leu Tyr Leu Ala Ile Ala Lys Asn Pro Gln Arg Ala
                420                 425                 430

Gln Phe Gln Phe Asn Ser Ala Thr Gly Lys Val Gly Leu Asn Trp Gln
            435                 440                 445

Arg Ser Gln Asn Gln Pro Ser Ile Asp Met Ala Lys Lys Leu Phe Asp
        450                 455                 460

Lys Ile Asn Lys Lys Glu Gly Thr Ile Tyr Arg Thr Asp Leu Phe Gly
465                 470                 475                 480

Pro Val Gln Thr Trp Gly Asp Gln Leu Thr Tyr His Pro Leu Gly Gly
                485                 490                 495

Cys Val Leu Gly Lys Ala Thr Asp Gly Tyr Gly Arg Leu Pro Glu Tyr
                500                 505                 510

Pro Gly Leu Tyr Val Met Asp Gly Ser Leu Val Pro Gly Asn Val Gly
            515                 520                 525

Val Asn Pro Phe Val Thr Ile Thr Ala Leu Ala Glu Arg Asn Ile Glu
        530                 535                 540
```

Asn Ile Ile Ala Asn Asp Met Asn
545                 550

<210> SEQ ID NO 35
<211> LENGTH: 522
<212> TYPE: PRT
<213> ORGANISM: Rhodococcus erythropolis
<220> FEATURE:
<221> NAME/KEY: MISC_FEATURE
<222> LOCATION: (137)..(137)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (206)..(206)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (375)..(375)
<223> OTHER INFORMATION: Xaa is Phe, Trp, Ser, Thr, Lys, Ala, Asn, His
      or Asp, provided that when Xaa137 is Met, then Xaa375 is not Phe

<400> SEQUENCE: 35

Met Gly Ala Ala Ala Leu Ser Ser Ser Trp Thr Thr Ala Ala Ala
1               5                   10                  15

Pro Arg Arg Ala Leu Asn Asp Gly Asp Arg Val Pro Ala Leu Val Ile
                20                  25                  30

Gly Ser Gly Tyr Gly Gly Ala Val Ala Leu Arg Leu Thr Gln Ala
            35                  40                  45

Gly Ile Asp Thr His Met Val Glu Met Gly Lys Ser Trp Thr Thr Pro
50                  55                  60

Gly Ser Asp Gly Lys Val Phe Cys Pro Met Leu Ser Pro Asp Gly Arg
65                  70                  75                  80

Ser Phe Trp Leu Arg Asp Arg Thr Val Gln Pro Val Ser His Phe Ser
                85                  90                  95

Gly Gly Ser Val Asp Lys Asn Ile Ser Arg Tyr Val Gly Val Leu Asp
                100                 105                 110

Ala Glu Asp Phe Gly Gly Ile Lys Val Tyr Gln Gly Arg Gly Val Gly
            115                 120                 125

Gly Gly Ser Leu Val Asn Gly Gly Xaa Ala Val Thr Pro Lys Arg Asn
            130                 135                 140

Tyr Phe Glu Glu Ile Leu Pro Gly Val Asp Ser Asn Glu Met Tyr Ser
145                 150                 155                 160

Thr Tyr Phe Pro Arg Ala Asn Ala Ala Leu Gly Val Asn Asn Ile Asp
                165                 170                 175

Pro Ala Trp Phe Glu Ser Thr Glu Tyr Tyr Lys Phe Ala Arg Thr Gly
            180                 185                 190

Arg Lys Thr Ala Glu Arg Ser Gly Tyr Thr Thr Thr Phe Xaa Pro Asn
            195                 200                 205

Val Tyr Asp Phe Asn Tyr Met Lys Gln Glu Ala Ala Gly Gln Val Thr
        210                 215                 220

Lys Ser Ala Leu Val Ser Glu Val Ile Tyr Gly Asn Asn Ala Gly Lys
225                 230                 235                 240

Lys Ser Leu Asp Lys Thr Tyr Leu Ala Ala Ala Ser Ala Thr Gly Lys
                245                 250                 255

Leu Thr Ile Ser Ala Leu His Val Val Thr Ser Val Ala Pro Ala Ala
            260                 265                 270

Thr Gly Gly Gly Tyr Gln Val Val Met Asn Gln Ile Asn Glu Gln Gly

```
                275                 280                 285
Asn Thr Val Gly Thr Lys Thr Val Ala Asp Lys Val Phe Phe Ala
    290                 295                 300
Ala Gly Ser Ile Gly Thr Ser Lys Leu Leu Val Ala Met Lys Ala Gln
305                 310                 315                 320
Gly Gln Leu Ala Asn Leu Pro Gly Ala Val Gly Gln Glu Trp Gly His
                325                 330                 335
Asn Gly Asn Val Met Val Gly Arg Ala Asn His Met Trp Asp Ala Thr
            340                 345                 350
Gly Ala Lys Gln Ser Ala Ile Pro Val Met Gly Ile Asp Asn Trp Ala
        355                 360                 365
Asp Thr Ser Ala Pro Val Xaa Ala Glu Ile Ala Pro Phe Pro Ala Gly
    370                 375                 380
Thr Glu Leu Trp Val Ser Leu Tyr Leu Ala Ile Ala Lys Asn Pro Gln
385                 390                 395                 400
Arg Ala Gln Phe Gln Phe Asn Ser Ala Thr Gly Lys Val Gly Leu Asn
                405                 410                 415
Trp Gln Arg Ser Gln Asn Gln Pro Ser Ile Asp Met Ala Lys Lys Leu
            420                 425                 430
Phe Asp Lys Ile Asn Lys Lys Glu Gly Thr Ile Tyr Arg Thr Asp Leu
        435                 440                 445
Phe Gly Pro Thr Gln Thr Trp Gly Asp Gln Leu Thr Tyr His Pro Leu
    450                 455                 460
Gly Gly Cys Val Leu Gly Lys Ala Thr Asp Gly Tyr Gly Arg Leu Pro
465                 470                 475                 480
Glu Tyr Pro Gly Leu Tyr Val Met Asp Gly Ser Leu Val Pro Gly Asn
                485                 490                 495
Val Gly Val Asn Pro Phe Val Thr Ile Thr Ala Leu Ala Glu Arg Asn
            500                 505                 510
Ile Glu Asn Ile Ile Ala Asn Asp Met Asn
        515                 520

<210> SEQ ID NO 36
<211> LENGTH: 523
<212> TYPE: PRT
<213> ORGANISM: Amycolatopsis mediterranei
<220> FEATURE:
<221> NAME/KEY: MISC_FEATURE
<222> LOCATION: (142)..(142)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (211)..(211)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (377)..(377)
<223> OTHER INFORMATION: Xaa is Phe, Trp, Ser, Thr, Lys, Ala, Asn, His
      or Asp, provided that when Xaa142 is Met, then Xaa377 is not Phe

<400> SEQUENCE: 36

Met Ala Ser Ala Ala Leu Ala Gly Arg Ala Thr Ala Ala Ser Ser Gln
1               5                   10                  15
Pro Ala Val Ala Gly Ser Ala Ala Ile Ser Asp Gly Ala Arg Val
            20                  25                  30
Thr Ala Leu Val Ile Gly Thr Gly Tyr Gly Gly Ser Val Ala Ala Leu
        35                  40                  45
```

```
Arg Leu Ala Gln Ala Gly Val Asp Val Gln Met Val Glu Met Gly Met
    50              55                  60

Ala Trp Asp Thr Pro Gly Ala Asp Gly Lys Ile Phe Cys Thr Thr Pro
65              70                  75                  80

Asn Pro Asp Gln Arg Ser Phe Trp Leu Arg Thr Arg Thr Lys Gln Pro
                85                  90                  95

Leu Ser Asn Phe Leu Gly Phe Pro Ile Asp Lys Asp Ile Pro Arg Tyr
            100                 105                 110

Thr Gly Ile Leu Asp Ala Glu Glu Phe Ser Gly Ile Thr Val Tyr Gln
            115                 120                 125

Gly Arg Gly Val Gly Gly Ser Leu Val Asn Gly Gly Xaa Ala Val
    130                 135                 140

Thr Pro Lys Arg Glu Asn Phe Gly Ala Ile Leu Pro Thr Val Asp Ala
145             150                 155                 160

Asn Glu Met Tyr Asp Val Tyr Tyr Pro Arg Ala Asn Ala Gly Leu Gly
                165                 170                 175

Val Ala Ser Val Arg Pro Ala Trp Phe Glu Thr Thr Asp Trp Tyr Gln
            180                 185                 190

Phe Ala Arg Val Gly Arg Lys Gln Ala Gln Arg Ser Gly Phe Pro Phe
            195                 200                 205

Val Phe Xaa Pro Asp Val Tyr Asp Trp Asp Tyr Met Glu Arg Glu Ala
    210                 215                 220

Ala Gly Thr Ala Thr Lys Ser Ala Leu Ala Gly Glu Ile Leu Phe Gly
225             230                 235                 240

Asn Asn Tyr Gly Lys Lys Ser Leu Gln Lys Thr Tyr Leu Pro Lys Ile
                245                 250                 255

Ala Ala Thr Gly Arg Val Thr Ile Ser Pro Leu His Arg Val Thr Gln
            260                 265                 270

Val Val Pro Ala Ser Gly Gly Tyr Thr Val Thr Ile Glu Gln Leu
    275                 280                 285

Thr Thr Asp Gly Ala Val Ser Ala Ile Lys Thr Val Thr Ala Ala Lys
    290                 295                 300

Val Phe Phe Ala Ala Gly Ser Val Gly Thr Ser Lys Leu Leu Val Lys
305             310                 315                 320

Leu Lys Ala Thr Gly Ala Leu Pro Asn Leu Asn Gly Glu Val Gly Lys
            325                 330                 335

Gly Trp Gly Asp Asn Gly Asn Val Met Val Gly Arg Ala Asn Gln Ile
                340                 345                 350

Trp Asp Pro Thr Gly Ala Ser Gln Ser Thr Ile Pro Cys Gly Gly Ile
            355                 360                 365

Asp Asn Trp Ala Ala Gly Gly Ala Xaa Ala Glu Val Ala Pro Leu Pro
    370                 375                 380

Thr Gly Ile Glu Thr Trp Ala Ser Phe Tyr Leu Ser Ile Thr Lys Asn
385             390                 395                 400

Pro Asn Arg Ala Gln Phe Thr Trp Asn Pro Thr Thr Arg Ala Val Asp
                405                 410                 415

Leu Asn Trp Gln Thr Ala Trp Lys Gln Pro Gly Ile Asp Met Ala Lys
            420                 425                 430

Thr Ile Phe Asp Lys Ile Asn Ala Thr Glu Gly Thr Ile Tyr Arg Thr
            435                 440                 445

Asp Leu Phe Gly Thr Tyr Lys Thr Trp Gly Asp His Leu Thr Tyr His
    450                 455                 460

Pro Leu Gly Gly Ala Val Leu Gly Lys Ala Thr Asp Asn Tyr Gly Arg
```

```
                465                 470                 475                 480

Leu Ala Gly His Pro Gly Leu Tyr Ala Ile Asp Gly Ser Leu Ile Pro
                    485                 490                 495

Gly Asn Thr Ser Val Asn Pro Phe Val Thr Ile Thr Ala Leu Ala Glu
                500                 505                 510

Arg Asn Ile Glu Lys Ile Ile Ala Gln Asp Phe
                515                 520

<210> SEQ ID NO 37
<211> LENGTH: 547
<212> TYPE: PRT
<213> ORGANISM: Streptosporangium roseum
<220> FEATURE:
<221> NAME/KEY: MISC_FEATURE
<222> LOCATION: (166)..(166)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (235)..(235)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (401)..(401)
<223> OTHER INFORMATION: Xaa is Phe, Trp, Ser, Thr, Lys, Ala, Asn, His
      or Asp, provided that when Xaa166 is Met, then Xaa401 is not Phe

<400> SEQUENCE: 37

Met Ser Asp Asn Thr Ser Gly Ser Thr Asp Ser Lys Gly Ile Ser Arg
1               5                   10                  15

Arg Gly Phe Ile Ala Gly Thr Gly Ser Ile Leu Gly Val Ala Ala Leu
            20                  25                  30

Thr Gly Arg Ala Thr Ala Ala Gln Ala Ala Leu Pro Ala Ala Ala
        35                  40                  45

Pro Ile Ser Ser Gly Ala His Val Pro Ala Leu Val Ile Gly Thr Gly
    50                  55                  60

Tyr Gly Gly Ser Val Ala Ala Leu Arg Leu Ala Gln Ala Gly Val Asp
65                  70                  75                  80

Val His Met Ile Glu Met Gly Met Ala Trp Asp Thr Pro Gly Ser Asp
                85                  90                  95

Gly Lys Ile Phe Cys Asn Thr Arg Glu Pro Asp Tyr Arg Ser Tyr Trp
            100                 105                 110

Leu Arg Thr Lys Ser Lys Ala Pro Leu Asn Tyr Phe Leu Gly Phe Pro
        115                 120                 125

Ile Asp Arg Asn Ile Pro Arg Tyr Thr Gly Ile Leu Asp Ala Glu Asp
    130                 135                 140

Phe Ser Gly Ile Thr Val Tyr Gln Gly Arg Gly Val Gly Gly Gly Ser
145                 150                 155                 160

Leu Val Asn Gly Gly Xaa Ala Val Thr Pro Lys Arg Glu Asn Phe Gly
                165                 170                 175

Ala Val Leu Pro Ser Val Asn Ala Ala Glu Met Tyr Asp Ile Tyr Tyr
            180                 185                 190

Pro Arg Ala Asn Ala Gly Leu Gly Val Ser Ser Ile Asp Pro Ala Trp
        195                 200                 205

Phe Asp Ser Thr Ala Cys Tyr Gln Tyr Ala Arg Val Gly Arg Lys His
    210                 215                 220

Ala Gln Arg Ser Gly Phe Pro Phe Val Phe Xaa Pro Asp Val Tyr Asp
225                 230                 235                 240
```

```
Trp Asp Tyr Met Lys Gln Glu Ala Ala Gly Thr Val Thr Lys Ser Ala
            245                 250                 255

Leu Ala Gly Glu Ile Leu Tyr Gly Asn Asn His Gly Lys Lys Ser Leu
        260                 265                 270

Gln Gln Thr Tyr Ile Ala Arg Ala Lys Ala Thr Gly Arg Val Ala Ile
    275                 280                 285

Ser Pro Leu His Lys Val Thr Ser Val Ala Pro Ala Ala Gly Gly Gly
290                 295                 300

Tyr Thr Val Val Ile Asp Gln Ile Asn Thr Asn Gly Asp Thr Thr Ala
305                 310                 315                 320

Thr Lys Thr Val Thr Ala Asp Arg Val Phe Phe Ala Ala Gly Ser Val
                325                 330                 335

Gly Thr Ser Lys Leu Leu Val Lys Leu Lys Ala Thr Gly Ala Leu Pro
            340                 345                 350

Asn Leu Asn Asp Glu Ile Gly Lys Gly Trp Asp Asn Gly Asn Val
        355                 360                 365

Met Cys Gly Arg Ala Asn His Met Trp Asp Pro Thr Gly Ser Leu Gln
    370                 375                 380

Ser Ala Ile Pro Cys Ala Gly Ile Asp Asn Trp Ala Ala Gly Gly Ala
385                 390                 395                 400

Xaa Ala Glu Val Ala Pro Leu Pro Thr Gly Ile Glu Thr Tyr Ala Ser
                405                 410                 415

Phe Tyr Leu Ser Ile Thr Lys Asn Pro Asn Arg Ala Gln Phe Ser Trp
            420                 425                 430

Asn Ala Ala Thr Gly Lys Val Asp Leu Asn Trp Gln Thr Ser Trp Lys
        435                 440                 445

Gln Pro Ser Ile Asp Met Ala Lys Thr Ile Phe Asp Lys Ile Asn Ser
    450                 455                 460

Lys Glu Gly Thr Ile Tyr Arg Thr Asp Leu Phe Gly Thr Tyr Lys Ile
465                 470                 475                 480

Trp Gly Asp His Leu Thr Tyr His Pro Leu Gly Gly Ala Val Leu Asn
                485                 490                 495

Lys Ala Thr Asp Asn Tyr Gly Arg Leu Ala Gly His Pro Gly Leu Tyr
            500                 505                 510

Val Ile Asp Gly Ser Leu Ile Pro Gly Asn Thr Ser Val Asn Pro Phe
        515                 520                 525

Val Thr Ile Thr Ala Leu Ala Glu Arg Asn Ile Glu Lys Ile Ile Ala
    530                 535                 540

Thr Asp Leu
545

<210> SEQ ID NO 38
<211> LENGTH: 549
<212> TYPE: PRT
<213> ORGANISM: Streptomyces sp.
<220> FEATURE:
<221> NAME/KEY: MISC_FEATURE
<222> LOCATION: (168)..(168)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (237)..(237)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (403)..(403)
<223> OTHER INFORMATION: Xaa is Phe, Trp, Ser, Thr, Lys, Ala, Asn, His
``` or Asp, provided that when Xaa168 is Met, then Xaa403 is not Phe

<400> SEQUENCE: 38

```
Met Ser Asp Lys Ser Leu His Ser Lys Val Ser Gly Gly Val Ser Arg
1               5                   10                  15
Arg Gly Phe Ile Ala Gly Thr Gly Ser Ile Leu Gly Ala Val Ala Leu
            20                  25                  30
Thr Val Asn Val Thr Pro Ala His Ala Glu Pro Ala Thr Thr Thr Ala
        35                  40                  45
Ser Gly Pro Ile Glu Ser Gly Ala Arg Val Pro Val Leu Val Ile Gly
    50                  55                  60
Thr Gly Tyr Gly Gly Ser Val Ala Ala Leu Arg Leu Ala Gln Ala Gly
65                  70                  75                  80
Val Pro Val His Met Val Glu Met Gly Met Ala Trp Asp Thr Pro Gly
                85                  90                  95
Ser Asp Gly Lys Ile Phe Ala Asn Thr Thr Lys Pro Asp Tyr Arg Ser
            100                 105                 110
Tyr Trp Leu Arg Thr Arg Thr Lys Ala Pro Leu Ser Asn Phe Leu Gly
        115                 120                 125
Phe Pro Ile Asp Lys Asp Val Pro Arg Tyr Thr Gly Ile Leu Asp Ala
    130                 135                 140
Glu Met Gly Gly Ile Ile Val Tyr Gln Gly Arg Gly Val Gly Gly Gly
145                 150                 155                 160
Gly Ser Leu Val Asn Gly Gly Xaa Ala Val Thr Pro Lys Arg Gln Asn
                165                 170                 175
Phe Ala Ala Ile Leu Pro Ser Val Asp Ala Glu Met Tyr Arg Thr
            180                 185                 190
Tyr Tyr Pro Arg Ala Asn Ala Gly Leu Gly Val Gly Leu Ile Asp Pro
        195                 200                 205
Val Trp Phe Glu Ala Val Asp Cys Tyr Gln Phe Ala Arg Val Gly Arg
    210                 215                 220
Lys His Ala Gln Arg Ser Gly Phe Pro Phe Val Phe Xaa Pro Asp Val
225                 230                 235                 240
Tyr Asp Trp Asp Tyr Met Lys Gln Glu Val Ala Gly Thr Val Pro Lys
                245                 250                 255
Ser Ala Val Asp Gly Glu Ile Leu Tyr Gly Asn Asn Ala Gly Lys Lys
            260                 265                 270
Ser Leu Gln Gln Thr Tyr Leu Ala Ala Ala Arg Ala Thr Gly Lys Val
        275                 280                 285
Thr Ile Ser Pro Leu His Arg Val Thr Thr Val Ser Pro Ser Asp Gly
    290                 295                 300
Gly Gly Tyr Thr Val Val Met Glu Gln Leu Ser Thr Ser Gly Asp Val
305                 310                 315                 320
Leu Ala Thr Lys Thr Val Thr Ala Gly Arg Val Phe Phe Ala Ala Gly
                325                 330                 335
Ser Val Gly Thr Ser Lys Leu Leu Val Arg Leu Lys Ala Thr Gly Ala
            340                 345                 350
Leu Pro Asn Leu Asn Asp Glu Val Gly Lys Gly Trp Gly Asp Asn Gly
        355                 360                 365
Asn Val Met Cys Gly Arg Ala Asn His Met Trp Asp Pro Thr Gly Lys
    370                 375                 380
Val Gln Ala Ser Ile Pro Cys Gly Gly Ile Asp Asn Trp Asp Ala Gly
385                 390                 395                 400
```

-continued

```
Gly Ala Xaa Ala Glu Val Ala Pro Leu Pro Thr Gly Ile Glu Thr Tyr
            405                 410                 415

Ala Ser Phe Tyr Leu Ser Ile Thr Lys Asn Pro Asn Arg Ala Arg Phe
            420                 425                 430

Ser Trp Asn Ala Ala Gly Lys Val Glu Leu Asp Trp Gln Thr Ala
            435                 440                 445

Trp Lys Gln Pro Ser Ile Asp Met Ala Lys Thr Ile Phe Asp Lys Ile
    450                 455                 460

Asn Ala Lys Glu Gly Thr Ile Tyr Arg Thr Asp Leu Phe Gly Thr Asn
465                 470                 475                 480

Lys Val Trp Gly Asp His Leu Thr Tyr His Pro Leu Gly Gly Ala Val
                485                 490                 495

Leu Gly Lys Ala Thr Asp Asn Tyr Gly Arg Leu His Gly His Pro Gly
                500                 505                 510

Leu Tyr Val Ile Asp Gly Ala Leu Ile Pro Gly Asn Thr Ser Val Asn
                515                 520                 525

Pro Phe Ala Thr Ile Thr Ala Leu Ala Glu Arg Asn Ile Glu Lys Ile
    530                 535                 540

Ile Ala Thr Asp Leu
545
```

<210> SEQ ID NO 39
<211> LENGTH: 546
<212> TYPE: PRT
<213> ORGANISM: Catenulispora acidiphila
<220> FEATURE:
<221> NAME/KEY: MISC_FEATURE
<222> LOCATION: (165)..(165)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (234)..(234)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (400)..(400)
<223> OTHER INFORMATION: Xaa is Phe, Trp, Ser, Thr, Lys, Ala, Asn, His
      or Asp, provided that when Xaa165 is Met, then Xaa400 is not Phe

<400> SEQUENCE: 39

```
Met Ser Ala Thr Ser Arg His Asp Pro Gly Ala Arg Gly Leu Ser Arg
1               5                   10                  15

Arg Gly Phe Leu Ala Gly Thr Gly Thr Val Leu Gly Ala Ala Ala Leu
            20                  25                  30

Gly Gly Leu Ser Ala Ser Arg Ala Ser Ala Ala Gln Arg Ser Thr Pro
        35                  40                  45

Ile Ser Asn Gly Ala His Val Gln Ala Leu Ile Ile Gly Thr Gly Tyr
    50                  55                  60

Gly Gly Ser Val Ala Ala Leu Arg Leu Ala Gln Ala Gly Ile Ala Val
65                  70                  75                  80

Glu Met Ile Glu Met Gly Met Ala Trp Asp Thr Pro Gly Ser Asp Gly
                85                  90                  95

Lys Ile Phe Cys Asn Leu Thr Ser Pro Asp Arg Ser Phe Trp Leu
            100                 105                 110

Arg Thr Gln Thr Lys Gln Pro Val Gly Tyr Phe Leu Gly Ile Pro Ile
        115                 120                 125

Asp Arg Ala Ile Pro Asn Tyr Thr Gly Ile Leu Asp Ala Glu Asp Phe
    130                 135                 140
```

```
Ala Gly Ile Thr Val Tyr Gln Gly Arg Gly Ile Gly Gly Ser Leu
145                 150                 155                 160

Val Asn Gly Gly Xaa Ala Val Thr Pro Lys Gln Glu Asn Phe Gly Ala
                165                 170                 175

Ile Leu Pro Ser Val Asn Pro Ala Glu Met Tyr Asn Val Tyr Tyr Pro
            180                 185                 190

Arg Ala Asn Ala Gly Leu Gly Ala Gly Val Val Pro Gln Ser Trp Phe
        195                 200                 205

Thr Lys Thr Asp Trp Tyr Gln Phe Ala Arg Val Gly Gln Lys Gln Ala
    210                 215                 220

Gly Arg Ser Gly Phe Pro Phe Gln Phe Xaa Pro Asp Val Tyr Asp Trp
225                 230                 235                 240

Asn Tyr Met Gln Gln Glu Asp Ala Gly Thr Val Pro Lys Ser Ala Leu
                245                 250                 255

Gly Gln Glu Leu Leu Tyr Gly Asn Asn Tyr Gly Lys Lys Ser Leu Gln
            260                 265                 270

Lys Thr Tyr Ile Pro Ala Ala Leu Ala Thr Gly Lys Val Asn Ile Ser
        275                 280                 285

Pro Leu His Lys Val Thr Ser Val Ser Pro Ala Ser Gly Gly Gly Tyr
    290                 295                 300

Thr Val Leu Met Asn Gln Leu Asp Thr Ser Gly Asn Val Val Val Thr
305                 310                 315                 320

Lys Glu Val Thr Ala Asp Lys Val Val Phe Ala Ala Gly Ser Val Gly
                325                 330                 335

Thr Ser Lys Leu Leu Val Gln Met Arg Asp Thr Gly Gln Leu Pro His
            340                 345                 350

Leu Asn Asp Gln Val Gly Gln Gly Trp Gly Asp Asn Gly Asn Ile Met
        355                 360                 365

Val Gly Arg Ala Asn Gln Ile Trp Asp Pro Thr Gly Ser Lys Gln Ser
    370                 375                 380

Thr Val Pro Cys Gly Gly Ile Asp Asn Trp Thr Lys Gly Gly Ala Xaa
385                 390                 395                 400

Ala Glu Val Ala Pro Leu Pro Ile Gly Ile Glu Thr Trp Ala Ser Leu
                405                 410                 415

Tyr Leu Ser Ile Thr Lys Asn Pro His Arg Ala Gln Phe Thr Trp Asn
            420                 425                 430

Ala Ala Thr Gln Lys Val Asp Leu Ser Trp Gln Leu Ala Trp Lys Gln
        435                 440                 445

Asp Gly Ile Thr Met Ala Lys Ser Ile Phe Asp Lys Ile Asn Ser Thr
    450                 455                 460

Glu Gly Thr Ile Tyr Arg Thr Asp Leu Phe Gly Ser Tyr Lys Thr Trp
465                 470                 475                 480

Gln Asp Gln Leu Thr Tyr His Pro Leu Gly Gly Ala Val Leu Asn Gln
                485                 490                 495

Ala Thr Asp Asn Tyr Gly Arg Leu Thr Ala Tyr Pro Gly Leu Tyr Val
            500                 505                 510

Met Asp Gly Ala Leu Ile Pro Gly Asn Thr Ser Val Asn Pro Phe Val
        515                 520                 525

Thr Ile Thr Ala Leu Ala Glu Arg Asn Ile Glu Asn Ile Ile Ala Asn
    530                 535                 540

Gly Gly
545
```

```
<210> SEQ ID NO 40
<211> LENGTH: 550
<212> TYPE: PRT
<213> ORGANISM: Streptomyces roseosporus
<220> FEATURE:
<221> NAME/KEY: MISC_FEATURE
<222> LOCATION: (169)..(169)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (238)..(238)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (404)..(404)
<223> OTHER INFORMATION: Xaa is Phe, Trp, Ser, Thr, Lys, Ala, Asn, His
      or Asp, provided that when Xaa169 is Met, then Xaa404 is not Phe

<400> SEQUENCE: 40

Met Cys His Met Asn Asp Thr Ser Met Gln Asn Ser Glu Thr Lys Gly
1               5                   10                  15

Val Ser Arg Arg Arg Phe Ile Thr Gly Thr Gly Ser Leu Leu Gly Ala
            20                  25                  30

Ala Ala Ile Ala Gly His Ala Pro Arg Ala Trp Ala Asp Val Arg Ala
        35                  40                  45

Val Ala Ala Pro Ile Gly Ser Gly Ala His Val Pro Val Leu Val Val
    50                  55                  60

Gly Thr Gly Tyr Gly Gly Ser Val Ala Ala Leu Arg Leu Ala Glu Ala
65                  70                  75                  80

Gly Thr Asp Val His Met Val Glu Met Gly Met Ala Trp Asp Thr Pro
                85                  90                  95

Gly Ala Asp Gly Lys Ile Phe Ala Asn Thr Thr Arg Pro Asp Asp Arg
            100                 105                 110

Ser Phe Trp Leu Arg Thr Arg Thr Lys Gln Pro Leu Ser Asn Phe Leu
        115                 120                 125

Gly Phe Pro Leu Asp Lys Asp Val Asn Arg Tyr Thr Gly Ile Leu Asp
130                 135                 140

Ala Glu Glu Phe Gly Gly Ile Thr Val Tyr Gln Gly Arg Gly Val Gly
145                 150                 155                 160

Gly Gly Ser Leu Val Asn Gly Gly Xaa Ala Val Thr Pro Arg Arg Glu
                165                 170                 175

Asn Phe Gly Ala Ile Leu Pro Thr Val Asn Ala Ala Glu Met Tyr Ser
            180                 185                 190

Thr Tyr Tyr Pro Arg Ala Asn Ser Gly Leu Gly Val Thr Thr Ile Asp
        195                 200                 205

Pro Ala Trp Phe Asp Ser Val Asp Cys Tyr Gln Tyr Ala Arg Val Gly
    210                 215                 220

Arg Lys His Ala Gln Arg Ser Gly Phe Pro Phe Leu Phe Xaa Pro Ala
225                 230                 235                 240

Val Tyr Asp Trp Asp Tyr Met Lys Gln Glu Ala Ala Gly Thr Val Pro
                245                 250                 255

Lys Ser Ala Leu Asp Gly Glu Ile Leu Tyr Gly Asn Asn His Gly Lys
            260                 265                 270

Lys Ser Leu Gln Lys Thr Tyr Ile Asp Arg Ile Arg Ala Thr Gly Arg
        275                 280                 285

Val Thr Ile Ser Pro Leu His Lys Val Thr Thr Val Thr Pro Ala Pro
    290                 295                 300
```

-continued

```
Gly Gly Gly Tyr Thr Val Leu Ile Asp Gln Leu Asp Thr Gly Gly Arg
305                 310                 315                 320

Thr Thr Ala Thr Lys Thr Val Thr Ala Asp Lys Val Phe Phe Ala Ala
            325                 330                 335

Gly Ser Val Gly Thr Ser Lys Leu Leu Val Gly Leu Lys Ala Thr Gly
            340                 345                 350

Ala Leu Pro Leu Leu Asn Asp Glu Ile Gly Arg Gly Trp Gly Asp Asn
            355                 360                 365

Gly Asn Val Met Cys Gly Arg Ala Asn His Leu Trp Asp Pro Thr Gly
370                 375                 380

Lys Val Gln Ser Ser Ile Pro Thr Gly Gly Ile Asp Asn Trp Asp Ala
385                 390                 395                 400

Gly Gly Ala Xaa Ala Glu Ile Ala Pro Leu Pro Thr Gly Ile Glu Thr
                405                 410                 415

Trp Ala Ser Phe Tyr Leu Ser Ile Thr Lys Asn Pro His Arg Ala Arg
            420                 425                 430

Phe Thr Trp Asn Ala Ala Ala Gly Lys Ala Glu Leu Asp Trp Arg Thr
            435                 440                 445

Ala Trp Lys Gln Pro Ser Ile Asp Ala Ala Lys Thr Ile Phe Asp Lys
    450                 455                 460

Ile Asn Gln Lys Glu Gly Thr Ile Tyr Arg Thr Asp Leu Phe Gly Val
465                 470                 475                 480

Tyr Lys Ile Trp Gly Asp His Leu Thr Tyr His Pro Leu Gly Gly Ala
            485                 490                 495

Val Leu Asp Lys Ala Thr Asp Asn Tyr Gly Arg Leu His Gly Tyr Ser
            500                 505                 510

Gly Leu Tyr Val Ile Asp Gly Ala Leu Ile Pro Gly Asn Thr Ser Val
            515                 520                 525

Asn Pro Phe Val Thr Ile Thr Ala Leu Ala Glu Arg Asn Ile Glu Arg
            530                 535                 540

Ile Ile Ala Thr Asp Leu
545                 550
```

```
<210> SEQ ID NO 41
<211> LENGTH: 502
<212> TYPE: PRT
<213> ORGANISM: Streptomyces roseosporus
<220> FEATURE:
<221> NAME/KEY: MISC_FEATURE
<222> LOCATION: (121)..(121)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (190)..(190)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (356)..(356)
<223> OTHER INFORMATION: Xaa is Phe, Trp, Ser, Thr, Lys, Ala, Asn, His
      or Asp, provided that when Xaa121 is Met, then Xaa356 is not Phe

<400> SEQUENCE: 41

Met Ala Ala Pro Ile Gly Ser Gly Ala His Val Pro Val Leu Val Val
1               5                   10                  15

Gly Thr Gly Tyr Gly Gly Ser Val Ala Ala Leu Arg Leu Ala Glu Ala
            20                  25                  30

Gly Thr Asp Val His Met Val Glu Met Gly Met Ala Trp Asp Thr Pro
```

```
                35                  40                  45
Gly Ala Asp Gly Lys Ile Phe Ala Asn Thr Thr Arg Pro Asp Asp Arg
 50                  55                  60
Ser Phe Trp Leu Arg Thr Arg Thr Lys Gln Pro Leu Ser Asn Phe Leu
 65                  70                  75                  80
Gly Phe Pro Leu Asp Lys Asp Val Asn Arg Tyr Thr Gly Ile Leu Asp
                 85                  90                  95
Ala Glu Glu Phe Gly Ile Thr Val Tyr Gln Gly Arg Gly Val Gly
                100                 105                 110
Gly Gly Ser Leu Val Asn Gly Gly Xaa Ala Val Thr Pro Arg Arg Glu
                115                 120                 125
Asn Phe Gly Ala Ile Leu Pro Thr Val Asn Ala Ala Glu Met Tyr Ser
                130                 135                 140
Thr Tyr Tyr Pro Arg Ala Asn Ser Gly Leu Gly Val Thr Thr Ile Asp
145                 150                 155                 160
Pro Ala Trp Phe Asp Ser Val Asp Cys Tyr Gln Tyr Ala Arg Val Gly
                165                 170                 175
Arg Lys His Ala Gln Arg Ser Gly Phe Pro Phe Leu Phe Xaa Pro Ala
                180                 185                 190
Val Tyr Asp Trp Asp Tyr Met Lys Gln Glu Ala Ala Gly Thr Val Pro
                195                 200                 205
Lys Ser Ala Leu Asp Gly Glu Ile Leu Tyr Gly Asn Asn His Gly Lys
                210                 215                 220
Lys Ser Leu Gln Lys Thr Tyr Ile Asp Arg Ile Arg Ala Thr Gly Arg
225                 230                 235                 240
Val Thr Ile Ser Pro Leu His Lys Val Thr Val Thr Pro Ala Pro
                245                 250                 255
Gly Gly Gly Tyr Thr Val Leu Ile Asp Gln Leu Asp Thr Gly Gly Arg
                260                 265                 270
Thr Thr Ala Thr Lys Thr Val Thr Ala Asp Lys Val Phe Phe Ala Ala
                275                 280                 285
Gly Ser Val Gly Thr Ser Lys Leu Leu Val Gly Leu Lys Ala Thr Gly
                290                 295                 300
Ala Leu Pro Leu Leu Asn Asp Glu Ile Gly Arg Gly Trp Gly Asp Asn
305                 310                 315                 320
Gly Asn Val Met Cys Gly Arg Ala Asn His Leu Trp Asp Pro Thr Gly
                325                 330                 335
Lys Val Gln Ser Ser Ile Pro Thr Gly Gly Ile Asp Asn Trp Asp Ala
                340                 345                 350
Gly Gly Ala Xaa Ala Glu Ile Ala Pro Leu Pro Thr Gly Ile Glu Thr
                355                 360                 365
Trp Ala Ser Phe Tyr Leu Ser Ile Thr Lys Asn Pro His Arg Ala Arg
                370                 375                 380
Phe Thr Trp Asn Ala Ala Ala Gly Lys Ala Glu Leu Asp Trp Arg Thr
385                 390                 395                 400
Ala Trp Lys Gln Pro Ser Ile Asp Ala Ala Lys Thr Ile Phe Asp Lys
                405                 410                 415
Ile Asn Gln Lys Glu Gly Thr Ile Tyr Arg Thr Asp Leu Phe Gly Val
                420                 425                 430
Tyr Lys Ile Trp Gly Asp His Leu Thr Tyr His Pro Leu Gly Gly Ala
                435                 440                 445
Val Leu Asp Lys Ala Thr Asp Asn Tyr Gly Arg Leu His Gly Tyr Ser
450                 455                 460
```

```
Gly Leu Tyr Val Ile Asp Gly Ala Leu Ile Pro Gly Asn Thr Ser Val
465                 470                 475                 480

Asn Pro Phe Val Thr Ile Thr Ala Leu Ala Glu Arg Asn Ile Glu Arg
            485                 490                 495

Ile Ile Ala Thr Asp Leu
            500

<210> SEQ ID NO 42
<211> LENGTH: 547
<212> TYPE: PRT
<213> ORGANISM: Streptomyces sp.
<220> FEATURE:
<221> NAME/KEY: MISC_FEATURE
<222> LOCATION: (166)..(166)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (235)..(235)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (401)..(401)
<223> OTHER INFORMATION: Xaa is Phe, Trp, Ser, Thr, Lys, Ala, Asn, His
      or Asp, provided that when Xaa166 is Met, then Xaa401 is not Phe

<400> SEQUENCE: 42

Met Gly Asp Thr Thr Val His Lys Gly Gly Thr Gln Gly Val Ser Arg
1               5                   10                  15

Arg Arg Phe Ile Thr Gly Thr Gly Ser Leu Leu Gly Gly Ala Ala Ile
            20                  25                  30

Ala Gly His Thr Ala Pro Ala Trp Ala Thr Val Arg Ala Ala Ala Ala
        35                  40                  45

Pro Ile Gly Ser Gly Ala Arg Val Pro Ala Leu Val Ile Gly Thr Gly
50                  55                  60

Tyr Gly Gly Ser Val Ala Ala Leu Arg Leu Ala Gln Ala Gly Thr Asp
65                  70                  75                  80

Val His Met Val Glu Met Gly Met Ala Trp Asp Thr Pro Gly Ala Asp
                85                  90                  95

Gly Lys Ile Phe Ala Asn Thr Thr Arg Pro Asp Asp Arg Ser Phe Trp
            100                 105                 110

Leu Arg Thr Arg Thr Lys Gln Pro Leu Ser Asn Phe Leu Gly Phe Pro
        115                 120                 125

Ile Asp Arg Ser Val Asn Arg Tyr Thr Gly Ile Leu Asp Ala Glu Glu
    130                 135                 140

Phe Ala Gly Ile Thr Val Tyr Gln Gly Arg Gly Val Gly Gly Gly Ser
145                 150                 155                 160

Leu Val Asn Gly Gly Xaa Ala Val Thr Pro Arg Arg Glu Asn Phe Gly
                165                 170                 175

Ala Ile Leu Pro Thr Val Asn Ala Gln Glu Met Tyr Ser Thr Tyr Tyr
            180                 185                 190

Pro Arg Ala Asn Ser Gly Leu Gly Val Thr Thr Ile Asp Pro Ala Trp
        195                 200                 205

Phe Asp Ser Val Asp Cys Tyr Gln Tyr Ala Arg Val Gly Arg Lys His
    210                 215                 220

Ala Gln Arg Ser Gly Phe Pro Phe Leu Phe Xaa Pro Ala Val Tyr Asp
225                 230                 235                 240

Trp Asp Tyr Met Lys Gln Glu Ala Ala Gly Thr Val Pro Arg Ser Ala
```

```
                    245                 250                 255
        Leu Asp Ala Glu Ile Leu Tyr Gly Asn Asn Tyr Gly Lys Lys Ser Leu
                260                 265                 270

Gln Lys Thr Tyr Ile Asp Arg Ile Ala Thr Gly Arg Val Thr Ile
            275                 280                 285

Ser Pro Leu His Arg Val Thr Arg Val Thr Pro Ala Pro Gly Gly Gly
            290                 295                 300

Tyr Thr Val Leu Ile Asp Gln Leu Asn Thr Ala Gly Gln Thr Thr Ala
        305                 310                 315                 320

Thr Lys Thr Val Thr Ala Asp Lys Val Phe Phe Ala Ala Gly Ser Val
                        325                 330                 335

Gly Thr Ser Lys Leu Leu Val Gly Leu Lys Ala Thr Gly Ala Leu Pro
                    340                 345                 350

Leu Leu Asn Asp Glu Ile Gly Lys Gly Trp Gly Asp Asn Gly Asn Val
                    355                 360                 365

Met Cys Gly Arg Ala Asn His Leu Trp Asp Pro Thr Gly Lys Val Gln
            370                 375                 380

Ser Ser Ile Pro Thr Gly Gly Ile Asp Asn Trp Asp Ala Gly Gly Ala
        385                 390                 395                 400

Xaa Ala Glu Val Ala Pro Leu Pro Thr Gly Ile Glu Thr Trp Ala Ser
                        405                 410                 415

Phe Tyr Leu Ser Ile Thr Lys Asn Pro His Arg Ala Arg Phe Thr Trp
                    420                 425                 430

Asn Ala Ala Ala Gly Lys Ala Glu Leu Asp Trp Gln Thr Ala Trp Lys
                    435                 440                 445

Gln Pro Ser Ile Asp Ala Ala Lys Thr Ile Phe Asp Lys Ile Asn Gln
            450                 455                 460

Lys Glu Gly Thr Ile Tyr Arg Thr Asp Leu Phe Gly Val His Lys Ile
        465                 470                 475                 480

Trp Gly Asp His Leu Thr Tyr His Pro Leu Gly Gly Ala Val Leu Asp
                        485                 490                 495

Lys Ala Thr Asp Asn Tyr Gly Arg Leu His Gly Tyr Thr Gly Leu Tyr
                    500                 505                 510

Val Ile Asp Gly Ala Leu Ile Pro Gly Asn Thr Ser Val Asn Pro Phe
                    515                 520                 525

Val Thr Ile Thr Ala Leu Ala Glu Arg Asn Ile Glu Arg Ile Ile Ala
            530                 535                 540

Thr Asp Leu
        545

<210> SEQ ID NO 43
<211> LENGTH: 547
<212> TYPE: PRT
<213> ORGANISM: Streptomyces griseus
<220> FEATURE:
<221> NAME/KEY: MISC_FEATURE
<222> LOCATION: (166)..(166)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (235)..(235)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (401)..(401)
<223> OTHER INFORMATION: Xaa is Phe, Trp, Ser, Thr, Lys, Ala, Asn, His
      or Asp, provided that when Xaa166 is Met, then Xaa401 is not Phe
```

<400> SEQUENCE: 43

Met Gly Asp Thr Thr Val His Lys Gly Gly Thr Gln Gly Val Ser Arg
1               5                   10                  15

Arg Arg Phe Ile Thr Gly Thr Gly Ser Leu Leu Gly Gly Ala Ala Ile
            20                  25                  30

Ala Gly His Thr Ala Pro Ala Trp Ala Thr Val Arg Ala Ala Ala Ala
        35                  40                  45

Pro Ile Gly Ser Gly Ala Arg Val Pro Ala Leu Val Ile Gly Thr Gly
    50                  55                  60

Tyr Gly Gly Ser Val Ala Ala Leu Arg Leu Ala Gln Ala Gly Thr Asp
65                  70                  75                  80

Val His Met Val Glu Met Gly Met Ala Trp Asp Thr Pro Gly Ala Asp
                85                  90                  95

Gly Lys Ile Phe Ala Asn Thr Thr Arg Pro Asp Asp Arg Ser Phe Trp
            100                 105                 110

Leu Arg Thr Arg Thr Lys Gln Pro Leu Ser Asn Phe Leu Gly Phe Pro
            115                 120                 125

Ile Asp Arg Ser Val Asn Arg Tyr Thr Gly Ile Leu Asp Ala Glu Glu
130                 135                 140

Phe Ala Gly Ile Thr Val Tyr Gln Gly Arg Gly Val Gly Gly Gly Ser
145                 150                 155                 160

Leu Val Asn Gly Gly Xaa Ala Val Thr Pro Arg Arg Glu Asn Phe Gly
                165                 170                 175

Ala Ile Leu Pro Thr Val Asn Ala Gln Glu Met Tyr Ser Thr Tyr Tyr
            180                 185                 190

Pro Arg Ala Asn Ser Gly Leu Gly Val Thr Thr Ile Asp Pro Ala Trp
            195                 200                 205

Phe Asp Ser Val Asp Cys Tyr Gln Tyr Ala Arg Val Gly Arg Lys His
210                 215                 220

Ala Gln Arg Ser Gly Phe Pro Phe Leu Phe Xaa Pro Ala Val Tyr Asp
225                 230                 235                 240

Trp Asp Tyr Met Lys Gln Glu Ala Ala Gly Thr Val Pro Arg Ser Ala
            245                 250                 255

Leu Asp Ala Glu Ile Leu Tyr Gly Asn Asn Tyr Gly Lys Lys Ser Leu
            260                 265                 270

Gln Lys Thr Tyr Ile Asp Arg Ile Arg Ala Thr Gly Arg Val Thr Ile
            275                 280                 285

Ser Pro Leu His Lys Val Thr Arg Val Thr Pro Ala Pro Gly Gly Gly
            290                 295                 300

Tyr Thr Val Leu Ile Asp Gln Leu Asn Thr Ala Gly Gln Thr Thr Ala
305                 310                 315                 320

Thr Lys Thr Val Thr Ala Asp Lys Val Phe Phe Ala Ala Gly Ser Val
            325                 330                 335

Gly Thr Ser Lys Leu Leu Val Gly Leu Lys Ala Thr Gly Ala Leu Pro
            340                 345                 350

Leu Leu Asn Asp Glu Ile Gly Lys Gly Trp Gly Asp Asn Gly Asn Val
            355                 360                 365

Met Cys Gly Arg Ala Asn His Leu Trp Asp Pro Thr Gly Lys Val Gln
            370                 375                 380

Ser Ser Ile Pro Thr Gly Gly Ile Asp Asn Trp Asp Ala Gly Gly Ala
385                 390                 395                 400

Xaa Ala Glu Val Ala Pro Leu Pro Thr Gly Ile Glu Thr Trp Ala Ser

```
                    405                 410                 415
Phe Tyr Leu Ser Ile Thr Lys Asn Pro His Arg Ala Arg Phe Thr Trp
            420                 425                 430

Asn Ala Ala Ala Gly Lys Ala Glu Leu Asp Trp Gln Thr Ala Trp Lys
            435                 440                 445

Gln Pro Ser Ile Asp Ala Ala Lys Thr Ile Phe Asp Lys Ile Asn Gln
        450                 455                 460

Lys Glu Gly Thr Ile Tyr Arg Thr Asp Leu Phe Gly Val His Lys Ile
465                 470                 475                 480

Trp Gly Asp His Leu Thr Tyr His Pro Leu Gly Gly Ala Val Leu Asp
                485                 490                 495

Lys Ala Thr Asp Asn Tyr Gly Arg Leu His Gly Tyr Thr Gly Leu Tyr
            500                 505                 510

Val Ile Asp Gly Ala Leu Ile Pro Gly Asn Thr Ser Val Asn Pro Phe
        515                 520                 525

Val Thr Ile Thr Ala Leu Ala Glu Arg Asn Ile Glu Arg Ile Ile Ala
    530                 535                 540

Thr Asp Leu
545

<210> SEQ ID NO 44
<211> LENGTH: 546
<212> TYPE: PRT
<213> ORGANISM: Streptomyces sp.
<220> FEATURE:
<221> NAME/KEY: MISC_FEATURE
<222> LOCATION: (165)..(165)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (234)..(234)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (400)..(400)
<223> OTHER INFORMATION: Xaa is Phe, Trp, Ser, Thr, Lys, Ala, Asn, His
      or Asp, provided that when Xaa165 is Met, then Xaa400 is not Phe

<400> SEQUENCE: 44

Met Pro Asp Lys Gly Ser Lys Gly Phe Ser Arg Arg Gly Phe Ile Ala
1               5                   10                  15

Arg Thr Ser Ser Ile Leu Gly Ala Val Ala Val Ala Gly Gly Ala Ala
            20                  25                  30

Ala Thr Thr Ala Arg Ala Ala Val Ala Thr Ser Ala Thr Ala Ala Pro
        35                  40                  45

Ile Asp Ser Gly Ala His Val Pro Val Leu Ile Ile Gly Thr Gly Tyr
    50                  55                  60

Gly Gly Ser Val Ala Ala Leu Arg Leu Ala Gln Ala Gly Val Asp Val
65                  70                  75                  80

His Met Ile Glu Met Gly Met Ala Trp Asp Thr Pro Gly Ser Asp Gly
                85                  90                  95

Lys Ile Phe Ala Asn Thr Thr Arg Pro Asp Tyr Arg Ser Phe Trp Leu
            100                 105                 110

Arg Thr Arg Thr Lys Ala Pro Ile Ser Asn Phe Leu Gly Phe Pro Ile
        115                 120                 125

Asp Lys Asp Val Ala Arg Tyr Thr Gly Ile Leu Asp Ala Glu Glu Phe
    130                 135                 140
```

```
Asn Gly Ile Thr Val Tyr Gln Gly Arg Gly Val Gly Gly Gly Ser Leu
145                 150                 155                 160

Val Asn Gly Gly Xaa Ala Val Thr Pro Lys Arg Glu Arg Phe Gly Ala
                165                 170                 175

Val Leu Pro Ser Val Asp Ala Asp Glu Met Tyr Asp Val Tyr Tyr Pro
            180                 185                 190

Arg Ala Asn Ala Gly Leu Gly Val Thr Asn Val Asp Gln Ala Trp Trp
        195                 200                 205

Glu Thr Ala Pro Cys Tyr Gln Tyr Ala Arg Val Gly Arg Lys His Ala
210                 215                 220

Gln Arg Ser Gly Phe Pro Phe Val Phe Xaa Pro Asn Val Tyr Asp Trp
225                 230                 235                 240

Glu Tyr Met Lys Gln Glu Ala Gly Thr Val Pro Arg Ser Ser Leu
                245                 250                 255

Asp Gly Glu Val Leu Tyr Gly Asn Asn Tyr Gly Lys Lys Ser Val Gln
            260                 265                 270

Lys Thr Tyr Ile Ala Gln Ala Lys Ala Thr Gly Arg Val Ser Ile Ser
        275                 280                 285

Pro Gln His Lys Val Thr Ser Val Ala Pro Ala Thr Gly Gly Gly Tyr
290                 295                 300

Thr Val Ser Ile Asp Gln Ile Asn Thr Thr Gly Asp Thr Thr Ala Thr
305                 310                 315                 320

Lys Thr Val Thr Ala Asp Arg Val Phe Phe Ala Ala Gly Ser Val Gly
                325                 330                 335

Thr Ser Lys Leu Leu Val Arg Leu Lys Ala Thr Gly Arg Leu Pro Leu
        340                 345                 350

Leu Asn Asp Glu Val Gly Lys Gly Trp Gly Asp Asn Gly Asn Val Met
            355                 360                 365

Cys Gly Arg Ala Asn His Ile Trp Asp Ala Thr Gly Lys Leu Gln Ala
370                 375                 380

Ser Met Pro Thr Ala Gly Ile Asp Asn Trp Asp Ala Gly Gly Ala Xaa
385                 390                 395                 400

Ala Glu Val Ala Pro Leu Pro Thr Gly Ile Glu Thr Tyr Ala Ser Leu
                405                 410                 415

Tyr Leu Ser Ile Thr Lys Asn Pro His Arg Ala Glu Phe Ser Trp Asn
            420                 425                 430

Ala Ala Thr Gly Asn Val Asp Leu Asn Trp Gln Arg Ala Trp Lys Gln
        435                 440                 445

Pro Ala Ile Asp Met Ala Lys Ser Ile Phe Asp Lys Ile Asn Ser Lys
450                 455                 460

Glu Gly Thr Ile Tyr Arg Ser Asp Leu Phe Gly Gly Asn Lys Val Trp
465                 470                 475                 480

Gly Asp His Leu Thr Tyr His Pro Leu Gly Gly Ala Val Leu Asp Lys
                485                 490                 495

Ala Thr Asp Asn Tyr Gly Arg Leu His Gly Tyr Ser Gly Leu Tyr Val
            500                 505                 510

Ile Asp Gly Ser Leu Ile Pro Gly Asn Thr Ser Val Asn Pro Phe Val
        515                 520                 525

Thr Ile Thr Ala Leu Ala Glu Arg Asn Ile Glu Lys Ile Ile Ala Thr
530                 535                 540

Asp Leu
545
```

-continued

```
<210> SEQ ID NO 45
<211> LENGTH: 547
<212> TYPE: PRT
<213> ORGANISM: Streptomyces pristinaespiralis
<220> FEATURE:
<221> NAME/KEY: MISC_FEATURE
<222> LOCATION: (166)..(166)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (235)..(235)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (401)..(401)
<223> OTHER INFORMATION: Xaa is Phe, Trp, Ser, Thr, Lys, Ala, Asn, His
      or Asp, provided that when Xaa166 is Met, then Xaa401 is not Phe

<400> SEQUENCE: 45

Met Asn Ala Ala Pro Leu Pro Arg Pro Ser Gly Arg Asp Pro Ser Arg
1               5                   10                  15

Arg Gln Leu Leu Ala Gly Thr Gly Ser Ile Leu Gly Ala Val Ile Leu
            20                  25                  30

Ala Gly His Gly Pro Ala Ala Arg Ala Lys Ala Ala Pro Ala Ala
        35                  40                  45

Ala Ile Pro Asp Gly Ala His Val Pro Ala Leu Val Ile Gly Thr Gly
    50                  55                  60

Tyr Gly Gly Ser Val Ala Ala Leu Arg Leu Ala Arg Ala Gly Val Asp
65                  70                  75                  80

Val His Met Ile Glu Met Gly Met Ser Trp Asp Thr Pro Gly Pro Asp
                85                  90                  95

Gly Lys Val Phe Ala Asn Thr Thr Arg Pro Asp His Arg Ser Phe Trp
            100                 105                 110

Leu Arg Thr Arg Thr Lys Gln Pro Leu Ser Asp Phe Leu Gly Phe Pro
        115                 120                 125

Leu Asp Lys Asp Val Pro Arg Tyr Thr Gly Ile Leu Asp Ala Glu Glu
    130                 135                 140

Phe Gly Gly Ile Thr Val Tyr Gln Gly Arg Gly Val Gly Gly Gly Ser
145                 150                 155                 160

Leu Val Asn Gly Gly Xaa Ala Val Thr Pro Arg Arg Glu Asn Phe Gly
                165                 170                 175

Ala Val Leu Pro Ser Val Asn Ala Asp Glu Met Tyr Gly Ile Tyr Tyr
            180                 185                 190

Pro Arg Ala Asn Ala Ala Leu Gly Val Gly Val Val Asp Gln Gly Trp
        195                 200                 205

Trp Glu Ser Ala Ala Cys Tyr Gln Tyr Ala Arg Val Gly Arg Lys His
    210                 215                 220

Ala Glu Arg Ser Gly Phe Pro Phe Val Leu Xaa Pro Gly Val Tyr Asp
225                 230                 235                 240

Trp Asp Tyr Leu Glu Gln Glu Ala Ala Gly Thr Val Pro Ala Ser Ala
                245                 250                 255

Leu Glu Gly Glu Val Leu Phe Gly Asn Asn His Gly Lys Lys Ser Leu
            260                 265                 270

Pro Lys Thr Tyr Leu Ala Arg Ala Ala Ala Thr Gly Arg Val Val Ile
        275                 280                 285

Ser Pro Leu His Lys Val Thr Ser Val Ala Pro Ala Gly Gly Gly Gly
    290                 295                 300
```

Tyr Thr Val Val Met Glu Gln Leu Asn Thr Gly Gly Asp Val Thr Ala
305                 310                 315                 320

Val Lys Ala Val Thr Ala Asp Arg Val Phe Phe Ala Ala Gly Ser Val
            325                 330                 335

Gly Thr Ser Lys Leu Leu Thr Arg Leu Lys Ala Thr Gly Val Leu Pro
            340                 345                 350

Gly Leu Asn Gly Glu Ile Gly Lys Gly Trp Gly Asp Asn Gly Asn Val
            355                 360                 365

Met Cys Gly Arg Ala Asn His Met Trp Asp Ala Thr Gly Arg Leu Gln
370                 375                 380

Ala Ser Met Pro Thr Ala Gly Ile Asp Asn Trp Gln Ala Gly Gly Ala
385                 390                 395                 400

Xaa Ala Glu Val Ala Pro Leu Pro Thr Gly Ile Glu Thr Tyr Ala Ser
            405                 410                 415

Phe Tyr Leu Ser Ile Thr Arg Asn Pro His Arg Ala Ala Phe Ser Trp
            420                 425                 430

Asp Ala Ala Gly Lys Val Val Leu Asp Trp Arg Thr Ala Trp Lys
            435                 440                 445

Gln Pro Ser Ile Asp Ala Ala Arg Thr Ile Phe Asp Arg Ile Asn Ala
450                 455                 460

Lys Glu Gly Thr Ile Tyr Arg Thr Asp Leu Phe Gly Ala Tyr Lys Ile
465                 470                 475                 480

Trp Gly Asp His Leu Thr Tyr His Pro Leu Gly Gly Ala Val Leu Asn
                485                 490                 495

Arg Ala Thr Asp Asn Tyr Gly Arg Leu His Gly His Pro Gly Leu Tyr
            500                 505                 510

Val Ile Asp Gly Ser Leu Ile Pro Gly Asn Thr Ser Val Asn Pro Phe
            515                 520                 525

Val Thr Ile Thr Ala Leu Ala Glu Arg Asn Ile Glu Lys Ile Ile Ala
            530                 535                 540

Thr Asp Leu
545

<210> SEQ ID NO 46
<211> LENGTH: 543
<212> TYPE: PRT
<213> ORGANISM: Actinosynnema mirum
<220> FEATURE:
<221> NAME/KEY: MISC_FEATURE
<222> LOCATION: (163)..(163)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (232)..(232)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (397)..(397)
<223> OTHER INFORMATION: Xaa is Phe, Trp, Ser, Thr, Lys, Ala, Asn, His
      or Asp, provided that when Xaa163 is Met, then Xaa397 is not Phe

<400> SEQUENCE: 46

Met Thr Arg Ser Val Ser Arg Arg Ser Phe Leu Ala Gly Ala Gly Thr
1               5                   10                  15

Ala Leu Gly Ala Thr Ala Phe Ser Gly Gly Ala Ser Ala Ser Gly Ser
            20                  25                  30

Thr Ala Pro Gly Ala Pro Ala Ser Gly Arg Ser Pro Ala Gly Ile Pro
        35                  40                  45

```
Asp Gly Ala Arg Val Pro Ala Leu Val Val Gly Ser Gly Tyr Gly Gly
     50                  55                  60
Ala Val Ala Ala Leu Arg Leu Ala Gln Ala Gly Val Pro Val His Val
 65                  70                  75                  80
Val Glu Lys Gly Arg Ser Trp Asp Glu Pro Gly Trp Asp Gly Lys Val
                 85                  90                  95
Phe Ala Asn Met Leu Asn Pro Asp Glu Arg Ser Tyr Trp Leu Arg Thr
                100                 105                 110
Trp Thr Lys Gln Pro Leu Ser Asn Phe Leu Gly Leu Pro Val Asp Arg
            115                 120                 125
Ala Val Pro Arg Arg Thr Gly Ile Leu Asp Ala Glu Phe Ala Gly
        130                 135                 140
Ile Thr Val Tyr Gln Gly Arg Gly Val Gly Gly Ser Leu Val Asn
145                 150                 155                 160
Gly Gly Xaa Ala Val Thr Pro Arg Arg Glu Arg Phe Ala Ala Val Leu
            165                 170                 175
Pro Gly Val Asp Pro Glu Glu Met Tyr Ser Thr Tyr Tyr Pro Leu Ala
            180                 185                 190
Asn Ala Glu Leu Gly Thr Gly Leu Val Asp Pro Asp Trp Trp Glu Gln
            195                 200                 205
Ala Glu Cys Tyr Arg Tyr Ala Arg Val Gly Arg Ala Gln Ala Gln Arg
        210                 215                 220
Ser Gly Phe Pro Phe Glu Leu Xaa Pro Gly Val Tyr Asp Trp Ala His
225                 230                 235                 240
Leu Glu Arg Glu Glu Ala Gly Thr Ala Pro Arg Ser Ala Leu Ala Ala
                245                 250                 255
Glu Val Ile Tyr Gly Asn Asn His Gly Lys Leu Ser Leu Pro Arg Thr
            260                 265                 270
Tyr Leu Ala Arg Ala Leu Ala Thr Gly Arg Val Thr Ile Ser Ala Leu
        275                 280                 285
His Glu Val Thr Ser Val Arg Ala Val Gly Gly Tyr Glu Ala Leu
    290                 295                 300
Leu Asp Val Leu Asp Thr Asn Gly Arg Val Thr Ser Thr Lys Arg Val
305                 310                 315                 320
Glu Ala Glu Arg Val Phe Phe Ala Ala Gly Ser Val Gly Thr Ser Lys
                325                 330                 335
Leu Leu Thr Arg Leu Arg Asp Thr Gly Ala Leu Pro Ala Leu Ser Pro
            340                 345                 350
Glu Val Gly Leu Gly Trp Gly Glu Asn Gly Asn Val Met Val Gly Arg
        355                 360                 365
Ala Asn Lys Ala Ser Asp Pro Thr Gly Ala Leu Gln Ser Cys Ile Pro
    370                 375                 380
Thr Gly Gly Ile Asp Asn Trp Ala Ala Gly Ala Xaa Ala Glu Val
385                 390                 395                 400
Ala Pro Leu Pro Thr Gly Val Glu Thr Phe Thr Ser Phe Tyr Leu Ala
                405                 410                 415
Ile Thr Ala Asn Pro Arg Arg Gly Arg Phe Thr Trp Asn Pro Glu Ala
            420                 425                 430
Gly Arg Val Glu Leu Asp Trp Arg Gln Glu Trp Lys Gln Pro Ser Val
        435                 440                 445
Asp Met Ala Arg Thr Ile Phe Asp Arg Ile Asn Ser Val Glu Gly Thr
    450                 455                 460
```

```
Val Tyr Arg Ala Asp Leu Phe Gly Ala Gly Lys Val Trp Gly Asp Gly
465                 470                 475                 480

Leu Thr Tyr His Pro Leu Gly Val Val Leu Gly Arg Ala Thr Asp
            485                 490                 495

Gly His Gly Arg Leu Ala Gly Tyr Arg Gly Leu Tyr Val Val Asp Gly
            500                 505                 510

Ser Leu Ile Pro Gly Asn Thr Ser Val Asn Pro Phe Val Thr Ile Thr
            515                 520                 525

Ala Leu Ala Glu Arg Asn Leu Ala Arg Ile Val Ala Arg Asp Leu
    530                 535                 540

<210> SEQ ID NO 47
<211> LENGTH: 528
<212> TYPE: PRT
<213> ORGANISM: Chryseobacterium gleum
<220> FEATURE:
<221> NAME/KEY: MISC_FEATURE
<222> LOCATION: (142)..(142)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (211)..(211)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (380)..(380)
<223> OTHER INFORMATION: Xaa is Phe, Trp, Ser, Thr, Lys, Ala, Asn, His
      or Asp, provided that when Xaa142 is Met, then Xaa380 is not Phe

<400> SEQUENCE: 47

Met Asp Arg Lys Lys Phe Ile Arg Thr Ser Ala Leu Ala Ile Ser Gly
1               5                   10                  15

Phe Tyr Phe Leu Gln Ser Gly Leu Leu His Ala Thr Asn Arg Lys Asn
            20                  25                  30

Ser Leu Glu Lys Glu Asn Ser Asp Ala Pro Ile Val Ile Ile Gly Ser
        35                  40                  45

Gly Tyr Gly Gly Ala Val Ser Ala Leu Arg Leu Cys Glu Ala Gly Lys
50                  55                  60

Lys Val Val Met Leu Glu Met Gly Leu Asn Trp Glu Lys Ala Gly Ile
65                  70                  75                  80

Pro Phe Ser Asn Leu Leu Lys Pro Gly Lys Ser Ser Ala Trp Leu Lys
                85                  90                  95

Lys Lys Ser Ile Ala Pro Phe Met Asn Ile Phe Ser Leu Thr Pro Phe
            100                 105                 110

Thr Gly Thr Leu Asp Arg Leu Asp Phe Lys His Ile Asn Ile Trp Val
        115                 120                 125

Gly Arg Gly Val Gly Gly Ser Leu Val Asn Gly Gly Xaa Ala Val
130                 135                 140

Thr Pro Lys Glu Ser Tyr Phe Arg Glu Val Phe Pro Asp Leu Asp Ala
145                 150                 155                 160

Glu Arg Phe Tyr Ser His Tyr Phe Pro Leu Val Arg Glu Glu Leu Lys
                165                 170                 175

Val Asn Val Ile Asp Glu Gln Phe Leu Lys Asp Cys Pro Tyr Tyr Gln
            180                 185                 190

Phe Thr Arg Val Gly Glu Lys Glu Ala His Lys Ala Gly Phe Lys Thr
        195                 200                 205

Ile Arg Xaa Pro Asn Val Tyr Asp Phe Lys Tyr Met Glu Lys Glu Phe
210                 215                 220
```

```
Arg Asn Glu Val Pro Arg Ser Ala Leu Asn Thr Glu Val Ile Tyr Gly
225                 230                 235                 240

Asn Asn Tyr Gly Lys Asn Ser Leu Asp Lys Thr Tyr Leu Arg Lys Ala
            245                 250                 255

Leu Glu Thr Gly Asn Leu Glu Ile Leu Asp Leu His Arg Val Gln Thr
        260                 265                 270

Val Lys Leu Asn Asp Asp Lys Ser Tyr Thr Leu His Val Arg Gln Ile
    275                 280                 285

Asp Thr Ser Gly Ser Val Ile Ala Asp Lys Val Phe Asn Cys Lys Lys
290                 295                 300

Leu Ile Leu Ser Ala Gly Thr Met Gly Thr Leu Gln Ile Leu Leu Gln
305                 310                 315                 320

Ser Asn Ala Glu Asn Gly Phe Pro Ile His Glu Lys Ile Gly Lys Asn
            325                 330                 335

Trp Gly Asn Asn Gly Asn Phe Met Thr Gly Arg Asn Trp Val Lys Pro
        340                 345                 350

Leu Ser Gly Gly Thr Gly Ala Lys Gln Ser Thr Ile Pro Val Gly Gly
    355                 360                 365

Ile Asp Asn Trp Asp Asp Pro Glu His Gln Phe Xaa Thr Glu Ile Ala
370                 375                 380

Pro Leu Pro Met Gly Met Asp Val Ala Thr Ala Leu Tyr Leu Leu Ile
385                 390                 395                 400

Asn Arg Val Asp Lys Lys Gly Glu Val Thr Tyr Asn Lys Ala Ser Gln
            405                 410                 415

Ser Leu Thr Leu Asn Trp Asp Glu Ser Asn Thr Ala Lys Met Lys Glu
        420                 425                 430

Asn Ala Gln Tyr Phe Ile Arg Lys Met Asn Lys Ala Asn Gly Gly Thr
    435                 440                 445

Arg Ser His Leu Leu Phe Asn Asn Gly Phe Gly Ala Glu Ile Cys Tyr
450                 455                 460

His Pro Leu Gly Gly Cys Val Leu Gly Glu Ala Thr Asn Glu Tyr Gly
465                 470                 475                 480

Lys Leu Arg Asp His Glu Asn Leu Tyr Val Leu Asp Gly Ser Leu Ile
            485                 490                 495

Pro Gly Thr Ile Gly Val Asn Pro Phe Val Thr Ile Thr Ala Ile Ala
        500                 505                 510

Glu Tyr Cys Ile Glu Asn Leu Ile Arg Gln Asn Glu Phe Asn Leu Gly
    515                 520                 525

<210> SEQ ID NO 48
<211> LENGTH: 525
<212> TYPE: PRT
<213> ORGANISM: Weeksella virosa
<220> FEATURE:
<221> NAME/KEY: MISC_FEATURE
<222> LOCATION: (139)..(139)
<223> OTHER INFORMATION: Xaa is Met, Phe, Leu, Val, Cys, Ile, Ala, Gln,
      Tyr, Lys or Ser
<220> FEATURE:
<221> NAME/KEY: MISC_FEATURE
<222> LOCATION: (208)..(208)
<223> OTHER INFORMATION: Xaa is Val, Met, Ile, Ala, Thr, Lys, Cys, Ser,
      Gly, Glu, Tyr, Pro, Asn, Gln, Trp or His
<220> FEATURE:
<221> NAME/KEY: MISC_FEATURE
<222> LOCATION: (377)..(377)
<223> OTHER INFORMATION: Xaa is Phe, Trp, Ser, Thr, Lys, Ala, Asn, His
      or Asp, provided that when Xaa139 is Met, then Xaa377 is not Phe
```

```
<400> SEQUENCE: 48

Met Asn Arg Lys Ser Phe Ile Arg Lys Thr Ser Leu Gly Leu Gly Gly
1               5                   10                  15

Leu Phe Leu Tyr Lys Pro Met Ser Leu Phe Ser Lys Thr Lys Pro Lys
            20                  25                  30

Lys Glu Pro Ile Glu Lys Pro Ile Ile Ile Gly Ser Gly Tyr Gly
        35                  40                  45

Gly Ala Val Ala Ala Leu Arg Leu Cys Glu Ala Gly Lys Lys Val Cys
    50                  55                  60

Leu Leu Glu Met Gly Leu Asn Trp Glu Lys Ser Gly Glu Lys Phe Ser
65                  70                  75                  80

Pro Met Thr His Pro Gly Lys Ser Ala Ala Trp Leu Arg Lys Lys Thr
                85                  90                  95

Ile Ala Pro Phe Phe Asn Ile Phe Pro Leu Lys Pro Thr Gly Thr
            100                 105                 110

Leu Asp Arg Leu Asp Tyr Lys Asn Ile Lys Ile Trp Val Gly Arg Gly
            115                 120                 125

Val Gly Gly Gly Ser Leu Val Asn Gly Gly Xaa Ala Val Leu Pro Lys
    130                 135                 140

Lys Asn Tyr Phe Lys Glu Ile Phe Pro Thr Leu Asp Val Asp Leu Phe
145                 150                 155                 160

Tyr Asn Lys Tyr Phe Pro Leu Ala Gln Gln Glu Leu Lys Val Asn Val
            165                 170                 175

Ala Asp Glu Glu Phe Leu Gln Ser Cys Ser Tyr Tyr Lys Phe Asn Lys
            180                 185                 190

Val Gly Glu Lys Glu Ala Gln Lys Ala Gly Tyr Lys Thr Ile Arg Xaa
    195                 200                 205

Pro Asn Val Tyr Asn Phe Lys Tyr Met Glu Ala Glu Tyr Glu Asn Lys
    210                 215                 220

Val Pro Arg Ser Ala Leu Ala Gly Glu Val Ile Tyr Gly Asn Asn His
225                 230                 235                 240

Gly Lys Tyr Ser Leu Asp Lys Thr Tyr Leu Lys Lys Ala Asp Ala Thr
            245                 250                 255

Gly Asn Leu Glu Ile Leu Asp Leu His Gln Val Lys Ser Ile Ala Leu
            260                 265                 270

Asn Ser Asp His Ser Tyr Thr Leu Ser Val Asp Gln Ile Asn Thr Ser
            275                 280                 285

Gly Glu Ile Val Gln Val Lys Glu Met Arg Cys Gln Lys Leu Ile Leu
    290                 295                 300

Ala Ala Gly Thr Met Gly Ser Leu Glu Leu Leu Arg Ser Gln Ala
305                 310                 315                 320

Lys Asn Gln Leu Pro Leu Asp Glu His Ile Gly Lys Met Trp Gly Asn
            325                 330                 335

Asn Gly Asn Phe Met Thr Gly Arg Asn Trp Val Lys Ala Phe Ser Gly
            340                 345                 350

Gly Asn Gly Tyr Leu His Ser Thr Ile Pro Val Gly Ile Asp Asn
    355                 360                 365

Trp Asp Asp Pro Lys Tyr Pro Phe Xaa Ala Glu Ile Ala Pro Leu Pro
370                 375                 380

Met Gly Met Asn Val Ala Thr Ser Leu Tyr Leu Ile Ile Asn Lys Leu
385                 390                 395                 400

Asp Lys Tyr Gly Glu Val Thr Tyr His Pro Thr Glu Asp Lys Leu Asp
            405                 410                 415
```

```
Leu Lys Trp Asp Leu Ser His Thr Lys Met Lys Glu Asn Ala Arg
            420                 425                 430

His Phe Ile Lys Lys Met Asn Arg Thr Asn Gly Gly Thr Arg Ala His
            435                 440                 445

Phe Leu Phe His Asn Gly Phe Gly His Asp Ile Cys Tyr His Pro Leu
            450                 455                 460

Gly Gly Ile Val Leu Glu Lys Ala Thr Asn Pro Tyr Gly Lys Leu Asn
465                 470                 475                 480

Leu His Lys Asn Leu Phe Val Leu Asp Gly Ser Leu Ile Pro Gly Ser
                485                 490                 495

Ile Gly Val Asn Pro Phe Leu Thr Ile Thr Ala Leu Val Glu Tyr Cys
            500                 505                 510

Ile Glu His Leu Leu Gln Ser Lys Glu Phe Glu Thr Val
            515                 520                 525

<210> SEQ ID NO 49
<211> LENGTH: 28
<212> TYPE: DNA
<213> ORGANISM: Artificial Sequence
<220> FEATURE:
<223> OTHER INFORMATION: primer for point mutation

<400> SEQUENCE: 49
ggttaacggt ggcgcggcgg tggaaccg                                      28

<210> SEQ ID NO 50
<211> LENGTH: 28
<212> TYPE: DNA
<213> ORGANISM: Artificial Sequence
<220> FEATURE:
<223> OTHER INFORMATION: primer for point mutation

<400> SEQUENCE: 50
ggttaacggt ggctgcgcgg tggaaccg                                      28

<210> SEQ ID NO 51
<211> LENGTH: 28
<212> TYPE: DNA
<213> ORGANISM: Artificial Sequence
<220> FEATURE:
<223> OTHER INFORMATION: primer for point mutation

<400> SEQUENCE: 51
ggttaacggt ggcgacgcgg tggaaccg                                      28

<210> SEQ ID NO 52
<211> LENGTH: 28
<212> TYPE: DNA
<213> ORGANISM: Artificial Sequence
<220> FEATURE:
<223> OTHER INFORMATION: primer for point mutation

<400> SEQUENCE: 52
ggttaacggt ggcgaagcgg tggaaccg                                      28

<210> SEQ ID NO 53
<211> LENGTH: 28
<212> TYPE: DNA
<213> ORGANISM: Artificial Sequence
<220> FEATURE:
<223> OTHER INFORMATION: primer for point mutation

<400> SEQUENCE: 53
```

```
ggttaacggt ggcttcgcgg tggaaccg                                              28

<210> SEQ ID NO 54
<211> LENGTH: 28
<212> TYPE: DNA
<213> ORGANISM: Artificial Sequence
<220> FEATURE:
<223> OTHER INFORMATION: primer for point mutation

<400> SEQUENCE: 54
ggttaacggt ggcggtgcgg tggaaccg                                              28

<210> SEQ ID NO 55
<211> LENGTH: 28
<212> TYPE: DNA
<213> ORGANISM: Artificial Sequence
<220> FEATURE:
<223> OTHER INFORMATION: primer for point mutation

<400> SEQUENCE: 55
ggttaacggt ggccacgcgg tggaaccg                                              28

<210> SEQ ID NO 56
<211> LENGTH: 28
<212> TYPE: DNA
<213> ORGANISM: Artificial Sequence
<220> FEATURE:
<223> OTHER INFORMATION: primer for point mutation

<400> SEQUENCE: 56
ggttaacggt ggcatcgcgg tggaaccg                                              28

<210> SEQ ID NO 57
<211> LENGTH: 28
<212> TYPE: DNA
<213> ORGANISM: Artificial Sequence
<220> FEATURE:
<223> OTHER INFORMATION: primer for point mutation

<400> SEQUENCE: 57
ggttaacggt ggcaaagcgg tggaaccg                                              28

<210> SEQ ID NO 58
<211> LENGTH: 28
<212> TYPE: DNA
<213> ORGANISM: Artificial Sequence
<220> FEATURE:
<223> OTHER INFORMATION: primer for point mutation

<400> SEQUENCE: 58
ggttaacggt ggcctggcgg tggaaccg                                              28

<210> SEQ ID NO 59
<211> LENGTH: 28
<212> TYPE: DNA
<213> ORGANISM: Artificial Sequence
<220> FEATURE:
<223> OTHER INFORMATION: primer for point mutation

<400> SEQUENCE: 59
ggttaacggt ggcaacgcgg tggaaccg                                              28

<210> SEQ ID NO 60
<211> LENGTH: 28
<212> TYPE: DNA
```

```
<213> ORGANISM: Artificial Sequence
<220> FEATURE:
<223> OTHER INFORMATION: primer for point mutation

<400> SEQUENCE: 60
ggttaacggt ggcccggcgg tggaaccg                                              28

<210> SEQ ID NO 61
<211> LENGTH: 28
<212> TYPE: DNA
<213> ORGANISM: Artificial Sequence
<220> FEATURE:
<223> OTHER INFORMATION: primer for point mutation

<400> SEQUENCE: 61
ggttaacggt ggccaggcgg tggaaccg                                              28

<210> SEQ ID NO 62
<211> LENGTH: 28
<212> TYPE: DNA
<213> ORGANISM: Artificial Sequence
<220> FEATURE:
<223> OTHER INFORMATION: primer for point mutation

<400> SEQUENCE: 62
ggttaacggt ggcttcgcgg tggaaccg                                              28

<210> SEQ ID NO 63
<211> LENGTH: 28
<212> TYPE: DNA
<213> ORGANISM: Artificial Sequence
<220> FEATURE:
<223> OTHER INFORMATION: primer for point mutation

<400> SEQUENCE: 63
ggttaacggt ggctctgcgg tggaaccg                                              28

<210> SEQ ID NO 64
<211> LENGTH: 28
<212> TYPE: DNA
<213> ORGANISM: Artificial Sequence
<220> FEATURE:
<223> OTHER INFORMATION: primer for point mutation

<400> SEQUENCE: 64
ggttaacggt ggcaccgcgg tggaaccg                                              28

<210> SEQ ID NO 65
<211> LENGTH: 28
<212> TYPE: DNA
<213> ORGANISM: Artificial Sequence
<220> FEATURE:
<223> OTHER INFORMATION: primer for point mutation

<400> SEQUENCE: 65
ggttaacggt ggcgttgcgg tggaaccg                                              28

<210> SEQ ID NO 66
<211> LENGTH: 28
<212> TYPE: DNA
<213> ORGANISM: Artificial Sequence
<220> FEATURE:
<223> OTHER INFORMATION: primer for point mutation

<400> SEQUENCE: 66
ggttaacggt ggcggcgcgg tggaaccg                                              28
```

```
<210> SEQ ID NO 67
<211> LENGTH: 28
<212> TYPE: DNA
<213> ORGANISM: Artificial Sequence
<220> FEATURE:
<223> OTHER INFORMATION: primer for point mutation

<400> SEQUENCE: 67
ggttaacggt ggctacgcgg tggaaccg                                        28

<210> SEQ ID NO 68
<211> LENGTH: 28
<212> TYPE: DNA
<213> ORGANISM: Artificial Sequence
<220> FEATURE:
<223> OTHER INFORMATION: primer for point mutation

<400> SEQUENCE: 68
cggttccacc gccgcgccac cgttaacc                                        28

<210> SEQ ID NO 69
<211> LENGTH: 28
<212> TYPE: DNA
<213> ORGANISM: Artificial Sequence
<220> FEATURE:
<223> OTHER INFORMATION: primer for point mutation

<400> SEQUENCE: 69
cggttccacc gcgcagccac cgttaacc                                        28

<210> SEQ ID NO 70
<211> LENGTH: 28
<212> TYPE: DNA
<213> ORGANISM: Artificial Sequence
<220> FEATURE:
<223> OTHER INFORMATION: primer for point mutation

<400> SEQUENCE: 70
cggttccacc gcgtcgccac cgttaacc                                        28

<210> SEQ ID NO 71
<211> LENGTH: 28
<212> TYPE: DNA
<213> ORGANISM: Artificial Sequence
<220> FEATURE:
<223> OTHER INFORMATION: primer for point mutation

<400> SEQUENCE: 71
cggttccacc gcttcgccac cgttaacc                                        28

<210> SEQ ID NO 72
<211> LENGTH: 28
<212> TYPE: DNA
<213> ORGANISM: Artificial Sequence
<220> FEATURE:
<223> OTHER INFORMATION: primer for point mutation

<400> SEQUENCE: 72
cggttccacc gcgaagccac cgttaacc                                        28

<210> SEQ ID NO 73
<211> LENGTH: 28
<212> TYPE: DNA
<213> ORGANISM: Artificial Sequence
<220> FEATURE:
```

<223> OTHER INFORMATION: primer for point mutation

<400> SEQUENCE: 73
cggttccacc gcaccgccac cgttaacc                                    28

<210> SEQ ID NO 74
<211> LENGTH: 28
<212> TYPE: DNA
<213> ORGANISM: Artificial Sequence
<220> FEATURE:
<223> OTHER INFORMATION: primer for point mutation

<400> SEQUENCE: 74
cggttccacc gcgtggccac cgttaacc                                    28

<210> SEQ ID NO 75
<211> LENGTH: 28
<212> TYPE: DNA
<213> ORGANISM: Artificial Sequence
<220> FEATURE:
<223> OTHER INFORMATION: primer for point mutation

<400> SEQUENCE: 75
cggttccacc gcgatgccac cgttaacc                                    28

<210> SEQ ID NO 76
<211> LENGTH: 28
<212> TYPE: DNA
<213> ORGANISM: Artificial Sequence
<220> FEATURE:
<223> OTHER INFORMATION: primer for point mutation

<400> SEQUENCE: 76
cggttccacc gctttgccac cgttaacc                                    28

<210> SEQ ID NO 77
<211> LENGTH: 28
<212> TYPE: DNA
<213> ORGANISM: Artificial Sequence
<220> FEATURE:
<223> OTHER INFORMATION: primer for point mutation

<400> SEQUENCE: 77
cggttccacc gccaggccac cgttaacc                                    28

<210> SEQ ID NO 78
<211> LENGTH: 28
<212> TYPE: DNA
<213> ORGANISM: Artificial Sequence
<220> FEATURE:
<223> OTHER INFORMATION: primer for point mutation

<400> SEQUENCE: 78
cggttccacc gcgttgccac cgttaacc                                    28

<210> SEQ ID NO 79
<211> LENGTH: 28
<212> TYPE: DNA
<213> ORGANISM: Artificial Sequence
<220> FEATURE:
<223> OTHER INFORMATION: primer for point mutation

<400> SEQUENCE: 79
cggttccacc gccgggccac cgttaacc                                    28

```
<210> SEQ ID NO 80
<211> LENGTH: 28
<212> TYPE: DNA
<213> ORGANISM: Artificial Sequence
<220> FEATURE:
<223> OTHER INFORMATION: primer for point mutation

<400> SEQUENCE: 80
cggttccacc gcctggccac cgttaacc                                          28

<210> SEQ ID NO 81
<211> LENGTH: 28
<212> TYPE: DNA
<213> ORGANISM: Artificial Sequence
<220> FEATURE:
<223> OTHER INFORMATION: primer for point mutation

<400> SEQUENCE: 81
cggttccacc gcgaagccac cgttaacc                                          28

<210> SEQ ID NO 82
<211> LENGTH: 28
<212> TYPE: DNA
<213> ORGANISM: Artificial Sequence
<220> FEATURE:
<223> OTHER INFORMATION: primer for point mutation

<400> SEQUENCE: 82
cggttccacc gcagagccac cgttaacc                                          28

<210> SEQ ID NO 83
<211> LENGTH: 28
<212> TYPE: DNA
<213> ORGANISM: Artificial Sequence
<220> FEATURE:
<223> OTHER INFORMATION: primer for point mutation

<400> SEQUENCE: 83
cggttccacc gcggtgccac cgttaacc                                          28

<210> SEQ ID NO 84
<211> LENGTH: 28
<212> TYPE: DNA
<213> ORGANISM: Artificial Sequence
<220> FEATURE:
<223> OTHER INFORMATION: primer for point mutation

<400> SEQUENCE: 84
cggttccacc gcaacgccac cgttaacc                                          28

<210> SEQ ID NO 85
<211> LENGTH: 28
<212> TYPE: DNA
<213> ORGANISM: Artificial Sequence
<220> FEATURE:
<223> OTHER INFORMATION: primer for point mutation

<400> SEQUENCE: 85
cggttccacc gcgccgccac cgttaacc                                          28

<210> SEQ ID NO 86
<211> LENGTH: 28
<212> TYPE: DNA
<213> ORGANISM: Artificial Sequence
<220> FEATURE:
<223> OTHER INFORMATION: primer for point mutation
```

```
<400> SEQUENCE: 86
cggttccacc gcgtagccac cgttaacc                                    28

<210> SEQ ID NO 87
<211> LENGTH: 29
<212> TYPE: DNA
<213> ORGANISM: Artificial Sequence
<220> FEATURE:
<223> OTHER INFORMATION: primer for point mutation

<400> SEQUENCE: 87
gggtaccgtg tttgcgccga acgtgtatg                                   29

<210> SEQ ID NO 88
<211> LENGTH: 29
<212> TYPE: DNA
<213> ORGANISM: Artificial Sequence
<220> FEATURE:
<223> OTHER INFORMATION: primer for point mutation

<400> SEQUENCE: 88
gggtaccgtg ttttgcccga acgtgtatg                                   29

<210> SEQ ID NO 89
<211> LENGTH: 29
<212> TYPE: DNA
<213> ORGANISM: Artificial Sequence
<220> FEATURE:
<223> OTHER INFORMATION: primer for point mutation

<400> SEQUENCE: 89
gggtaccgtg tttgacccga acgtgtatg                                   29

<210> SEQ ID NO 90
<211> LENGTH: 29
<212> TYPE: DNA
<213> ORGANISM: Artificial Sequence
<220> FEATURE:
<223> OTHER INFORMATION: primer for point mutation

<400> SEQUENCE: 90
gggtaccgtg tttgaaccga acgtgtatg                                   29

<210> SEQ ID NO 91
<211> LENGTH: 29
<212> TYPE: DNA
<213> ORGANISM: Artificial Sequence
<220> FEATURE:
<223> OTHER INFORMATION: primer for point mutation

<400> SEQUENCE: 91
gggtaccgtg tttttcccga acgtgtatg                                   29

<210> SEQ ID NO 92
<211> LENGTH: 29
<212> TYPE: DNA
<213> ORGANISM: Artificial Sequence
<220> FEATURE:
<223> OTHER INFORMATION: primer for point mutation

<400> SEQUENCE: 92
gggtaccgtg tttggtccga acgtgtatg                                   29

<210> SEQ ID NO 93
<211> LENGTH: 29
```

```
<212> TYPE: DNA
<213> ORGANISM: Artificial Sequence
<220> FEATURE:
<223> OTHER INFORMATION: primer for point mutation

<400> SEQUENCE: 93
gggtaccgtg tttcacccga acgtgtatg                                         29

<210> SEQ ID NO 94
<211> LENGTH: 29
<212> TYPE: DNA
<213> ORGANISM: Artificial Sequence
<220> FEATURE:
<223> OTHER INFORMATION: primer for point mutation

<400> SEQUENCE: 94
gggtaccgtg tttatcccga acgtgtatg                                         29

<210> SEQ ID NO 95
<211> LENGTH: 29
<212> TYPE: DNA
<213> ORGANISM: Artificial Sequence
<220> FEATURE:
<223> OTHER INFORMATION: primer for point mutation

<400> SEQUENCE: 95
gggtaccgtg tttaaaccga acgtgtatg                                         29

<210> SEQ ID NO 96
<211> LENGTH: 29
<212> TYPE: DNA
<213> ORGANISM: Artificial Sequence
<220> FEATURE:
<223> OTHER INFORMATION: primer for point mutation

<400> SEQUENCE: 96
gggtaccgtg tttctgccga acgtgtatg                                         29

<210> SEQ ID NO 97
<211> LENGTH: 29
<212> TYPE: DNA
<213> ORGANISM: Artificial Sequence
<220> FEATURE:
<223> OTHER INFORMATION: primer for point mutation

<400> SEQUENCE: 97
gggtaccgtg tttatgccga acgtgtatg                                         29

<210> SEQ ID NO 98
<211> LENGTH: 29
<212> TYPE: DNA
<213> ORGANISM: Artificial Sequence
<220> FEATURE:
<223> OTHER INFORMATION: primer for point mutation

<400> SEQUENCE: 98
gggtaccgtg tttaacccga acgtgtatg                                         29

<210> SEQ ID NO 99
<211> LENGTH: 29
<212> TYPE: DNA
<213> ORGANISM: Artificial Sequence
<220> FEATURE:
<223> OTHER INFORMATION: primer for point mutation

<400> SEQUENCE: 99
```
gggtaccgtg tttccgccga acgtgtatg                                29

<210> SEQ ID NO 100
<211> LENGTH: 29
<212> TYPE: DNA
<213> ORGANISM: Artificial Sequence
<220> FEATURE:
<223> OTHER INFORMATION: primer for point mutation

<400> SEQUENCE: 100
gggtaccgtg tttcagccga acgtgtatg                                29

<210> SEQ ID NO 101
<211> LENGTH: 29
<212> TYPE: DNA
<213> ORGANISM: Artificial Sequence
<220> FEATURE:
<223> OTHER INFORMATION: primer for point mutation

<400> SEQUENCE: 101
gggtaccgtg tttttcccga acgtgtatg                                29

<210> SEQ ID NO 102
<211> LENGTH: 29
<212> TYPE: DNA
<213> ORGANISM: Artificial Sequence
<220> FEATURE:
<223> OTHER INFORMATION: primer for point mutation

<400> SEQUENCE: 102
gggtaccgtg ttttctccga acgtgtatg                                29

<210> SEQ ID NO 103
<211> LENGTH: 29
<212> TYPE: DNA
<213> ORGANISM: Artificial Sequence
<220> FEATURE:
<223> OTHER INFORMATION: primer for point mutation

<400> SEQUENCE: 103
gggtaccgtg tttaccccga acgtgtatg                                29

<210> SEQ ID NO 104
<211> LENGTH: 29
<212> TYPE: DNA
<213> ORGANISM: Artificial Sequence
<220> FEATURE:
<223> OTHER INFORMATION: primer for point mutation

<400> SEQUENCE: 104
gggtaccgtg tttggcccga acgtgtatg                                29

<210> SEQ ID NO 105
<211> LENGTH: 29
<212> TYPE: DNA
<213> ORGANISM: Artificial Sequence
<220> FEATURE:
<223> OTHER INFORMATION: primer for point mutation

<400> SEQUENCE: 105
gggtaccgtg ttttacccga acgtgtatg                                29

<210> SEQ ID NO 106
<211> LENGTH: 29
<212> TYPE: DNA
<213> ORGANISM: Artificial Sequence -continued

```
<220> FEATURE:
<223> OTHER INFORMATION: primer for point mutation

<400> SEQUENCE: 106
catacacgtt cggcgcaaac acggtaccc                                              29

<210> SEQ ID NO 107
<211> LENGTH: 29
<212> TYPE: DNA
<213> ORGANISM: Artificial Sequence
<220> FEATURE:
<223> OTHER INFORMATION: primer for point mutation

<400> SEQUENCE: 107
catacacgtt cgggcaaaac acggtaccc                                              29

<210> SEQ ID NO 108
<211> LENGTH: 29
<212> TYPE: DNA
<213> ORGANISM: Artificial Sequence
<220> FEATURE:
<223> OTHER INFORMATION: primer for point mutation

<400> SEQUENCE: 108
catacacgtt cgggtcaaac acggtaccc                                              29

<210> SEQ ID NO 109
<211> LENGTH: 29
<212> TYPE: DNA
<213> ORGANISM: Artificial Sequence
<220> FEATURE:
<223> OTHER INFORMATION: primer for point mutation

<400> SEQUENCE: 109
catacacgtt cggttcaaac acggtaccc                                              29

<210> SEQ ID NO 110
<211> LENGTH: 29
<212> TYPE: DNA
<213> ORGANISM: Artificial Sequence
<220> FEATURE:
<223> OTHER INFORMATION: primer for point mutation

<400> SEQUENCE: 110
catacacgtt cggaccaaac acggtaccc                                              29

<210> SEQ ID NO 111
<211> LENGTH: 29
<212> TYPE: DNA
<213> ORGANISM: Artificial Sequence
<220> FEATURE:
<223> OTHER INFORMATION: primer for point mutation

<400> SEQUENCE: 111
catacacgtt cggaccaaac acggtaccc                                              29

<210> SEQ ID NO 112
<211> LENGTH: 29
<212> TYPE: DNA
<213> ORGANISM: Artificial Sequence
<220> FEATURE:
<223> OTHER INFORMATION: primer for point mutation

<400> SEQUENCE: 112
catacacgtt cgggtgaaac acggtaccc                                              29
```

<210> SEQ ID NO 113
<211> LENGTH: 29
<212> TYPE: DNA
<213> ORGANISM: Artificial Sequence
<220> FEATURE:
<223> OTHER INFORMATION: primer for point mutation

<400> SEQUENCE: 113
catacacgtt cgggataaac acggtaccc                                29

<210> SEQ ID NO 114
<211> LENGTH: 29
<212> TYPE: DNA
<213> ORGANISM: Artificial Sequence
<220> FEATURE:
<223> OTHER INFORMATION: primer for point mutation

<400> SEQUENCE: 114
catacacgtt cggtttaaac acggtaccc                                29

<210> SEQ ID NO 115
<211> LENGTH: 29
<212> TYPE: DNA
<213> ORGANISM: Artificial Sequence
<220> FEATURE:
<223> OTHER INFORMATION: primer for point mutation

<400> SEQUENCE: 115
catacacgtt cggcagaaac acggtaccc                                29

<210> SEQ ID NO 116
<211> LENGTH: 29
<212> TYPE: DNA
<213> ORGANISM: Artificial Sequence
<220> FEATURE:
<223> OTHER INFORMATION: primer for point mutation

<400> SEQUENCE: 116
catacacgtt cggcataaac acggtaccc                                29

<210> SEQ ID NO 117
<211> LENGTH: 29
<212> TYPE: DNA
<213> ORGANISM: Artificial Sequence
<220> FEATURE:
<223> OTHER INFORMATION: primer for point mutation

<400> SEQUENCE: 117
catacacgtt cgggttaaac acggtaccc                                29

<210> SEQ ID NO 118
<211> LENGTH: 29
<212> TYPE: DNA
<213> ORGANISM: Artificial Sequence
<220> FEATURE:
<223> OTHER INFORMATION: primer for point mutation

<400> SEQUENCE: 118
catacacgtt cggcggaaac acggtaccc                                29

<210> SEQ ID NO 119
<211> LENGTH: 29
<212> TYPE: DNA
<213> ORGANISM: Artificial Sequence
<220> FEATURE:
<223> OTHER INFORMATION: primer for point mutation

```
<400> SEQUENCE: 119
catacacgtt cggctgaaac acggtaccc                                29

<210> SEQ ID NO 120
<211> LENGTH: 29
<212> TYPE: DNA
<213> ORGANISM: Artificial Sequence
<220> FEATURE:
<223> OTHER INFORMATION: primer for point mutation

<400> SEQUENCE: 120
catacacgtt cgggaaaaac acggtaccc                                29

<210> SEQ ID NO 121
<211> LENGTH: 29
<212> TYPE: DNA
<213> ORGANISM: Artificial Sequence
<220> FEATURE:
<223> OTHER INFORMATION: primer for point mutation

<400> SEQUENCE: 121
catacacgtt cggagaaaac acggtaccc                                29

<210> SEQ ID NO 122
<211> LENGTH: 29
<212> TYPE: DNA
<213> ORGANISM: Artificial Sequence
<220> FEATURE:
<223> OTHER INFORMATION: primer for point mutation

<400> SEQUENCE: 122
catacacgtt cggggtaaac acggtaccc                                29

<210> SEQ ID NO 123
<211> LENGTH: 29
<212> TYPE: DNA
<213> ORGANISM: Artificial Sequence
<220> FEATURE:
<223> OTHER INFORMATION: primer for point mutation

<400> SEQUENCE: 123
catacacgtt cgggccaaac acggtaccc                                29

<210> SEQ ID NO 124
<211> LENGTH: 29
<212> TYPE: DNA
<213> ORGANISM: Artificial Sequence
<220> FEATURE:
<223> OTHER INFORMATION: primer for point mutation

<400> SEQUENCE: 124
catacacgtt cgggtaaaac acggtaccc                                29

<210> SEQ ID NO 125
<211> LENGTH: 29
<212> TYPE: DNA
<213> ORGANISM: Artificial Sequence
<220> FEATURE:
<223> OTHER INFORMATION: primer for point mutation

<400> SEQUENCE: 125
gatagctctg ttgcggccga aattgcacc                                29

<210> SEQ ID NO 126
```

```
<210> SEQ ID NO 126
<211> LENGTH: 29
<212> TYPE: DNA
<213> ORGANISM: Artificial Sequence
<220> FEATURE:
<223> OTHER INFORMATION: primer for point mutation

<400> SEQUENCE: 126
gatagctctg tttgcgccga aattgcacc                              29

<210> SEQ ID NO 127
<211> LENGTH: 29
<212> TYPE: DNA
<213> ORGANISM: Artificial Sequence
<220> FEATURE:
<223> OTHER INFORMATION: primer for point mutation

<400> SEQUENCE: 127
gatagctctg ttgacgccga aattgcacc                              29

<210> SEQ ID NO 128
<211> LENGTH: 29
<212> TYPE: DNA
<213> ORGANISM: Artificial Sequence
<220> FEATURE:
<223> OTHER INFORMATION: primer for point mutation

<400> SEQUENCE: 128
gatagctctg ttgaagccga aattgcacc                              29

<210> SEQ ID NO 129
<211> LENGTH: 29
<212> TYPE: DNA
<213> ORGANISM: Artificial Sequence
<220> FEATURE:
<223> OTHER INFORMATION: primer for point mutation

<400> SEQUENCE: 129
gatagctctg ttggtgccga aattgcacc                              29

<210> SEQ ID NO 130
<211> LENGTH: 29
<212> TYPE: DNA
<213> ORGANISM: Artificial Sequence
<220> FEATURE:
<223> OTHER INFORMATION: primer for point mutation

<400> SEQUENCE: 130
gatagctctg ttcacgccga aattgcacc                              29

<210> SEQ ID NO 131
<211> LENGTH: 29
<212> TYPE: DNA
<213> ORGANISM: Artificial Sequence
<220> FEATURE:
<223> OTHER INFORMATION: primer for point mutation

<400> SEQUENCE: 131
gatagctctg ttatcgccga aattgcacc                              29

<210> SEQ ID NO 132
<211> LENGTH: 29
<212> TYPE: DNA
<213> ORGANISM: Artificial Sequence
<220> FEATURE:
<223> OTHER INFORMATION: primer for point mutation

<400> SEQUENCE: 132
```
gatagctctg ttaaagccga aattgcacc                                29

<210> SEQ ID NO 133
<211> LENGTH: 29
<212> TYPE: DNA
<213> ORGANISM: Artificial Sequence
<220> FEATURE:
<223> OTHER INFORMATION: primer for point mutation

<400> SEQUENCE: 133
gatagctctg ttctggccga aattgcacc                                29

<210> SEQ ID NO 134
<211> LENGTH: 29
<212> TYPE: DNA
<213> ORGANISM: Artificial Sequence
<220> FEATURE:
<223> OTHER INFORMATION: primer for point mutation

<400> SEQUENCE: 134
gatagctctg ttatggccga aattgcacc                                29

<210> SEQ ID NO 135
<211> LENGTH: 29
<212> TYPE: DNA
<213> ORGANISM: Artificial Sequence
<220> FEATURE:
<223> OTHER INFORMATION: primer for point mutation

<400> SEQUENCE: 135
gatagctctg ttacgccga aattgcacc                                 29

<210> SEQ ID NO 136
<211> LENGTH: 29
<212> TYPE: DNA
<213> ORGANISM: Artificial Sequence
<220> FEATURE:
<223> OTHER INFORMATION: primer for point mutation

<400> SEQUENCE: 136
gatagctctg ttccggccga aattgcacc                                29

<210> SEQ ID NO 137
<211> LENGTH: 29
<212> TYPE: DNA
<213> ORGANISM: Artificial Sequence
<220> FEATURE:
<223> OTHER INFORMATION: primer for point mutation

<400> SEQUENCE: 137
gatagctctg ttcaggccga aattgcacc                                29

<210> SEQ ID NO 138
<211> LENGTH: 29
<212> TYPE: DNA
<213> ORGANISM: Artificial Sequence
<220> FEATURE:
<223> OTHER INFORMATION: primer for point mutation

<400> SEQUENCE: 138
gatagctctg ttttcgccga aattgcacc                                29

<210> SEQ ID NO 139
<211> LENGTH: 29
<212> TYPE: DNA

```
<213> ORGANISM: Artificial Sequence
<220> FEATURE:
<223> OTHER INFORMATION: primer for point mutation

<400> SEQUENCE: 139
gatagctctg tttctgccga aattgcacc                                              29

<210> SEQ ID NO 140
<211> LENGTH: 29
<212> TYPE: DNA
<213> ORGANISM: Artificial Sequence
<220> FEATURE:
<223> OTHER INFORMATION: primer for point mutation

<400> SEQUENCE: 140
gatagctctg ttaccgccga aattgcacc                                              29

<210> SEQ ID NO 141
<211> LENGTH: 29
<212> TYPE: DNA
<213> ORGANISM: Artificial Sequence
<220> FEATURE:
<223> OTHER INFORMATION: primer for point mutation

<400> SEQUENCE: 141
gatagctctg ttgttgccga aattgcacc                                              29

<210> SEQ ID NO 142
<211> LENGTH: 29
<212> TYPE: DNA
<213> ORGANISM: Artificial Sequence
<220> FEATURE:
<223> OTHER INFORMATION: primer for point mutation

<400> SEQUENCE: 142
gatagctctg ttggcgccga aattgcacc                                              29

<210> SEQ ID NO 143
<211> LENGTH: 29
<212> TYPE: DNA
<213> ORGANISM: Artificial Sequence
<220> FEATURE:
<223> OTHER INFORMATION: primer for point mutation

<400> SEQUENCE: 143
gatagctctg tttacgccga aattgcacc                                              29

<210> SEQ ID NO 144
<211> LENGTH: 29
<212> TYPE: DNA
<213> ORGANISM: Artificial Sequence
<220> FEATURE:
<223> OTHER INFORMATION: primer for point mutation

<400> SEQUENCE: 144
ggtgcaattt cggccgcaac agagctatc                                              29

<210> SEQ ID NO 145
<211> LENGTH: 29
<212> TYPE: DNA
<213> ORGANISM: Artificial Sequence
<220> FEATURE:
<223> OTHER INFORMATION: primer for point mutation

<400> SEQUENCE: 145
ggtgcaattt cggcgcaaac agagctatc                                              29
```

<210> SEQ ID NO 146
<211> LENGTH: 29
<212> TYPE: DNA
<213> ORGANISM: Artificial Sequence
<220> FEATURE:
<223> OTHER INFORMATION: primer for point mutation

<400> SEQUENCE: 146
ggtgcaattt cggcgtcaac agagctatc                               29

<210> SEQ ID NO 147
<211> LENGTH: 29
<212> TYPE: DNA
<213> ORGANISM: Artificial Sequence
<220> FEATURE:
<223> OTHER INFORMATION: primer for point mutation

<400> SEQUENCE: 147
ggtgcaattt cggcttcaac agagctatc                               29

<210> SEQ ID NO 148
<211> LENGTH: 29
<212> TYPE: DNA
<213> ORGANISM: Artificial Sequence
<220> FEATURE:
<223> OTHER INFORMATION: primer for point mutation

<400> SEQUENCE: 148
ggtgcaattt cggcaccaac agagctatc                               29

<210> SEQ ID NO 149
<211> LENGTH: 29
<212> TYPE: DNA
<213> ORGANISM: Artificial Sequence
<220> FEATURE:
<223> OTHER INFORMATION: primer for point mutation

<400> SEQUENCE: 149
ggtgcaattt cggcgtgaac agagctatc                               29

<210> SEQ ID NO 150
<211> LENGTH: 29
<212> TYPE: DNA
<213> ORGANISM: Artificial Sequence
<220> FEATURE:
<223> OTHER INFORMATION: primer for point mutation

<400> SEQUENCE: 150
ggtgcaattt cggcgataac agagctatc                               29

<210> SEQ ID NO 151
<211> LENGTH: 29
<212> TYPE: DNA
<213> ORGANISM: Artificial Sequence
<220> FEATURE:
<223> OTHER INFORMATION: primer for point mutation

<400> SEQUENCE: 151
ggtgcaattt cggctttaac agagctatc                               29

<210> SEQ ID NO 152
<211> LENGTH: 29
<212> TYPE: DNA
<213> ORGANISM: Artificial Sequence
<220> FEATURE:

<223> OTHER INFORMATION: primer for point mutation

<400> SEQUENCE: 152
ggtgcaattt cggccagaac agagctatc                29

<210> SEQ ID NO 153
<211> LENGTH: 29
<212> TYPE: DNA
<213> ORGANISM: Artificial Sequence
<220> FEATURE:
<223> OTHER INFORMATION: primer for point mutation

<400> SEQUENCE: 153
ggtgcaattt cggccataac agagctatc                29

<210> SEQ ID NO 154
<211> LENGTH: 29
<212> TYPE: DNA
<213> ORGANISM: Artificial Sequence
<220> FEATURE:
<223> OTHER INFORMATION: primer for point mutation

<400> SEQUENCE: 154
ggtgcaattt cggcgttaac agagctatc                29

<210> SEQ ID NO 155
<211> LENGTH: 29
<212> TYPE: DNA
<213> ORGANISM: Artificial Sequence
<220> FEATURE:
<223> OTHER INFORMATION: primer for point mutation

<400> SEQUENCE: 155
ggtgcaattt cggccggaac agagctatc                29

<210> SEQ ID NO 156
<211> LENGTH: 29
<212> TYPE: DNA
<213> ORGANISM: Artificial Sequence
<220> FEATURE:
<223> OTHER INFORMATION: primer for point mutation

<400> SEQUENCE: 156
ggtgcaattt cggcctgaac agagctatc                29

<210> SEQ ID NO 157
<211> LENGTH: 29
<212> TYPE: DNA
<213> ORGANISM: Artificial Sequence
<220> FEATURE:
<223> OTHER INFORMATION: primer for point mutation

<400> SEQUENCE: 157
ggtgcaattt cggcgaaaac agagctatc                29

<210> SEQ ID NO 158
<211> LENGTH: 29
<212> TYPE: DNA
<213> ORGANISM: Artificial Sequence
<220> FEATURE:
<223> OTHER INFORMATION: primer for point mutation

<400> SEQUENCE: 158
ggtgcaattt cggcagaaac agagctatc                29

```
<210> SEQ ID NO 159
<211> LENGTH: 29
<212> TYPE: DNA
<213> ORGANISM: Artificial Sequence
<220> FEATURE:
<223> OTHER INFORMATION: primer for point mutation

<400> SEQUENCE: 159
ggtgcaattt cggcggtaac agagctatc                                           29

<210> SEQ ID NO 160
<211> LENGTH: 29
<212> TYPE: DNA
<213> ORGANISM: Artificial Sequence
<220> FEATURE:
<223> OTHER INFORMATION: primer for point mutation

<400> SEQUENCE: 160
ggtgcaattt cggcaacaac agagctatc                                           29

<210> SEQ ID NO 161
<211> LENGTH: 29
<212> TYPE: DNA
<213> ORGANISM: Artificial Sequence
<220> FEATURE:
<223> OTHER INFORMATION: primer for point mutation

<400> SEQUENCE: 161
ggtgcaattt cggcgccaac agagctatc                                           29

<210> SEQ ID NO 162
<211> LENGTH: 29
<212> TYPE: DNA
<213> ORGANISM: Artificial Sequence
<220> FEATURE:
<223> OTHER INFORMATION: primer for point mutation

<400> SEQUENCE: 162
ggtgcaattt cggcgtaaac agagctatc                                           29
```